United States Patent [19]
Spaete et al.

[11] Patent Number: 6,040,170
[45] Date of Patent: *Mar. 21, 2000

[54] HUMAN CYTOMEGALOVIRUS DNA SEQUENCES

[75] Inventors: Richard Spaete, Belmont; Tai-An Cha, San Ramon, both of Calif.

[73] Assignee: Aviron, Mountain View, Calif.

[*] Notice: This patent is subject to a terminal disclaimer.

[21] Appl. No.: 09/253,682

[22] Filed: Feb. 18, 1999

Related U.S. Application Data

[62] Division of application No. 08/926,922, Sep. 10, 1997, Pat. No. 5,925,751, which is a division of application No. 08/414,926, Mar. 31, 1995, Pat. No. 5,721,354.

[51] Int. Cl.⁷ .............................. C12N 1/20; C12N 15/00; C07H 21/04; C12Q 1/70
[52] U.S. Cl. .................................. 435/252.3; 536/23.72; 424/230.1; 435/5; 435/172.3; 435/320.1; 435/693
[58] Field of Search ...................... 536/23.72; 424/230.1; 435/5, 172.3, 252.3, 320.1, 69.3

[56] References Cited

U.S. PATENT DOCUMENTS 5,075,213  12/1991  Pande et al. .................................. 435/5
5,194,256  3/1993  Rasmussen et al. .......................... 424/8

OTHER PUBLICATIONS

Zaia, Comparative Analysis of Human Cytomegalivirus a–Sequence in Multiple Clinical Isolates etc., J. Clin. Microbio. 28 (1990) 2602–07.

Pande, Human Cytomegalovirus Strain Towne pp65 Gene: Nucleotide Sequence and Expression in *Escherichia coli*, Virology 182 (1991) 220–28.

Pande, Human Cytomegalovirus Strain pp28 Gene: Comparison to pp28 of HCMV AD169 etc, Virology 194 (1991) 762–67.

Chou, Analysis of Interstain Variation in Cytomegalovirus Glycoprotein B etc, J Inf Diseases 163 (1991) 1229–34.

Robson, Primate Cytomegalovirus Assembly Protein: Genome Location and Nucleotide Sequence, J Virol 63 (1989) 669–76.

Lehner, Comparative Sequence Analysis of Human Cytomegalovirus Strains, J Clin Microbiol 29 (1991) 2494–2502.

Fries, Frequency Distribution of Cytomegalovirus Envelop Glycoprotein Geneotypes etc, J Inf Diseases 169 (1994) 478–83.

Quinnan, Comparative Virulence and Immunogenicityt of the Towne Strain etc, Annals of Int Med 101 (1984) 478–83.

Plotkin, Lancet 1 (1984) 528–30.

Plotkin, Protective Effects of Towne Cytomegalovirus Vaccine etc, J Inf Disease 159 (1989) 860–65.

Huang, Detection of Human Cytomegalovirus and Analysis of Strain Variation, Yale J Biol and Med 49 (9176) 29–43.

Kilpatrick, Analysis of Cytomegalovirus Genomes with Restriction Endonucleases etc, J virol 18 (1976) 1095–1105.

LaFemina, Structural Organization of the DNA Molecules from Human Cytomegalovirus, in "Animal Virus Genetics", Field, BN and R Joenish, eds., Academic Press, NY 1980, pps 39–53.

Chandler, Comparison of Restriction Site Polymorphisms Among Clinical Isolates and Laboratory Strains of Hukman Cytomegalovirus, J Gen Virol 67 (1986) 2179–92.

Spaete, Human Cytomegalovirus Strain Towne Glycoprotein B etc, Virology 167 (1988) 207–25.

Marshall, Cytomegalovirus Vaccines, in "The Human Herpesviruses," RJ Whitley, B Roizman and C Lopez, eds., Raven Press, NY, pp 381–95, (1993).

(List continued on next page.)

*Primary Examiner*—Hankyel Park
*Attorney, Agent, or Firm*—Luann Cserr; Tracy Dunn

[57] ABSTRACT

Provided are novel Toledo and Towne human cytomegalovirus DNA sequences (HCMV) and proteins encoded thereby. The sequences are useful in methods and compositions for detecting HCMV infections and in immunogenic compositions for preventing HCMV infections.

10 Claims, 53 Drawing Sheets

OTHER PUBLICATIONS

Alford, Cytomegalovirus, in "The Human Herpesviruses," RJ Whitley, B Roizman and C Lopez, eds., Raven Press, NY, pp 227–55, (1993).

Chou, Differentiation of Cyutomegalovirus Strains by Restriction Analysis etc, J Inf Diseases 162 (1990) 738–42.

Pritchett, DNA Nucleotide Sequence Heterogeneity Between the Towne and AD 169 Strains of Cytomegalovirus, J Virol 36 (1980) 152–61.

```
                                                        UL133
         10         20         30         40         50  ↓     60
CGCTGTAGGG ATAAATAGTG CGATGGCGTT TGTGGGAGAA CGCAGTAGCG ATGGGTTGCG
GCGACATCCC TATTTATCAC GCTACCGCAA ACACCCTCTT GCGTCATCGC TACCCAACGC 70         80         90        100        110        120
ACGTGCACGA TCCTTCGTGG CAATGCCAAT GGGGCGTTCC CACGATTATC GTGGCCTGGA
TGCACGTGCT AGGAAGCACC GTTACGGTTA CCCCGCAAGG GTGCTAATAG CACCGGACCT 130        140        150        160        170        180
TAACATGCGC GGCTTTAGGA ATTTGGTGTT TGGCGGGATC GTCGGCGGAT GTCTCTTCGG
ATTGTACGCG CCGAAATCCT TAAACCACAA ACCGCCCTAG CAGCCGCCTA CAGAGAAGCC 190        200        210        220        230        240
GACCCGGCAT CGCAGCCGTA GTCGGCTGTT CTGTTTTCAT GATTTTCCTC TGCGCGTATC
CTGGGCCGTA GCGTCGACGT CAGCCGACAA GACAAAAGTA CTAAAAGGAG ACGGCCATAG 250        260        270        280        290        300
TCATCCGTTA CCGGGAATTC TTCAAAGACT CCGTAATCGA CCTCCTTACC TGCCGATGGG
AGTAGGCAAT GGCCCTTAAG AAGTTTCTGA GGCATTAGCT GGAGGAATGG ACGGCTACCC 310        320        330        340        350        360
TTCGCTACTG CAGCTGCAGC TGTAAGTGCA GCTGCAAATG CATCTCGGGC CCCTGTAGCC
AAGCGATGAC GTCGACGTCG ACATTCACGT CGACGTTTAC GTAGAGCCCG GGGACATCGG 370        380        390        400        410        420
GCTGCTGTTC AGCGTGTTAC AAGGAGACGA TGATTTACGA CATGGTCCAA TACGGTCATC
CGACGACAAG TCGCACAATG TTCCTCTGCT ACTAAATGCT GTACCAGGTT ATGCCAGTAG 430        440        450        460        470        480
GACGGGCGTC CGGACACGGC GACGATCCCG ACAGGGTGAT CTGCGAGATA GTCGAGAGTC
CTGCCGCAGG GCCTGTGCCG CTGCTAGGGC TGTCCCACTA GACGCTCTAT CAGCTCTCAG
```

*FIG._1A-1*

```
       490        500        510        520        530        540
CCCCGGTTTC GGGCCGGACG GTGTCCGTCC CCCCGCCGTC GGAGGAGTCC CACCAGCCCG
GGGGCCAAAG CCGCGGCTGC CACAGGCAGG GGGGCGGCAG CCTCCTCAGG GTGGTCGGGC
UL134
       550        560        570        580        590        600
TCATCCCACC GCAGCCGCCA GCACCGACAT CGGAACCCAA ACCGAAGAAA GGTAGGGCGA
AGTAGGGTGG CGTCGGCGGT CGTGGCTGTA GCCTTGGGTT TGGCTTCTTT CCATCCCGCT
       610        620        630        640        650        660
AAGATAAACC GAAGGGTAGA CCGAAAGACA AACCTCCGTG CGAACCGACG GTGAGTTCAC
TTCTATTTGG CTTCCCATCT GGCTTTCTGT TTGGAGGCAC GCTTGGCTGC CACTCAAGTG
       670        680        690        700        710        720
AACCACCGTC GCAGCCGACG GCAATGCCCG GCGGTCCGCC CGACGCGCCT CCCCCGCCA
TTGGTGGCAG CGTCGGCTGC CGTTACGGGC CGCCAGGCGG GCTGCGCGGA GGGGGCGGT
       730        740        750        760        770        780
TGCCCGCAGAT GCCACCCGGC GTGGCCGAGG CGGTACAAGC TGCCGTGCAG GCGGCCGTGG
ACGGCGTCTA CGGTGGGCCG CACCGGCTCC GCCATGTTCG ACGGCACGTC CGCCGGCACC
                                                 UL133
       790        800        810        820        830        840
CCGGCGGCTCT ACAACAACAG CAGCAGCATC AGACCGGAAC GTAA CCCGCC CCCGGTGCGA
GGCCGCCGAGA TGTTGTTGTC GTCGTCGTAG TCTGGCCTTG CATT GGGCGG GGGCCACGCT
                                                 UL135
       850        860        870        880        890        900
TAAGGAATTT TCCGACTTGG CGCACATCTC CTTCCTCAAT GTTTGGACAA TAAACACATT
ATTCCTTAAA AGGCTGAACC GCGTGTAGAG GAAGGAGTTA CAAACCTGTT ATTTGTGTAA
                                                          ATGTCCGTAC ACCGGCCCTT
       910        920        930        940        950        960
CCTTGCCAAA AAATGACGTT TCCAGAAATC CAAGGCATAA ATGTCCGTAC ACCGGCCCTT
GGAACGGTTT TTTACTGCAA AGGTCTTTAG GTTCCGTATT TACAGGCATG TGGCCGGGAA
```

```
     970        980        990       1000       1010       1020
CCCAACACGG AGTTTGAGAT TCCAAGCAGG AGAGAAGATC ATGGTGTGGA TATGGCTCGG
GGGTTGTGCC TCAAACTCTA AGGTTCGTCC TCTCTTCTAG TACCACACCT ATACCGAGCC 1030       1040       1050       1060       1070       1080
CATCGGGCTC CTCGGCGGTA CCGGACTGGC TTCCCTGGTC CTGGCCATTT CCTTATTTAC
GTAGCCCGAG GAGCCGCCAT GGCCTGACCG AAGGGACCAG GACCGGTAAA GGAATAAATG
                                              ▼UL134
    1090       1100       1110       1120       1130       1140
CCAGCGCCGA GGCCGCAAGC GATCCGACGA GACTTCGTCG CGAGGCCCGC TCCCGGGTGC
GGTCGCGGCT CCGGCGTTCG CTAGGCTGCT CTGAAGCAGC GCTCCGGGCG AGGGCCCACG 1150       1160       1170       1180       1190       1200
TGCTTCTGAT AAGCGTGGTG CCTGCGCGTG CTGCTATCGA AATCCGAAAG AAGACGTCGT
ACGAAGACTA TTCGCACCAC GGACGCGCAC GACGATAGCT TTAGGCTTTC TTCTGCAGCA 1210       1220       1230       1240       1250       1260
CGAGCCGCTG GATCTGGAAC TGGGGCTCAT GCGGGTGGAC ACCCACCCGC CGACGCCGCA
GCTCGGCGAC CTAGACCTTG ACCCCGAGTA CGCCCACCTG TGGGTGGGCG GCTGCGGCGT 1270       1280       1290       1300       1310       1320
GGTGCCGCGG TGTACGTCGC AGAGGATGGT CTGCCGATAG ATAAACCCGA CTGCCGATAG
CCACGGCGCC ACATGCAGCG TCTCCTACCA GACGGCTATC TATTTGGGCT GACGGCTATC 1330       1340       1350       1360       1370       1380
GCGCGGTTCG AGATCCCCGA CGTATCCACG CCGGGAAACG CGACCAGCAT CGACCAGCAT
CGCGCCAAGC TCTAGGGGCT GCATAGGTGC GGCCCTTGCG GCTGGTCGTA GCTGGTCGTA 1390       1400       1410       1420       1430       1440
GTTTCCTCCG CCGTCGCATT GCTCCTCGTC GAGCTCTTTG TCGTCCTCGA CCAGCGTCGA
CAAAGGAGGC GGCAGCGTAA CGAGGAGCAG CTCGAGAAAC AGCAGGAGCT GGTCGCAGCT
```

```
       1450       1460       1470       1480       1490       1500
CACGGTGCTG TATCAGCCGC CGCCATCCTG GAAGCCACCT CCGCCGCCCG GGCGCAAGAA
GTGCCACGAC ATAGTCGGCG GCGGTAGGAC CTTCGGTGGA GGCGGCGGGC CCGCGTTCTT 1510       1520       1530       1540       1550       1560
GCGGCCGCCT ACGCCGCCGG TCCGGGCCCC CACCACGCGG CTGTCGTCGC ACAGACCCCC
CGCCGGCGGA TGCGGCGGCC AGGCCCGGGG GTGGTGCGCC GACAGCAGCG TGTCTGGGGG 1570       1580       1590       1600       1610       1620
GACGCCGATA CCCGCGCCGC GTAAGAACCT GAGCACGCCG CCCACCAAGA AAACGCCGCC
CTGCGGCTAT GGGCGCGGCG CATTCTTGGA CTCGTGCGGC GGGTGGTTCT TTTGCGGCGG 1630       1640       1650       1660       1670       1680
GCCCACGAAA CCCAAGCCCG TCGGCTGGAC ACCGCCGGTG ACACCCAGGC CCTTCCCGAA
CGGGTGCTTT GGGTTCGGGC AGCCGACCTG TGGCGGCCAC TGTGGGTCCG GGAAGGGCTT 1690       1700       1710       1720       1730       1740
AACGCCGACG CCACAAAAGC CGCCGCGGAA TCCGAGACTA CCGGCACCCG TCGGTCTGGA
TTGCGGCTGC GGTGTTTTCG GCGGCGCCTT AGGCTCTGAT GGCCGTGGGC AGCCAGACCT 1750       1760       1770       1780       1790       1800
GAATCTCTCG AAGGTGGGAC TCTCGTGTCC CTGTCCCCGA CCCCGCACGC CGACGGAGCC
CTTAGAGAGC TTCCACCCTG AGAGCACAGG GACAGGGGCT GGGGCGTGCG GCTGCCTCGG 1810       1820       1830       1840       1850       1860
GACCACGCTG CCTATCGTGT CGGTTTCCGA GCTAGCCCCG CCTCCTCGAT GGTCGGACAT
CTGGTGCGAC GGATAGCACA GCCAAAGGCT CGATCGGGGC GGAGGAGCTA CCAGCCTGTA
```

| 1870 | 1880 | 1890 | 1900 | 1910 | 1920 |
|---|---|---|---|---|---|
| CGAGGAACTC | TTGGAACAGG | CGGTGCAGAG | CGTCATGAAG | GACGCCGAGT | CGATGCAGAT |
| GCTCCTTGAG | AACCTTGTCC | GCCACGTCTC | GCAGTACTTC | CTGCGGCTCA | GCTACGTCTA |

UL135 →

| 1930 | 1940 | 1950 | 1960 | 1970 | 1980 |
|---|---|---|---|---|---|
| GACCTGAGAC | CGAAAGAGCG | AGCGCGTCCG | TTGTACAGTT | GTATAGCAGC | ACACGCCTTC |
| CTGGACTCTG | GCTTTCTCGC | TCGCGCAGGC | AACATGTCAA | CATATCGTCG | TGTGCGGAAG |

| 1990 | 2000 | 2010 | 2020 UL136 → | 2030 | 2040 |
|---|---|---|---|---|---|
| CCTCTTTTTC | ACCGCAGCTA | AGAGAGAGAA | AGAGAGTATG | TCAGTCAAGG | GCGTGGAGAT |
| GGAGAAAAAG | TGGCGTCGAT | TCTCTCTCTT | TCTCTCATAC | AGTCAGTTCC | CGCACCTCTA |

| 2050 | 2060 | 2070 | 2080 | 2090 | 2100 |
|---|---|---|---|---|---|
| GCCAGAAATG | ACGTGGGACT | TGGACGTTAG | AAATAAATGG | CGGCGTCGAA | AGGCCCTGAG |
| CGGTCTTTAC | TGCACCCTGA | ACCTGCAATC | TTTATTTACC | GCCGCAGCTT | TCCGGGACTC |

| 2110 | 2120 | 2130 | 2140 | 2150 | 2160 |
|---|---|---|---|---|---|
| TCGCATTCAC | CGGTTCTGGG | AATGTCGGCT | ACGGGTGTGG | TGGCTGAGTG | ACGCCGGCGT |
| AGCGTAAGTG | GCCAAGACCC | TTACAGCCGA | TGCCCACACC | ACCGACTCAC | TGCGGCCGCA |

| 2170 | 2180 | 2190 | 2200 | 2210 | 2220 |
|---|---|---|---|---|---|
| AAGAGAAACC | GACCCACCGC | GTCCCCGACG | CCGCCCGACT | TGGATGACCG | CGGTGTTTCA |
| TTCTCTTTGG | CTGGGTGGCG | CAGGGGCTGC | GGCGGGCTGA | ACCTACTGGC | GCCACAAAGT |

| 2230 | 2240 | 2250 | 2260 | 2270 | 2280 |
|---|---|---|---|---|---|
| CGTTATCTGT | GCCGTTTTGC | TTACGCTTAT | GATTATGGCC | ATCGGCGCGC | TCATCGCGTA |
| GCAATAGACA | CGGCAAAACG | AATGCGAATA | CTAATACCGG | TAGCCGCGCG | AGTAGCGCAT |

| 2290 | 2300 | 2310 | 2320 | 2330 | 2340 |
|---|---|---|---|---|---|
| CTTAAGATAT | TACCACCAGG | ACAGTTGGCG | AGACATGCTC | CACGATCTAT | TTTGCGGCTG |
| GAATTCTATA | ATGGTGGTCC | TGTCAACCGC | TCTGTACGAG | GTGCTAGATA | AAACGCCGAC |

```
2350                2360                2370                2380                2390                2400
TCATTATCCC  GGATGTGCCC  GTCGGCACCA  CGAGCGGCAG  AGAAGGAGAC  GGCAAGCCAT
AGTAATAGGG  CTCTTCACGG  CAGCCGTGGT  GCTCGCCGTC  TCTTCCTCTG  CCGTTCGGTA 2410                2420                2430                2440                2450                2460
GGATGTGCCC  GACCCGGAAC  TCGGGCGACCC  GGCCCGCCGG  CCGTTGAACG  GAGCTATGTA
CCTACACGGG  CTGGGCCTTG  AGCCGCTGGG  CCGGGCGGCC  GGCAACTTGC  CTCGATACAT 2470                2480                2490                2500                2510                2520
CTACGGCAGC  GGCTGTCGCT  TCGACACGGT  GGAAATGGTG  GACGAGACGA  GACCCGCGCC
GATGCCGTCG  CCGACAGCGA  AGCTGTGCCA  CCTTTACCAC  CTGCTCTGCT  CTGGGCGCGG 2530                2540                2550                2560                2570                2580
GCCGGCGCTG  TCATCGCCCG  AAACCGGCGA  CGATAGCAAC  GACGACGCGG  TTGCCGGCGG
CGGCCGCGAC  AGTAGCGGGC  TTTGGCCGCT  GCTATCGTTG  CTGCTGCGCC  AACGGCCGCC 2590                2600                2610                2620                2630                2640
AGGTGCTGGC  GGGGTAACAT  CACCCGCGAC  TCGTACGACG  TCGCCGAACG  CACTGCTGCC
TCCACGACCG  CCCCATTGTA  GTGGGCGCTG  AGCATGCTGC  AGCGGCTTGC  GTGACGACGG
                         UL137

2650                2660                2670                2680                2690                2700
AGAATGGATG  GATGCGGTGC  ATGTGGCGGT  CCAAGCCGCC  GTTCAAGCGA  CCGTGCAAGT
TCTTACCTAC  CTACGCCACG  TACACCGCCA  GGTTCGGCGG  CAAGTTCGCT  GGCACGTTCA 2710                2720        UL136  2740                2750                2760
CGGGAGAACG  CCGTATCTCC  CGCTACGTAA  GAGGGTTGAG  GGGGCCGTTC
GCCCTCTTGC  GGCATAGAGG  GCGATGCATT  CTCCCAACTC  CCCCGGCAAG 2770                2780                2790                2800                2810                2820
AAGTGCCCCG  CGGGAGAACG  CCGTATCTCC  CGCTACGTAA  GAGGGTTGAG  GGGGCCGTTC
TTCACGGGGC  GCCCTCTTGC  GGCATAGAGG  GCGATGCATT  CTCCCAACTC  CCCCGGCAAG 2770                2780                2790                2800                2810                2820
CCGCGCGAGT  GCTGTACAAA  AGAGAGAGAC  TGGGACGTAG  ATCCGGACAG  AGGACGGTCA
GGCGCGCTCA  CGACATGTTT  TCTCTCTCTG  ACCCTGCATC  TAGGCCTGTC  TCCTGCCAGT
```

FIG._1C-2

```
UL138     2830       2840       2850       2860       2870       2880
      CCATGGACGA TCTGCCGCTG AATGTCGGGT TACCCATCAT CGGCGTGATG CTCGTGCTGA
      GGTACCTGCT AGACGGCGAC TTACAGCCCA ATGGGTAGTA GCCGCACTAC GAGCACGACT 2890       2900       2910       2920       2930       2940
      TCGTGGCCAT CCTCTGCTAT CTGGCTTACC ACTGGCACGA CACCTTCAAA CTGGTGCGCA
      AGCACCGGTA GGAGACGATA GACCGAATGG TGACCGTGCT GTGGAAGTTT GACCACGCGT
UL137

2950       2960       2970       2980       2990       3000
      TGTTTCTGAG CTACCGCTGG CTGATCCGCT GTTGCGAGCT GTACGGGGAG TACGAGCGCC
      ACAAAGACTC GATGGCGACC GACTAGGCGA CAACGCTCGA CATGCCCCTC ATGCTCGCGG 3010       3020       3030       3040       3050       3060
      GGTTCGCGGA CCTGTCGTCT CTGGGCCTCG GCGCCGTACG GCGGGAGTCG GACAGACGAT
      CCAAGCGCCT GGACAGCAGA GACCCGGAGC CGCGGCATGC CGCCCTCAGC CTGTCTGCTA 3070       3080       3090       3100       3110       3120
      ACCGTTTCTC CGAACGGCCC GACGAGATCT TGGTCCGTTG GGAGGAAGTG TCTTCCCAGT
      TGGCAAAGAG GCTTGCCGGG CTGCTCTAGA ACCAGGCAAC CCTCCTTCAC AGAAGGGTCA 3130       3140       3150       3160       3170       3180
      GCAGCTACGC GTCGTCGCGG ATAAACAGACC GCCGTGTGGG TTCATCGTCT TCGTCGTCGG
      CGTCGATGCG CAGCAGCGCC TATTGTCTGG CGGCACACCC AAGTAGCAGA AGCAGCAGCC 3190       3200       3210       3220       3230       3240
      TCCACGTCGC TAGCCAGAGA AACAGCGTGC CTCCGCCGGA CATGGCGGTG ACGGCGCCGC
      AGGTGCAGCG ATCGGTCTCT TTGTCGCACG GAGGCGGCCT GTACCGCCAC TGCCGCGGCG 3250       3260       3270       3280       3290       3300
      TCCACGTCGT CGATCTGTTG AAACCCGTGA CGGGATCCGC GACGCAGTTC ACCACCGTAG
      AGGTGCAGCA GCTAGACAAC TTTGGGCACT GCCCTAGGCG CTGCGTCAAG TGGTGGCATC
```

*FIG._1D-1*

```
     3310       3320       3330       3340       3350       3360
CCATGGTACA TTATCATCAA GAGTACACGT GAATGAGAAA AAGAAAAAAG AGGGGAGCGG
GGTACCATGT AATAGTAGTT CTCATGTGCA CTTACTCTTT TTCTTTTTTC TCCCCTCGCC
                                 └─UL138

3370       3380       3390       3400       3410       3420
ATCGCGATAA TGTCGCTTTG ACATTCTCTG CTCGATCTAC TCAGCGTCTG CACGAAACGG
TAGCGCTATT ACAGCGAAAC TGTAAGAGAC GAGCTAGATG AGTCGCAGAC GTGCTTTGCC 3430       3440       3450       3460       3470       3480
CATCCGCACG GAGGCGAGCC CAAGCGTATC TGCAGCAAGC GGTTCTTTCC CTCGGTGATG
GTAGGCGTGC CTCCGCTCGG GTTCGCATAG ACGTCGTTCG CCAAGAAAGG GAGCCACTAC 3490       3500       3510       3520       3530       3540
GTGGCAGCAT CGGTGGCGGG AGCTTGTTCG GACGATGGAC GGTGAGGAGT CCCTGGCGAT
CACCGTCGTA GCCACCGCCC TCGAACAAGC CTGCTACCTG CCACTCCTCA GGGACCGCTA 3550       3560       3570       3580       3590       3600
CAGGCGGCTC CCGGGTGTGG AGTTCAACGG GTGGTAATGG TGGCGGTGAT CGGTGTTAGA
GTCCGCCGAG GGCCCACACC TCAAGTTGCC CACCATTACC ACCGCCACTA GCCACAATCT 3610       3620       3630       3640       3650       3660
AAACGGTGGC CCTGGCAAAC ATATATCTAC TGTAAACCCT CTGCTCTGTT AATAAAAAGC
TTTGCCACCG GGACCGTTTG TATATAGATG ACATTTGGGA GACGAGACAA TTATTTTTCG 3670       3680       3690       3700       3710       3720
ACACTTTTCA CATGAGTTCG TAATTTTATT GTGTAGTGGA AATTTTTACG TCATTGGGAA
TGTGAAAAGT GTACTCAAGC ATTAAAATAA CACATCACCT TTAAAAATGC AGTAACCCTT 3730       3740       3750       3760       3770       3780
ACCCCAGAAT GAAAGAGTAT AATGTGCATA TCACCGGGGG TTCCCTGTCA GTACGAATGT
TGGGGTCTTA CTTTCTCATA TTACACGTAT AGTGGCCCCC AAGGGACAGT CATGCTTACA
```

FIG._1D-2

```
                     3790        3800        3810        3820        3830        3840
                ACACAACGCG  GGTTACATTA  CGATAAACTT  TCCGGTAAAA  CGATGCCGAT  ACAGCGTGTA
                TGTGTTGCGC  CCAATGTAAT  GCTATTTGAA  AGGCCATTTT  GCTACGGCTA  TGTCGCACAT 3850        3860        3870        3880        3890        3900↑
                TAACGCTGAT  TGTTACGACA  AACGAGTTGG  TATATCCATT  ATATAGTAAC  GAAC|ATGCTG|
                ATTGCGACTA  ACAATGCTGT  TTGCTCAACC  ATATAGGTAA  TATATCATTG  CTTG|TACGAC|
                                                                                 UL139

3910        3920        3930        3940        3950        3960
                TGGATATTAG  TTTTATTTGC  ACTCGCCGCA  TCGGCGAGTG  AAACCACTAC  AGGTACCAGC
                ACCTATAATC  AAAATAAACG  TGAGCGGCGT  AGCCGCTCAC  TTTGGTGATG  TCCATGGTCG 3970        3980        3990        4000        4010        4020
                TCTAATTCCA  GTCAATCTAC  TAGTGCTACC  GCCAACACGA  CCGTATCGAC  ATGTATTAAT
                AGATTAAGGT  CAGTTAGATG  ATCACGATGG  CGGTTGTGCT  GGCATAGCTG  TACATAATTA 4030        4040        4050        4060        4070        4080
                GCCTCTAACG  GCAGTAGCTG  GACAGTACCA  CAGCTCGCGC  TGCTTGCCGC  TAGCGGCTGG
                CGGAGATTGC  CGTCATCGAC  CTGTCATGGT  GTCGAGCGCG  ACGAACGGCG  ATCGCCGACC 4090        4100        4110        4120        4130        4140
                ACATTATCTG  GACTCCTTCT  CTTATTTACC  TGCTGCTTTT  GCTGCTTTTG  GCTAGTACGT
                TGTAATAGAC  CTGAGGAAGA  GAATAAATGG  ACGACGAAAA  CGACGAAAAC  CGATCATGCA 4150        4160        4170        4180        4190        4200
                AAAATCTGCA  GCTGCTGCGG  CAACTCCTCC  GAGTCAGAGA  GCAAAACAAC  CCACGCGTAC
                TTTTAGACGT  CGACGACGCC  GTTGAGGAGG  CTCAGTCTCT  CGTTTTGTTG  GGTGCGCATG 4210        4220        4230        4240        4250        4260
                ACCAATGCCG  CATTCACTTC  TTCCGACGCA  ACGTTACCCA  TGGGCCACTAC AGGGTCGTAC
                TGGTTACGGC  GTAAGTGAAG  AAGGCTGCGT  TGCAATGGGT  ACCCGTGATG  TCCCAGCATG
```

FIG._1E-1

```
                                                                                          4320
        4270          4280          4290          4300          4310        AAACCGAAAC
ACTCCCCCAC   AGGACGGCTC   ATTTCCACCT   CCGCCTCGGT   GACGTAGGCT   TTTGGCTTTG
TGAGGGGGTG   TCCTGCCGAG   TAAAGGTGGA   GGCGGAGCCA   CTGCATCCGA
                                                        UL139
                                                                                          4380
        4330          4340          4350          4360          4370        ATGACGTCCG
CCACGTTGAA   CCTAACGCGG   TTTCGGAAGG   CCTGAGACGT   CACTTTCACA   TACTGCAGGC
GGTGCAACTT   GGATTGCGCC   AAAGCCTTCC   GGACTCTGCA   GTGAAAGTGT 4390          4400          4410          4420          4430          4440
TATACACGTT   CATCATAAAA   CACCGTAGAG   GCTAAGGCTT   CGGTAGGGAG   AGACCTCAAC
ATATGTGCAA   GTAGTATTTT   GTGGCATCTC   CGATTCCGAA   GCCATCCCTC   TCTGGAGTTG

UL140 4490          4500
        4450          4460          4470          4480          GTCATGACCC   CCGCTCAGAC
TGTTCCTGAT   GAGCACCCGT   GCTCTCATCT   CTTCAGACTT   CAGTACTGGG   GGCGAGTCTG
ACAAGGACTA   CTCGTGGGCA   CGAGAGTAGA   GAAGTCTGAA 4510          4520          4530          4540          4550          4560
TAACGCGACT   ACCACCGTGC   ACCCGCACGA   CGCAAAAAAC   GGCAGCGGCG   GTAGTGCCCT
ATTGCGCTGA   TGGTGGCACG   TGGGCGTGCT   GCGTTTTTTG   CCGTCGCCGC   CATCACGGGA 4570          4580          4590          4600          4610          4620
GCCGACCCTC   GTCGTTTTCG   GCTTTATCGT   TACGCTACTT   TTCTTTCTCT   TTATGCTCTA
CGGCTGGGAG   CAGCAAAAGC   CGAAATAGCA   ATGCGATGAA   AAGAAAGAGA   AATACGAGAT 4630          4640          4650          4660          4670          4680
CTTTTGGAAC   AACGACGTGT   TCCGTAAGCT   GCTCCGTGCG   CTTGGATCCA   GGCGTGTTGC
GAAAACCTTG   TTGCTGCACA   AGGCATTCGA   CGAGGCACGC   GAACCTAGGT   CGCGACAACG 4690          4700          4710          4720          4730          4740
GACCGCTTCG   ACGCGTGGCA   AGACGAGGTC   ATCTACCGTC   GTCCATCACG   TCGTTCCCAG
CTGGCGAAGC   TGCGCACCGT   TCTGCTCCAG   TAGATGGCAG   CAGTAGTGC   AGCAAGGGTC
```

FIG._1E-2

FIG._1F-1

```
5230       5240       5250       5260       5270       5280
TCAGTTGCGG GCATCCCGGG CGAGAAGCTG CGTCGCACGG TGGTCACCAC CACGCCGGCC
AGTCAACGCC CGTAGGGCCC GCTCTTCGAC GCAGCGTGCC ACCAGTGGTG GTGCGGCCGG 5290       5300       5310       5320       5330       5340
CGACGTTTGA GCGGCCGACA CACGGAGCAG GAGCAGGCGG GCATGCGTCT CTGTGAAAAA
GCTGCAAACT CGCCGGCTGT GTGCCTCGTC CTCGTCCGCC CGTACGCAGA GACACTTTTT 5350       5360       5370       5380       5390       5400
GGGAAGAAAA GAATCATCAT GTGCCGCCGG GAGTCGCTCC GAACTCTGCC GTGGCTGTTC
CCCTTCTTTT CTTAGTAGTA CACGGCGGCC CTCAGCGAGG CTTGAGACGG CACCGACAAG 5410       5420       5430       5440       5450       5460
TGGGTGCTGT TGAGCTGCCC GCGACTCCTC GAATATTCTT CCTCTTCGTT CCCCTTCGCC
ACCCACGACA ACTCGACGGG CGCTGAGGAG CTTATAAGAA GGAGAAGCAA GGGGAAGCGG 5470       5480       5490       5500       5510       5520
ACCGCTGACA TTGCCGAAAA GATGTGGGCC GAGAATTATG AGACCACGTC GCCGGCGCCG
TGGCGACTGT AACGGCTTTT CTACACCCGG CTCTTAATAC TCTGGTGCAG CGGCCGCGGC 5530       5540       5550       5560       5570       5580
GTGTTGGTCG CCGAGGGAGA GCAAGTTACC ATCCCCTGCA CGGTCATGAC ACACTCCTGG
CACAACCAGC GGCTCCCTCT CGTTCAATGG TAGGGGACGT GCCAGTACTG TGTGAGGACC 5590       5600       5610       5620       5630       5640
CCCATGGTCT CCATTCGCGC ACGTTTCTGT CGTTCCCACG ACGGCAGCGA CGAGCTCATC
GGGTACCAGA GGTAAGCGCG TGCAAAGACA GCAAGGGTGC TGCCGTCGCT GCTCGAGTAG
```

*FIG._1F-2*

```
5650       5660       5670       5680       5690       5700
CTGGACGCCG TCAAAGGCCA TCGGCTGATG AACGGACTCC AGTACCGCCT GCCGTACGCC
GACCTGCGGC AGTTTCCGGT AGCCGACTAC TTGCCTGAGG TCATGGCGGA CGGCATGCGG 5710       5720       5730       5740       5750       5760
ACTTGGAATT TCTCGCAATT GCATCTCGGC CAAATATTCT CGCTTACTTT TAACGTATCG
TGAACCTTAA AGAGCGTTAA CGTAGAGCCG GTTTATAAGA GCGAATGAAA ATTGCATAGC 5770       5780       5790       5800       5810       5820
ATGGACACAG CCGGCATGTA CGAATGCGTG CTACGCAACT ACAGCCACGG CCTCATCATG
TACCTGTGTC GGCCGTACAT GCTTACGCAC GATGCGTTGA TGTCGGTGCC GGAGTAGTAC 5830       5840       5850       5860       5870       5880
CAACGCTTCG TAATTCTCAC GCAGCTGGAG ACGCTCAGCC GGCCCGACGA ACCTTGCTGC
GTTGCGAAGC ATTAAGAGTG CGTCGACCTC TGCGAGTCGG CCGGGCTGCT TGGAACGACG 5890       5900       5910       5920       5930       5940
ACACCGGCGT TAGGTCGCTA CTCGCTGGGA GACCAGATCT GGTCGCCGAC GCCCTGGCGT
TGTGGCCGCA ATCCAGCGAT GAGCGACCCT CTGGTCTAGA CCAGCGGCTG CGGGACCGCA 5950       5960       5970       5980       5990       6000
CTACGGAATC ACGACTGCGG AACGTACCGC GGCTTTCAAC GCAACTACTT CTATATCGGC
GATGCCTTAG TGCTGACGCC TTGCATGGCG CCGAAAGTTG CGTTGATGAA GATATAGCCG 6010       6020       6030       6040       6050       6060
CGCGCCGACG CCGAGGATTG CTGGAAACCC GCATGTCCGG ACGAGGAACC CGACCGCTGT
GCGCGGCTGC GGCTCCTAAC GACCTTTGGG CGTACAGGCC TGCTCCTTGG GCTGGCGACA 6070       6080       6090       6100       6110       6120
TGGACAGTGA TACAGCGTTA CCGGCTCCCC GGCGACTGCT ACCGTTCGCA GCCACACCCG
ACCTGTCACT ATGTCGCAAT GGCCGAGGGG CCGCTGACGA TGGCAAGCGT CGGTGTGGGC
```

*FIG._1G-1*

```
         6130            6140            6150            6160            6170            6180
CCGAAATTTT TACCGGTGAC GCCAGCACCG CCGGCCGACA TAGACACCGG GATGTCTCCC
GGCTTTAAAA ATGGCCACTG CGGTCGTGGC GGCCGGCTGT ATCTGTGGCC CTACAGAGGG 6190            6200            6210            6220            6230            6240
TGGGCCACTC GGGGAATCGC GGCGTTTTTG GGGTTTTGGA GTATTTTTAC CGTATGTTTC
ACCCGGTGAG CCCCTTAGCG CCGCAAAAAC CCCAAAACCT CATAAAAATG GCATACAAAG 6250            6260            6270            6280            6290            6300
CTATGCTACC TGTGTTATCT GCAGTGTTGT GGACGCTGGT GTCCCACGCC GGGAAGGGGA
GATACGATGG ACACAATAGA CGTCACAACA CCTGCGACCA CAGGGTGCGG CCCTTCCCCT 6310            6320            6330            6340            6350            6360
CGACGAGGCG GTGAGGGCTA TCGACGCCTA CCGACTTACG ATAGTTACCC CGGTGTTAGA
GCTGCTCCGC CACTCCCGAT AGCTGCGGAT GGCTGAATGC TATCAATGGG GCCACAATCT

UL141 6370            6380            6390            6400            6410            6420
AAGATGAAGA GGTGAGAACA CGTATAAAAT AAAAAAATAA TATGTTAAAA AATGCAGTGT
TTCTACTTCT CCACTCTTGT GCATATTTTA TTTTTTTATT ATACAATTTT TTACGTCACA 6430            6440      UL142 6450            6460            6470            6480
GTGAAGTGTG AATAGTGTGA TTAAAATATG CGGATTGAAT GGGTGTGGTG GTTATTCGGA
CACTTCACAC TTATCACACT AATTTTATAC GCCTAACTTA CCCACACCAC CAATAAGCCT 6490            6500            6510            6520            6530            6540
TACTTTGTGT CATCCGTTGG GAGCGAACGG TCATTATCCT ATCGTTACCA CTTGGAATCT
ATGAAACACA GTAGGCAACC CTCGCTTGCC AGTAATAGGA TAGCAATGGT GAACCTTAGA 6550            6560            6570            6580            6590            6600
AATTCATCTA CCAACGTGGT TTGCAACGGA AACATTTCCG TGTTTGTAAA CGGCACCCTA
TTAAGTAGAT GGTTGCACCA AACGTTGCCT TTGTAAAGGC ACAAACATTT GCCGTGGGAT
```

```
        6610                 6620       6630       6640       6650       6660
GGTGTGCGGT   ATAACATTAC   GGTAGGAATC   AGTTCGTCTT   TATTAATAGG   ACACCCTTACT
CCACACGCCA   TATTGTAATG   CCATCCTTAG   TCAAGCAGAA   ATAATTATCC   TGTGGAATGA 6670                 6680       6690       6700       6710       6720
ATACAAGTAT   TGGAATCATG   GTTCACACCC   TGGGTCCAAA   ATAAAAGTTA   CAACAAACAA
TATGTTCATA   ACCTTAGTAC   CAAGTGTGGG   ACCCAGGTTT   TATTTTCAAT   GTTGTTTGTT 6730                 6740       6750       6760       6770       6780
CCCCTAGGTG   ACACTGAAAC   GCTTTATAAT   ATAGATAGCG   AAAACATTCA   TCGCGTATCT
GGGGATCCAC   TGTGACTTTG   CGAAATATTA   TATCTATCGC   TTTTGTAAGT   AGCGCATAGA 6790                 6800       6810       6820       6830       6840
CAATATTTTC   ACACAAGATG   GATAAAATCT   CTGCAAGAGA   ATCACACTTG   CGACCTCACA
GTTATAAAAG   TGTGTTCTAC   CTATTTTAGA   GACGTTCTCT   TAGTGTGAAC   GCTGGAGTGT 6850                 6860       6870       6880       6890       6900
AACAGTACAC   CTACCTATAC   ATATCAAGTA   AACGTGAACA   ACACGAATTA   CCTAACACTA
TTGTCATGTG   GATGGATATG   TATAGTTCAT   TTGCACTTGT   TGTGCTTAAT   GGATTGTGAT 6910                 6920       6930       6940       6950       6960
ACATCCTCGG   GATGGCAAGA   CCGTCTAAAT   TACACCGTCA   TAAATAGTAC   ACACTTTAAC
TGTAGGAGCC   CTACCGTTCT   GGCAGATTTA   ATGTGGCAGT   ATTTATCATG   TGTGAAATTG 6970                 6980       6990       7000       7010       7020
CTCACAGAAT   CGAACATAAC   CAGCATTCAA   AAATATCTCA   ACACTACCTG   CATAGAAAGA
GAGTGTCTTA   GCTTGTATTG   GTCGTAAGTT   TTTATAGAGT   TGTGATGGAC   GTATCTTTCT 7030                 7040       7050       7060       7070       7080
CTCCGTAACT   ACACCTTGGA   GTCCGTATAC   ACCACAACTG   TGCCTCAAAA   CATAACAACA
GAGGCATTGA   TGTGGAACCT   CAGGCATATG   TGGTGTTGAC   ACGGAGTTTT   GTATTGTTGT
```

FIG._1H-1

```
7090       7100       7110       7120       7130       7140
TCTCAACACG CAACAACCAC TATGCACACA ATACCTCCAA ATACAATAAC AATTCAAAAT
AGAGTTGTGC GTTGTTGGTG ATACGTGTGT TATGGAGGTT TATGTTATTG TTAAGTTTTA 7150       7160       7170       7180       7190       7200
ACAACTCAAA GCCATACTGT ACAGACGCCG TCTTTTAACG ACACACATAA CGTGACGAAA
TGTTGAGTTT CGGTATGACA TGTCTGCGGC AGAAAATTGC TGTGTGTATT GCACTGCTTT 7210       7220       7230       7240       7250       7260
CACACGTTAA ACATAAGCTA CGTTTTATCA CAAAAAACGA ATAACACAAC ATCACCGTGG
GTGTGCAATT TGTATTCGAT GCAAAATAGT GTTTTTTGCT TATTGTGTTG TAGTGGCACC 7270       7280       7290       7300       7310       7320
ATATATGCCA TACCTATGGG CGCTACAGCC ACAATAGGCG CCGGTTTATA TATCGGGAAA
TATATACGGT ATGGATACCC GCGATGTCGG TGTTATCCGC GGCCAAATAT ATAGCCCTTT 7330       7340       7350         UL143 7360   UL142 7370  7380
CACTTTACGC CGGTTAAGTT CGTATACGAG GTATGGCGCG GTCAGTAAAG ACGATTCGGA
GTGAAATGCG GCCAATTCAA GCATATGCTC CATACCGCGC CAGTCATTTC TGCTAAGCCT 7390       7400       7410       7420       7430       7440
TTCAACACAT ATACTCCCCA CGATCCTCGA ACACCTTACA GCATATGAGC AAAAAACAAG
AAGTTGTGTA TATGAGGGGT GCTAGGAGCT TGTGGAATGT CGTATACTCG TTTTTTGTTC 7450       7460       7470       7480       7490       7500
AAAGTATAGC CACAATCACA TTTGGGCGAA TAACATGCTG TCATCCACTA GCGTCTATTA
TTTCATATCG GTGTTAGTGT AAACCCGCTT ATTGTACGAC AGTAGGTGAT CGCAGATAAT 7510       7520       7530       7540       7550       7560
ATCTAATGTT TAACGGGAGC TGTACTGTCA CCGTTAAAAT ATCCATGGGA ATCAACGGGT
TAGATTACAA ATTGCCCTCG ACATGACAGT GGCAATTTTA TAGGTACCCT TAGTTGCCCA
```

FIG._1H-2

```
                7570       7580       7590       7600       7610       7620
           CAACCAACGT CCATCAGCTT GTGATTGTGC TCCATCTGGG TAACCGCTGT CAGCCTTGGC
           GTTGGTTGCA GGTAGTCGAA CACTAACACG AGGTAGACCC ATTGGCGACA GTCGGAACCG

UL143  7630       7640       7650       7660       7670       7680
           GACAGGTGTA ATCACAGCTG TCACATAACT CACGAAGCCT CCAATCACAG CAGCACACAT
           CTGTCCACAT TAGTGTCGAC AGTGTATTGA GTGCTTCGGA GGTTAGTGTC GTCGTGTGTA 7690       7700       7710       7720       7730       7740
           AGTCCTAACG CCATTGGCGT GTATAAAAGT TCGGAAAACT TGACGGTTGT ACGGCACGAC
           TCAGGATTGC GGTAACCGCA CATATTTTCA AGCCTTTTGA ACTGCCAACA TGCCGTGCTG 7750       7760       7770       7780       7790       7800
           AAATCGATGT AGTGGTATGT TTTTCCAGCA GAGACCGTGT GCGGTCTCTT AGGTTCGCTA
           TTTAGCTACA TCACCATACA AAAAGGTCGT CTCTGGCACA CGCCAGAGAA TCCAAGCGAT 7810       7820       7830       7840       7850       7860
           TACTGTGGCT GGAAACTGGT TACCTGTAGT GATGGCTAAC TATCCTGTTC TGTCCTGGAA
           ATGACACCGA CCTTTGACCA ATGGACACTT CTACCGATTG ATAGGACAAG ACAGGACCTT 7870       7880       7890       7900       7910       7920
           AAACTTTTGG CGTCGTAGGT TTACAAACCG GGACTTTGCA GTATGCGGGT ATGTCATTTA
           TTTGAAAACC GCAGCATCCA AATGTTTGGC CCTGAAACGT CATACGCCCA TACAGTAAAT 7930       7940       7950       7960       7970       7980
           TTTACGTTTA CGATCTCGTA TTACAAACCG CGGAGAGGAT GATACCGTTC GGCCCCATGA
           AAATGCAAAT GCTAGAGCAT AATGTTTGGC GCCTCTCCTA CTATGGCAAG CCGGGGTACT 7990       8000     8010 UL144  8020       8030       8040
           GTTATTTTTA TTCTTCCGGT AGGAGGCATG AAGCCCTCTGA TAATGCTCAT CTGCTTTGCT
           CAATAAAAAT AAGAAGGCCA TCCTCCGTAC TTCGGAGACT ATTACGAGTA GACGAAACGA
```

FIG._1I-1

```
                                                              8100
                             8070      8080      8090
      8050      8060
GTGATATTAT TGCAGCTTGG AGTGACTAAA GTGTGTCAGC ATAATGAAGT GCAACTGGGC
CACTATAATA ACGTCGAACC TCACTGATTT CACACAGTCG TATTACTTCA CGTTGACCCG 8160
                             8130      8140      8150
      8110      8120
AATGAGTGCT GCCCTCCGTG TGGTTCGGGA CAAAGAGTTA CTAAAGTATG CACGGATTAT
TTACTCACGA CGGGAGGCAC ACCAAGCCCT GTTTCTCAAT GATTTCATAC GTGCCTAATA 8220
                             8190      8200      8210
      8170      8180
ACCAGTGTAA CGTGTACCCC TTGCCCCAAC GGCACGTATG TATCGGGACT TTACAACTGT
TGGTCACATT GCACATGGGG AACGGGGTTG CCGTGCATAC ATAGCCCTGA AATGTTGACA 8280
                             8250      8260      8270
      8230      8240
ACCGATTGCA CTCAATGTAA CGTCACTCAG GTCATGATTC GTAACTGCAC TTCCACCAAT
TGGCTAACGT GAGTTACATT GCAGTGAGTC CAGTACTAAG CATTGACGTG AAGGTGGTTA 8340
                             8310      8320      8330
      8290      8300
AATACCGTAT GCGCACCTAA GAACCATACG TACTTTTCCA CTCCAGGCGT CCAACATCAC
TTATGGCATA CGCGTGGATT CTTGGTATGC ATGAAAAGGT GAGGTCCGCA GGTTGTAGTG 8400
                             8370      8380      8390
      8350      8360
AAACAACGAC AGCAAAAATCA TACCGCACAT ATAACCGTCA AACAAGGAAA AAGCGGTCGT
TTTGTTGCTG TCGTTTTAGT ATGGCGTGTA TATTGGCAGT TTGTTCCTTT TTCGCCAGCA 8460
                             8430      8440      8450
      8410      8420
CATACTCTAG CCTGGTTGTC TCTCTTTATC TTTCTTGTGG GTATCATACT TTTAATTCTC
GTATGAGATC GGACCAACAG AGAGAAATAG AAAGAACACC CATAGTATGA AAATTAAGAG 8520
                             8490      8500      8510
      8470      8480
TATCTTATAG CCGCCTATCG GAGTGAGAGA TGCCAACAGT GTTGCTCAAT CGGCAAAATT
ATAGAATATC GGCGGATAGC CTCACTCTCT ACGGTTGTCA CAACGAGTTA GCCGTTTTAA
```

*FIG._1I-2*

```
            UL144
        8530       8540       8550       8560       8570       8580
   TTCTACCGCA CCCTGTAAGC TTCCTGTTGT TGTTTTTACA TCACGGTACG ATGAAGTCAC
   AAGATGGCGT GGGACATTCG AAGGACAACA ACAAAAATGT AGTGCCATGC TACTTCAGTG 8590       8600       8610       8620       8630       8640
   ACAGATAATT ACAGATGAGC TGTTCATATT TTTTATTATT TTTTCCAATT CCTGCACTAA
   TGTCTATTAA TGTCTACTCG ACAAGTATAA AAAATAATAA AAAAGGTTAA GGACGTGATT 8650       8660       8670       8680       8690       8700
   AAAAAGAAGC ACTTTACGGA ACCGTGTCTG AGTATCTGTG GGGAATTTAG GTACTTTTTG
   TTTTTCTTCG TGAAATGCCT TGGCACAGAC TCATAGACAC CCCTTAAATC CATGAAAAAC 8710       8720       8730       8740       8750       8760
   CCGACGTCAG GAAAAATAAG TGTCGCCTAC ATAAGAGCCC GGTGCTATCG TGCTGTCACT
   GGCTGCAGTC CTTTTTATTC ACAGCGGATG TATTCTCGGG CCACGATAGC ACGACAGTGA 8770       8780       8790       8800       8810       8820
   CTTTCTTGTT GCCTTCGATG TGGCTCATTA CTACTCCTTC ATCAGTAGCC
   GAAAGAACAA CGGAAGCTAC ACCGAGTAAT GATGAGGAAG TAGTCATCGG

UL145
        8830       8840       8850       8860       8870       8880
   CCAGCGTTAT GGTTAATTTT AAGCATCATA ACGCCGTGCA GCTGTTATGT GCACGGACCC
   GGTCGCAATA CCAATTAAAA TTCGTAGTAT TGCGGCACGT CGACAATACA CGTGCCTGGG 8890       8900       8910       8920       8930       8940
   GAGACGCACT GCCGGATGGG AACGTTTAAC CCATCATGCG TCGTATCACG CGAACTACGG
   CTCTGCGTGA CGGCCTACCC TTGCAAATTG GGTAGTACGC AGCATAGTGC GCTTGATGCC 8950       8960       8970       8980       8990       9000
   GGCATACGCC GTGTTGATGG CTACATCGCA AAGAAAGTCC CTAGTGTTAC ATCGATACAG
   CCGTATGCGG CACAACTACC GATGTAGCGT TTCTTTCAGG GATCACAATG TAGCTATGTC
```

FIG._1J-1

```
      9010       9020       9030       9040       9050       9060
TGCCGTGACA GCCGTGGCCC TGCAGCTCAT GCCTGTTGAG ATCGTCCGCA AGCTAGATCA
ACGGCACTGT CGGCACCGGG ACGTCGAGTA CGGACAACTC TAGCAGGCGT TCGATCTAGT 9070       9080       9090       9100       9110       9120
GTCGGACTGG GTGCGGGGTG CCTGGATCGT GTCAGAGACT TTTCCAACTA GCGACCCCAA
CAGCCTGACC CACGCCCCAC GGACCTAGCA CAGTCTCTGA AAAGGTTGAT CGCTGGGGTT 9130       9140       9150   UL145 9170       9180
AGGAGTTTGG AGCGACGATG ACTCCTCGAT GGGTGGAAGT GATGATTGAT GATGAGAACC
TCCTCAAACC TCGCTGCTAC TGAGGAGCTA CCCACCTTCA CTACTAACTA CTACTCTTGG 9190       9200       9210       9220       9230       9240
TGACAAGAAA GACGAGAGAG AAATTTAGAG CTGTCATTGT AGAATTAGTC TAGATTCCTG
ACTGTTCTTT CTGCTCTCTC TTTAAATCTC GACAGTAACA TCTTAATCAG ATCTAAGGAC 9250       9260       9270       9280       9290       9300
ATAATAAACA GTATCGATTT TGAAACCTAA TTGACGTGTG ATCGATTTTT AAACCTCTGT
TATTATTTGT CATAGCTAAA ACTTTGGATT AACTGCACAC TAGCTAAAAA TTTGGAGACA 9310       9320       9330       9340       9350       9360
GTTGTGTGAT TGATTGGTAT GTGGGGGAT CCGATTTCAA AGGGGGGTAC TTATCGGGAA
CAACACACTA ACTAACCATA CACCCCCCTA GGCTAAAGTT TCCCCCCATG AATAGCCCTT 9370       9380       9390       9400       9410       9420
TTGATGTGTC ATGGACGCAG TTTTCCGGGA TTTTGAGCGA ATACCGGATA TTACGAATTA
AACTACACAG TACCTGCGTC AAAAGGCCCT AAAACTCGCT TATGGCCTAT AATGCTTAAT
```

*FIG._1J-2*

```
         9430        9440        9450  UL146 9460        9470        9480
    CTGGTAGTGA  CGTAGATAAT  AAAATTATAA  TGCGATTAAT  TTTTGGTGCG  TTGATTATTT
    GACCATCACT  GCATCTATTA  TTTTAATATT  ACGCTAATTA  AAAACCACGC  AACTAATAAA 9490        9500        9510        9520        9530        9540
    TTTTAGCATA  TGTGTATCAT  TATGAGGTGA  ATGGAACAGA  ATTACGCTGC  AGATGTCTTC
    AAAATCGTAT  ACACATAGTA  ATACTCCACT  TACCTTGTCT  TAATGCGACG  TCTACAGAAG 9550        9560        9570        9580        9590        9600
    ATAGAAAATG  GCCGCCTAAT  AAAATTATAT  TGGGTAATTA  TTGGCTTCAT  CGCGATCCCA
    TATCTTTTAC  CGGCGGATTA  TTTTAATATA  ACCCATTAAT  AACCGAAGTA  GCGCTAGGGT 9610        9620        9630        9640        9650        9660
    GAGGGCCCGG  ATGCGATAAA  AATGAACATT  TATTGTATCC  AGACGGAAGG  AAACCGCCTG
    CTCCCGGGCC  TACGCTATTT  TTACTTGTAA  ATAACATAGG  TCTGCCTTCC  TTTGGCGGAC 9670        9680        9690        9700        9710        9720
    GACCTGGAGT  ATGTTTATCG  CCCGATCACC  TCTTCTCAAA  ATGGTTAGAC  AAACACAACG
    CTGGACCTCA  TACAAATAGC  GGGCTAGTGG  AGAAGAGTTT  TACCAATCTG  TTTGTGTTGC 9730        9740        9750        9760        9770        9780
    ATAATAGGTG  GTATAATGTT  AACATAACGA  AATCACCAGG  ACCGAGACGA  ATAAATATAA
    TATTATCCAC  CATATTACAA  TTGTATTGCT  TTAGTGGTCC  TGGCTCTGCT  TATTTATATT

9790 UL146 9800  UL146 9810        9820        9830        9840
    CCTTGATAGG  TGTTAGAGGA  TAATATTTAA  TGTATGTTTT  CAAACAGACA  AGTTCGTTAA
    GGAACTATCC  ACAATCTCCT  ATTATAAATT  ACATACAAAA  GTTTGTCTGT  TCAAGCAATT 9850        9860        9870 UL147 9880        9890        9900
    AACAAAATAT  TACAGTATGT  GTTTAATAATG  GTGCTAACAT  GGTTGCACCA  TCCGGTTTCA
    TTGTTTTATA  ATGTCATACA  CAAATTATAC  CACGATTGTA  CCAACGTGGT  AGGCCAAAGT
```

*FIG. 1K-1*

```
       9910                9920                9930                9940                9950                9960
AACTCGCATA          TCAATCTGTT          ATCGGTACGA          CACCTGTCAT          TAATCGCATA          TATGTTACTT
TTGAGCGTAT          AGTTAGACAA          TAGCCATGCT          GTGGACAGTA          ATTAGCGTAT          ATACAATGAA 9970                9980                9990               10000               10010               10020
ACCATATGTC          CCCTAGCCGT          CCATGTTTTA          GAACTAGAAG          ATTACGACAG          GCGCTGCCGT
TGGTATACAG          GGGATCGGCA          GGTACAAAAT          CTTGATCTTC          TAATGCTGTC          CGCGACGGCA 10030               10040               10050               10060               10070               10080
TGCAACAACC          AAATTCTGTT          GAATACCCTG          CCGGTCGGAA          ATTACGTTGCT         TAAGCCAATC
ACGTTGTTGG          TTTAAGACAA          CTTATGGGAC          GGCCAGCCTT          TAATGCAACGA         ATTCGGTTAG 10090               10100               10110               10120               10130               10140
GCAGCGAGCG          AAAGCTGCAA          TCGTCAGGAA          GTGCTGGCTA          TTTTAAAGGA          CAAGGAACC
CGTCGCTCGC          TTTCGACGTT          AGCAGTCCTT          CACGACCGAT          AAAATTTCCT          GTTCCCTTGG 10150               10160               10170               10180               10190               10200
AAGTGTCTCA          ATCCTAACGC          GCAAGCCGTG          CGTCGTCACA          TCAACCGGCT          ATTTTTTCGG
TTCACAGAGT          TAGGATTGCG          CGTTCGGCAC          GCAGCAGTGT          AGTTGGCCGA          TAAAAAAGCC 10210               10220               10230               10240               10250               10260
TTAATCTTAG          ACGAGGAACA          ACGCATTTAC          GACGTAGTGT          CTACCAATAT          TGAGTTCGGT
AATTAGAATC          TGCTCCTTGT          TGCGTAAATG          CTGCATCACA          GATGGTTATA          ACTCAAGCCA 10270               10280               10290               10300               10310               10320
GCCTGGCCAG          TCCCTACGGC          CTACAAAGCC          TTTCTTTTGA          AATACGCCAA          GAGACTGAAC
CGGACCGGTC          AGGGATGCCG          GATGTTTCGG          AAAGAAACCT          TTATGCGGTT          CTCTGACTTG 10330               10340             UL147 10350            10360               10370               10380
TACCACCACT          TCAGACTGCG          CTGGTGATCA          TGTCCCTATT          TTACCGTGCG          GTAGCTCTGG
ATGGTGGTGA          AGTCTGACGC          GACCACTAGT          ACAGGGATAA          AATGGCACGC          CATCGAGACC
```

FIG._1K-2

```
10390       10400       10410       10420       10430       10440
GCACGCTAAG  CGCTTTGGTG  TGGTACAGCA  CTAGCCATCCT CGCAGAGATT  AACGAAAATT
CGTGCGATTC  GCGAAACCAC  ACCATGTCGT  GATCGTAGGA  GCGTCTCTAA  TTGCTTTTAA 10450       10460       10470       10480       10490       10500
CCTGCTCCTC  ATCTTCTGCG  GATCACGAAG  ACTGGCGAGGA ACCGGACGAG  ATCGTTCGCG
GGACGAGGAG  TAGAAGACGC  CTAGTGCTTC  TGACGCTCCT  TGGCCTGCTC  TAGCAAGCGC 10510       10520       10530       10540       10550       10560
AAGAGCAAGA  CTATCGGGCT  CTGGCTGGCCT TTTCCCTAGT  GATTTGCGGT  ACGCTCCTCG
TTCTCGTTCT  GATAGCCCGA  GACGACCGGA  AAAGGGATCA  CTAAACGCCA  TGCGAGGAGC 10570       10580       10590       10600       10610       10620
TCACTTGTGT  GATCTGAGAC  GTCATGCTGG  TAGCGTTTAT  GAGTCGGGCG  GTGGCCGACA
AGTGAACACA  CTAGACTCTG  CAGTACGACC  ATCGCAAATA  CTCAGCCCGC  CACCGGCTGT 10640                  10650 UL148 10660       10670       10680
10630       CCTAACCCGC  GCAGCATGTT  GCGCTTGCTG   TTCACGCTCG  TCCTGCTGGC
CGCCGCATTT  GGATTGGGCG  CGTCGTACAA   CGCGAACGAC  AAGTGCGAGC  AGGACGACCG
GCGGGCGTAAA 10690       10700       10710       10720       10730       10740
CCTCCACGGG  CAGTCTGTCG  GCGCTAGCCG  CGACTATGTG  CATGTTCGGC  TACTGAGCTA
GGAGGTGCCC  GTCAGACAGC  CGCGATCGGC  GCTGATACAC  GTACAAGCCG  ATGACTCGAT 10750       10760       10770       10780       10790       10800
CCGAGGCGAC  CCCCTGGTCT  TCAAGCACAC  TTTCTCGGGT  GTGGCGTCGAC CCTTCACCGA
GGCTCCGCTG  GGGGACCAGA  AGTTCGTGTG  AAAGAGCCCA  CACGCAGCTG  GGAAGTGGCT 10810       10820       10830       10840       10850       10860
GCTAGGCTGG  GCTGCGTGTC  GCGACTGGGA  CAGTATGCAT  TGCACACCCT  TCTGGTCTAC
CGATCCGACC  CGACGCACAG  CGCTGACCCT  GTCATACGTA  ACGTGTGGGA  AGACCAGATG
```

FIG._1L-1

```
     10870      10880      10890      10900      10910      10920
CGATCTGGAG CAGATGACCG ACTCGGTGCG GCGTTACAGC ACGGTGAGCC CCGGCAAGGA
GCTAGACCTC GTCTACTGGC TGAGCCACGC CGCAATGTCG TGCCACTCGG GGCCGTTCCT 10930      10940      10950      10960      10970      10980
AGTGACGCTT CAGCTTCACG GGAACCAAAC CGTACAGCCG TCGTTTCTAA GCTTTACGTG
TCACTGCGAA GTCGAAGTGC CCTTGGTTTG GCATGTCGGC AGCAAAGATT CGAAATGCAC 10990      11000      11010      11020      11030      11040
CCGCCTGCAG CTAGAACCCG TGGTGGAAAA TGTTGGCCTC TACGTGGCCT ACGTGGTCAA
GGCGGACGTC GATCTTGGGC ACCACCTTTT ACAACCGGAG ATGCACCGGA TGCACCAGTT 11050      11060      11070      11080      11090      11100
CGACGGCGAA CGCCCACAAC AGTTTTTTAC ACCGCAGGTA GACGTGGTAC GCTTTGCTCT
GCTGCCGCTT GCGGGTGTTG TCAAAAAATG TGGCGTCCAT CTGCACCATG CGAAACGAGA 11110      11120      11130      11140      11150      11160
ATATCTAGAA ACACTCTCCC GGATCGTGGA ACCGTTAGAA TCAGGTCGCC TGGCAGTGGA
TATAGATCTT TGTGAGAGGG CCTAGCACCT TGGCAATCTT AGTCCAGCGG ACCGTCACCT 11170      11180      11190      11200      11210      11220
ATTTGATACG CCTGACCTAG CTCTGGCGCC CGATTTAGTA AGCAGCCTCT TCGTGGCCGG
TAAACTATGC GGACTGGATC GAGACCGCGG GCTAAATCAT TCGTCGGAGA AGCACCGGCC 11230      11240      11250      11260      11270      11280
ACACGGCGAG ACCGACTTTT ACATGAACTG GACGCTGCGT CGCAGTCAGA CCCACTACCT
TGTGCCGCTC TGGCTGAAAA TGTACTTGAC CTGCGACGCA GCGTCAGTCT GGGTGATGGA 11290      11300      11310      11320      11330      11340
GGAGGAGATG GCCTTACAGG TGGAGATTCT AAAACCCCGC GGCGTACGTC ACCGCGCTAT
CCTCCTCTAC CGGAATGTCC ACCTCTAAGA TTTTGGGGCG CCGCATGCAG TGGCGCGATA
```

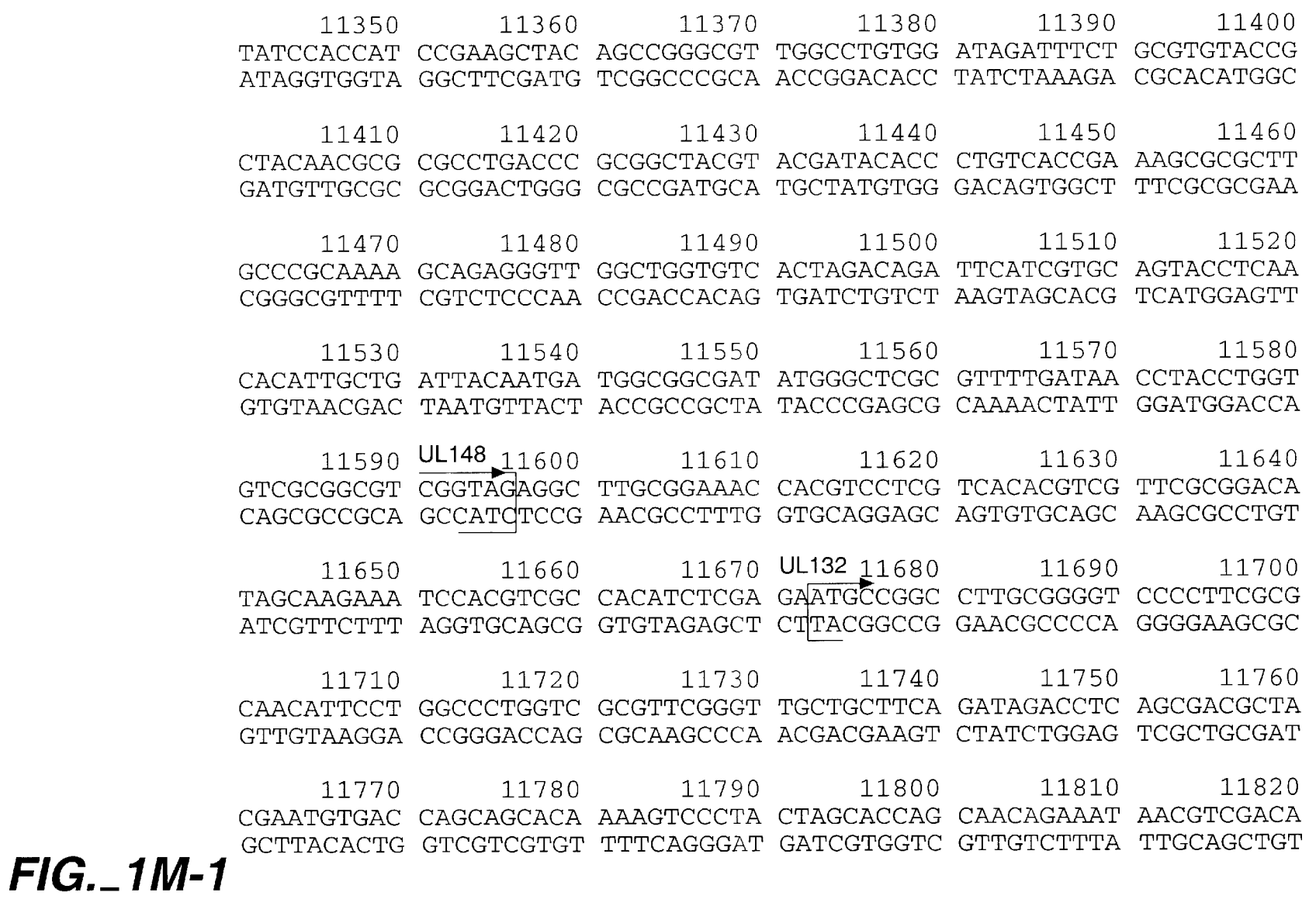

```
         11830             11840             11850             11860             11870             11880
ACGCCACGAG        TAGCGGACCC        ACAACCGGGA        TCAACATGAC        CACCACCCAC        GAGTCTTCCG
TGCCGGTCTC        ATCGCCTGGG        TGTTGGCCCT        AGTTGTACTG        GTGGTGGGTG        CTCAGAAGGC 11890             11900             11910             11920             11930             11940
TTCACAACGT        GCGCAATAAC        GAGATCATGA        AAGTGCTGGC        TATCCTCTTC        TACATCGTGA
AAGTGTTGCA        CGCGTTATTG        CTCTAGTACT        TTCACGACCG        ATAGGAGAAG        ATGTAGCACT 11950             11960             11970             11980             11990             12000
CAGGCACCTC        CATTTTCAGC        TTCATAGCGG        TACTGATCGC        GGTAGTTTAC        TCCTCGTGTT
GTCCGTGGAG        GTAAAAGTCG        AAGTATCGCC        ATGACTAGCG        CCATCAAATG        AGGAGCACAA 12010             12020             12030             12040             12050             12060
GCAAGCACCC        GGGCCCGCTTT        CGTTTCGCCG        ACGAAGAGGC        CGTCAACCTG        TTGGACGACA
CGTTCGTGGG        CCCGGCGAAA        GCAAAGCGGC        TGCTTCTCCG        GCAGTTGGAC        AACCTGCTGT 12070             12080             12090             12100             12110             12120
CGGACGACAG        TGGCGGCAGC        AGCCCGTTTG        GCAGCGGTTC        CCGACGAGGT        TCTCAGATCC
GCCTGCTGTC        ACCGCCGTCG        TCGGGCAAAC        CGTCGCCAAG        GGCTGCTCCA        AGAGTCTAGG 12130             12140             12150             12160             12170             12180
CCGCCGGATT        TTGTTCCTCG        AGCCCTTATC        AGCGGTTGGA        AACTCGGGAC        TGGGACGAGG
GGCGGCCTAA        AACAAGGAGC        TCGGGAATAG        TCGCCAACCT        TTGAGCCCTG        ACCCTGCTCC 12190             12200             12210             12220             12230             12240
CCGCCGCGGC        GTCCGCGGCC        CGCGAGCGCA        TGAAACATGA        TCCTGAGAAC        GTCATCTATT
GGCGGCGCCG        CAGGCGCCGG        GCGCTCGCGT        ACTTTGTACT        AGGACTCTTG        CAGTAGATAA 12250             12260             12270             12280             12290             12300
AGGAGGAGGA        TGGCAACTTG        GACACGTCGT        TCGTGAATCC        CAATTATGGG        AGAGGCTCGC
TCCTCCTCCG        ACCGTTGAAC        CTGTGCAGCA        AGCACTTAGG        GTTAATACCC        TCTCCGAGCG
```

FIG._1M-2

```
12310            12320            12330            12340            12350            12360
CTTTGACCAT       CGAATCTCAC       CTCTCGGACA       ATGAGGAGGA       CCCCATCAGG       TACTACGTTT
GAAACTGGTA       GCTTAGAGTG       GAGAGCCTGT       TACTCCTCCT       GGGGTAGTCC       ATGATGCAAA 12370            12380            12390            12400            12410            12420
CGGTGTACGA       TGAACTGACC       GCCTCGGAAA       TGGAAGAACC       TTCGAACAGC       ACCAGCTGGC
GCCACATGCT       ACTTGACTGG       CGGAGCCTTT       ACCTTCTTGG       AAGCTTGTCG       TGGTCGACCG 12430            12440            12450            12460            12470            12480
AGATTCCCAA       ACTAATGAAA       GTTGCCATGC       AACCCGTCTC       GCTCAGAGAT       CCCGAGTACG
TCTAAGGGTT       TGATTACTTT       CAACGGTACG       TTGGGCAGAG       CGAGTCTCTA       GGGCTCATGC

UL132  12490     12500            12510            12520            12530            12540
ACTAGGCTTT       TTTTTTTGTC       TTTCGGTTCC       AACTCTTTCC       CCGCCCCATC       ACCTCGCCTG
TGATCCGAAA       AAAAAAACAG       AAAGCCAAGG       TTGAGAAAGG       GGCGGGGTAG       TGGAGCGGAC 12550            12560            12570            12580            12590            12600
TACTATGTGT       ATGATGTCTC       ATAATAAAGC       TTTCTTTCTC       AGTCTGCAAC       ATGCAGCTGT
ATGATACACA       TACTACAGAG       TATTATTTCG       AAAGAAAGAG       TCAGACGTTG       TACGTCGACA 12610            12620            12630            12640            12650            12660
GTCGGGTGTG       GCTGTCTGTT       TGTCTGTGCG       CCGTGGTGCT       GGGTCAGTGC       CAGCGGGAAA
CAGCCCACAC       CGACAGACAA       ACAGACACGC       GGCACCACGA       CCCAGTCACG       GTCGCCCTTT 12670            12680            12690            12700            12710            12720
CCGCGGAAAA       AAACGATTAT       TACCGAGTAC       CGCATTACTG       GGACGCGTGC       TCTCGCGCGC
GGCGCCTTTT       TTTGCTAATA       ATGGCTCATG       GCGTAATGAC       CCTGCGCACG       AGAGCGCGCG 12730            12740            12750            12760            12770            12780
TGCCCGGACCA      AACCCGTTAC       AAGTATGTGG       AACAGCTCGT       GGACCTCACG       TTGAACTACC
ACGGGCTGGT       TTGGGCAATG       TTCATACACC       TTGTCGAGCA       CCTGGAGTGC       AACTTGATGG
```

FIG._1N-1

```
       12790             12800             12810             12820             12830             12840
ACTACGATGC GAGCCACGGC TTGGACAACT TTGACGTGCT CAAGAGGTGA GGGTACGCGC
TGATGCTACG CTCGGTGCCG AACCTGTTGA AACTGCACGA GTTCTCCACT CCCATGCGCG 12850             12860             12870             12880             12890             12900
TAAAGGTGCA TGACAACGGG AAGGTAAGGG CGAACGGGTA ACGGCTAAGT AACCGCATGG
ATTTCCACGT ACTGTTGCCC TTCCATTCCC GCTTGCCCAT TGCCGATTCA TTGGCGTACC 12910             12920             12930             12940             12950             12960
GGTATGAAAT GACGTTTGGA ACCTGTGCTT GCAGAATCAA CGTGACCGAG GTGTCGTTGC
CCATACTTTA CTGCAAACCT TGGACACGAA CGTCTTAGTT GCACTGGCTC CACAGCAACG 12970             12980             12990             13000             13010             13020
TCATCAGCGA CTTTAGACGT CAGAACCGTC GCGGCGGCAC CAACAAAAGG ACCACGTTCA
AGTAGTCGCT GAAATCTGCA GTCTTGGCAG CGCCGCCGTG GTTGTTTTCC TGGTGCAAGT 13030             13040             13050             13060             13070             13080
ACGCCGCCGG TTCGCTGGCG CCACACGCCC GGAGCCTCGA GTTCAGCGTG CGGCTCTTTG
TGCGGCGGCC AAGCGACCGC GGTGTGCGGG CCTCGGAGCT CAAGTCGCAC GCCGAGAAAC 13090             13100    UL130  13110             13120             13130             13140
CCAACTAGCC TGCGTCACGG GAAATAATAT GCTGCGGCTT CTGCTTCGTC ACCACTTTCA
GGTTGATCGG ACGCAGTGCC CTTTATTATA CGACGCCGAA GACGAAGCAG TGGTGAAAGT 13150             13160             13170             13180             13190             13200
CTGCCTGCTT CTGTGCGCGG TTTGGGCAAC GCCCTGTCTG GCGTCTCCGT GGTCGACGCT
GACGGACGAA GACACGCGCC AAACCCGTTG CGGGACAGAC CGCAGAGGCA CCAGCTGCGA
```

FIG._1N-2

```
         13210      13220      13230      13240      13250      13260
    AACGGCAAAC CAGAATCCGT CCCCGCCATG GTCTAAACTG ACGTATTCCA AACCGCATGA
    TTGCCGTTTG GTCTTAGGCA GGGGCGGTAC CAGATTTGAC TGCATAAGGT TTGGCGTACT 13270      13280      13290      13300      13310      13320
    CGCGGCGACG TTTTACTGTC CTTTTCTCTA TCCCTCGCCC CCACGGTCCC CCTTGCAATT
    GCGCCGCTGC AAAATGACAG GAAAAGAGAT AGGGAGCGGG GGTGCCAGGG GGAACGTTAA 13330      13340      13350      13360      13370      13380
    CTCGGGGTTC CAGCAGGTAT CAACGGGTCC CGAGTGTCGC AACGAGACCC TGTATCTGCT
    GAGCCCCAAG GTCGTCCATA GTTGCCCAGG GCTCACAGCG TTGCTCTGGG ACATAGACGA 13390      13400      13410      13420      13430      13440
    GTACAAACCGG GAAGGCCAGA CCTTGGTGGA GAGAAGCTCC ACCTGGGTGA AAAAGGTGAT
    CATGTTTGGCC CTTCCGGTCT GGAACCACCT CTCTTCGAGG TGGACCCACT TTTTCCACTA 13450      13460      13470      13480      13490      13500
    CTGGTATCTG AGCGGGTCGCA ACCAGACCAT CCTCCAACGG ATGCCCCAAA CGGCTTCGAA
    GACCATAGAC TCGCCAGCGT TGGTCTGGTA GGAGGTTGCC TACGGGGTTT GCCGAAGCTT 13510      13520      13530      13540      13550      13560
    ACCGAGCGAC GGAAACGTGC AGATCAGCGT GGAAGACGCC AAGATTTTTG GAGCGCACAT
    TGGCTCGCTG CCTTTGCACG TCTAGTCGCA CCTTCTGCGG TTCTAAAAAC CTCGCGTGTA 13570      13580      13590      13600      13610      13620
    GGTGCCCAAG CAGACCAAGC TGCTACGCTT CGTCGTCAAC GATGGCACGC GTTATCAGAT
    CCACGGGTTC GTCTGGTTCG ACGATGCGAA GCAGCAGTTG CTACCGTGCG CAATAGTCTA 13630      13640      13650      13660      13670      13680
    GTGTGTGATG AAGCTGGAGA GCTGGGCCCA CGTCTTCCGG GACTACAGCG TGTCTTTTCA
    CACACACTAC TTCGACCTCT CGACCCGGGT GCAGAAGGCC CTGATGTCGC ACAGAAAAGT
```

FIG._10-1

```
13690                 13700                 13710                 13720                 13730                 13740
GGTGCGATTG ACGTTCACCG AGGCCAATAA CCAGACTTAC ACCTTCTGTA CCCATCCCAA
CCACGCTAAC TGCAAGTGGC TCCGGTTATT GGTCTGAATG TGGAAGACAT GGGTAGGGTT

13750 UL130    13760                 13770                 13780                 13790                 13800
TCTCATCATT TGAGCCCGTC GCGGCGCAG GGAATTTTGA AAACCGCGCG TCATGAGTCC
AGAGTAGTAA ACTCGGGCAG CGCGCGCGTC CCTTAAAACT TTTGGGCGCG AGTACTCAGG 13810                 13820                 13830                 13840                 13850                 13860
CAAAGACCTG ACGCCGTTCT TGACGACGTT GTGGCTGCTA TTGGGTCACA GCCGCGTGCC
GTTTCTGGAC TGCGGCAAGA ACTGCTGCAA CACCGACGAT AACCCAGTGT CGGCGCACGG 13870                 13880                 13890                 13900                 13910                 13920
GCGGGTGCGC GCAGAAGAAT GTTGCGAATT CATAAACGTC AACCACCCGC CGGAACGCTG
CGCCCACGCG CGTCTTCTTA CAACGCTTAA GTATTTGCAG TTGGTGGGCG GCCTTGCGAC 13930                 13940                 13950                 13960                 13970                 13980
TTACGATTTC AAAATGTGCA ATCGCTTCAC CGTCGCGTAC GTATTTTCAT GATTGTCTGC
AATGCTAAAG TTTTACACGT TAGCGAAGTG GCAGCGCATG CATAAAAGTA CTAACAGACG 13990                 14000                 14010                 14020                 14030                 14040
GTTCTGTGGT GCGTCTGGAT TTGTCTCTCG ACGTTTCTGA TAGCCATGTT CCATCGACGA
CAAGACACCA CGCAGACCTA AACAGAGAGC TGCAAAGACT ATCGGTACAA GGTAGCTGCT 14050                 14060                 14070                 14080                 14090                 14100
TCCTCGGGAA TGCCAGAGTA GATTTTCATG AATCCACAGG CTGCCGTGTC CGGACGGCGA
AGGAGCCCTT ACGGTCTCAT CTAAAAGTAC TTAGGTGTCC GACGGCACAG GCCTGCCGCT 14110                 14120                 14130                 14140                 14150                 14160
AGTCTGCTAC AGTCCCGAGA AAACGGCTGA GATTCGCGGG ATCGTCACCA CCATGACCCA
TCAGACGATG TCAGGGCTCT TTTGCCGACT CTAAGCGCCC TAGCAGTGGT GGTACTGGGT
```

*FIG._10-2*

```
        14170      14180      14190      14200      14210      14220
   TTCATTGACA CGCCAGGTCG TACACAACAA ACTGACGAGC TGCAACTACA ATCCGTAAGT
   AAGTAACTGT GCGGTCCAGC ATGTGTTGTT TGACTGCTCG ACGTTGATGT TAGGCATTCA 14230      14240      14250      14260      14270      14280
   CTCTTCCTCG AGGGCCTTAC AGCCTATGGG AGAGTAAGAC AGAGAGGGAC AAAACATCAT
   GAGAAGGAGC TCCCGGAATG TCGGATACCC TCTCATTCTG TCTCTCCCTG TTTTGTAGTA 14290      14300      14310      14320      14330      14340
   TAAAAAAAAA AGTCTAATTT CACGTTTTGT ACCCCCCTTC CCCTCCGTGT TGTAGCCCAT
   ATTTTTTTTT TCAGATTAAA GTGCAAAACA TGGGGGGAAG GGGAGGCACA ACATCGGGTA 14350      14360      14370      14380      14390      14400
   CGGCCGCGGC GATCTCCTAG TAACACTCGT CCGACACTTC CACCATCTCC AGCTCGGCCG
   GCCGGCGCCG CTAGAGGATC ATTGTGAGCA GGCTGTGAAG GTGGTAGAGG TCGAGCCGGC 14410      14420      14430      14440      14450      14460
   GCGGTTCGGC ATCCTCTACC AGCGGGCGTCG TCTCATCTTT GCCGCAGCAG CGGACGCACA
   CGCCAAGCCG TAGGAGATGG TCGCGCAGC  AGAGTAGAAA CGGCGTCGTC GCCTGCGTGT 14470      14480      14490      14500      14510      14520
   CCTTCTCCAG GCAGAACGCC ACCAGCTGCC GCCGAACGTA CCACAGGTAC ACGTGCAGAC
   GGAAGAGGTC CGTCTTGCGG TGGTCGACGG CGGCTTGCAT GGTGTCCATG TGCACGTCTG 14530      14540      14550      14560      14570      14580
   CTGCGAACAG GACTACGGAG GTCATGACCA CCACGACGCA CACGGGAATC CAGGGATCGA
   GACGCTTGTC CTGATGCCTC CAGTACTGGT GGTGCTGCGT GTGCCCTTAG GTCCCTAGCT 14590      14600      14610      14620      14630      14640
   GATTGTTGCT GGAACTCATG GCTATCGCCA CCGACGTGCC CGCGTCTGTC TCACCGCCGC
   CTAACAACGA CCTTGAGTAC CGATAGCGGT GGCTGCACGG GCGCAGACAG AGTGGCGGCG
```

*FIG._1P-1*

```
        14650      14660      14670      14680      14690      14700
   TCGCCCGATG TCGCGCGGCT TGTTATACGC TAGCCCGTCG CCGCCTCGGG GCACGGTGCC
   AGCGGGCTAC AGCGCGCCGA ACAATATGCG ATCGGGCAGC GGCGGAGCCC CGTGCCACGG 14710      14720      14730      14740      14750      14760
   CTCCTACCCA CGTAACTTCC TCCGTGACTT AAAGTCGCGT GTGGTAGATC TCCTGCTCCG
   GAGGATGGGT GCATTGAAGG AGGCACTGAA TTTCAGCGCA CACCATCTAG AGGACGAGGC 14770      14780      14790      14800      14810      14820
   TGGACGAACC GTCCGGCAGG ATAGCGGTTA AGGATTCGGT GCTAAGGCCG TGTCGCCAAC
   ACCTGCTTGG CAGGCCGTCC TATCGCCAAT TCCTAAGCCA CGATTCCGGC ACAGCGGTTG 14830      14840      14850      14860      14870      14880
   GTCGAATGCT ACGTTGCAAC AGCTTCGACG GACGGCCATC CCCTCTCTCA TCGCAATAAT
   CAGCTTACGA TGCAACGTTG TCGAAGCTTG CTGCCGGTAG GGGAGAGAGT AGCGTTATTA 14890      14900      14910      14920      14930      14940
   AAAACACCAG CAGCGCGCAC GACGCGATCA CGGTGACACC CATGATTAGA CCCACGCAGA
   TTTTGTGGTC GTCGCGCGTG CTGCGCTAGT GCCACTGTGG GTACTAATCT GGGTGCGTCT 14950      14960      14970      14980      14990      15000
   TAGCCAGCCC CGCTAGCGTA TCTAGCGCCA TCCCGTTCGC TCCCGTTGTC TCCTGAGCGA
   ATCGGTCGGG GCGATCGCAT AGATCGCGGT AGGGCAAGCG AGGGCAACAG AGGACTCGCT 15010      15020      15030      15040      15050      15060
   AGCAACTTCT CGGTCCCCGT TTTCAACAGT TTTTGTTTCC TTCTCCGCGA CTAGATGTTA
   TCGTTGAAGA GCCAGGGGCA AAAGTTGTCA AAAACAAAGG AAGAGGCGCT GATCTACAAT 15070      15080      15090      15100      15110      15120
   ACGCCCGCGG TCTTTCCGGC CGTGCTCTAC CTCCTGGCGC TTGTCGTCTG GGTTGAGATG
   TGCGGGCGCC AGAAAGGCCG GCACGAGATG GAGGACCGCG AACAGCAGAC CCAACTCTAC
```

*FIG._1P-2*

```
           15130                15140                15150                15160                15170                15180
      TTCTGCCTCG           TCGCCGTAGC           CGTCGTCGAG           CGCGAGATCG           CCTGGGCGCT           GCTGCTGCGG
      AAGACGGAGC           AGCGGCATCG           GCAGCAGCTC           GCGCTCTAGC           GGACCCGCGA           CGACGACGCC 15190                15200                15210                15220                15230                15240
      ATGCTGGTCG           TTGGCCTGAT           GGTGGAAGTC           GGCGCCGCCG           CCGCTTGGAC           CTTCGTGCGT
      TACGACCAGC           AACCGGACTA           CCACCTTCAG           CCGCGGCGGC           GGCGAACCTG           GAAGCACGCA 15250                15260                15270                15280                15290                15300
      TGTCTTGCCT           ATCAGCGCTC           CTTCCCCGTG           CTTACGGCCT           TCCCCTGAAA           CCCACGTTAA
      ACAGAACGGA           TAGTCGCGAG           GAAGGGGCAC           GAATGCCGGA           AGGGGACTTT           GGGTGCAATT 15310                15320                15330                15340                15350                15360
      CCGACCGTCC           CAAAAACGCC           GGTGTTAACA           CAGGAAAAAA           AGAAACCACG           CAGGAACCGC
      GGCTGGCAGG           GTTTTTGCGG           CCACAATTGT           GTCCTTTTTT           TCTTTGGTGC           GTCCTTGGCG 15370                15380                15390                15400                15410                15420
      GCAGGAACCA           CGCGGAACAT           GGGACACTAT           CTGGAAATCC           TGTTCAACGT           CATCGTCTTC
      CGTCCTTGGT           GCGCCTTGTA           CCCTGTGATA           GACCTTTAGG           ACAAGTTGCA           GTAGCAGAAG 15430                15440                15450                15460                15470                15480
      ACTCTGCTGC           TCGGCGTCAT           GGTCAGTATC           GTCGCTTGGT           ACTTCACGTG           AACCACCGTC
      TGAGACGACG           AGCCGCAGTA           CCAGTCATAG           CAGCGAACCA           TGAAGTGCAC           TTGGTGGCAG 15490                15500                15510                15520                15530                15540
      GTCCCGGTTT           AAAAACCATC           ATCGACGGCC           GTTATAAAGC           CACCCGGACA           CGCGCCGCGG
      CAGGGCCAAA           TTTTTGGTAG           TAGCTGCCGG           CAATATTTCG           GTGGGCCTGT           GCGCGGCGCC 15550                15560                15570                15580                15590                15600
      CACTTGCCTA           CGGCGCTGCT           TCAGGGAAAC           TCCTCTTCCT           TCTGCTCTTC           CTCCTTCACC
      GTGAACGGAT           GCCGCGACGA           AGTCCCTTTG           AGGAGAAGGA           AGACGAGAAG           GAGGAAGTGG
```

*FIG._1Q-1*

```
15610      15620      15630      15640      15650      15660
GCAGGGATCG TTTCCCTCGA CCAGGGACTC GCCGAAGCAA CCGCCGGAGC AACCTGGAGG
CGTCCCTAGC AAAGGGAGCT GGTCCCTGAG CGGCTTCGTT GGCGGCCTCG TTGGACCTCC 15670      15680      15690      15700      15710      15720
AGTCGCGGCA TGACGGCGCC CAAGTGTGTC ACCACCAGTA CTTATCTGGT CAAGACCAAG
TCAGCGCCGT ACTGCCGCGG GTTCACACAG TGGTGGTCAT GAATAGACCA GTTCTGGTTC 15730      15740      15750    15760 UL149 15770      15780
GAACAGCCCT GGTGGCCCGA CAACGCCATC AGGAGATGGT GGATCAGTGT TGCTATCGTC
CTTGTCGGGA CCACCGGGCT GTTGCGGTAG TCCTCTACCA CCTAGTCACA ACGATAGCAG 15790      15800      15810      15820      15830      15840
ATCTTCATCG GAGTCTGTCT GGTGGCCCTG ATGTACTTTA CGCAGCAGCA GGCACGCAGC
TAGAAGTAGC CTCAGACAGA CCACCGGGAC TACATGAAAT GCGTCGTCGT CCGTGCGTCG 15850      15860      15870 UL150 15880      15890      15900
GGGAGCAGCA GCGGGCTAGC CGGCTACAGC CGGAAGCGCC TCCAAGCGCC GTAGCCGGGC
CCCTCGTCGT CGCCCGATCTG GCCGATGTCG AGGTTCGCGG CATCGGCCCG 15910      15920      15930      15940      15950      15960
CGCCTGCCGA TCGCGACGTC GTGGACCATC GAACAGAGAC TCACGCGGTAC GAGACCCCGA
GCGGACGGCT AGCGCTGCAG CACCTGGTAG CTTGTCTCTG AGTGCGCATG CTCTGGGGCT 15970      15980      15990      16000      16010      16020
GGTACGCCAC GCGGTGCCTA ACGGGTATA CCACACCCGT ACGGTCTGCA GTGCGGCGTA
CCATGCGGTG CGCCACGGAT TGCGCCATAT GGTGTGGGCA TGCCAGACGT CACGCCGCAT 16030      16040      16050      16060      16070      16080
CAACGTGTGG AAAACGCGTT GCGTCGCAGA GTCCGCCACG TTCCTGTCTT GTCGCTCCCC
GTTGCACACC TTTTGCGCAA CGCAGCGTCT CAGGCGGTGC AAGGACAGAA CAGCGAGGGG
```

FIG._1Q-2

```
          16090             16100             16110             16120 UL149 16130             16140
AATCGTCTCC        CGCACACCCC        CCGGCGACACC        CAGAGGGCGG        GTGAGCCAAG        TATTCTTAAG
TTAGCAGAGG        GCGTGTGGGG        GGCGCTGTGG        GTCTCCCGCC        CACTCGGTTC        ATAAGAATTC 16150             16160             16170             16180             16190             16200
GCCGTTCTTT        GTTCCATAGC        CCATAAATTG        TTGATTCCGG        AGCTCGTTGG        CGCGGAAATA
CGGCAAGAAA        CAAGGTATCG        GGTATTTAAC        AACTAAGGCC        TCGAGCAACC        GCGCCTTTAT 16210             16220             16230             16240             16250             16260
GCCGGATAAG        GGGAGCAACA        ACCGTTGGCG        AAAGCCGTCC        CGCTCATTCA        GTCCGGGTTT
CGGCCTATTC        CCCTCGTTGT        TGGCAACCGC        TTTCGGCAGG        GCGAGTAAGT        CAGGCCCAAA 16270             16280             16290             16300             16310             16320
CGCGTCCAGT        CGGACGTGTG        ACCGTTGGGC        AACGGAACGG        CGTTTCACTG        CCAAAATCGT
GCGCAGGTCA        GCCTGCACAC        TGGCAACCCG        TTGCCTTGCC        GCAAAGTGAC        GGTTTTAGCA 16330             16340             16350             16360             16370             16380
ATCGGGTAGT        GTACGAGACG        TCGGGCGGTGC        AGAATGCGAC        TCGCGGCGTA        GCTCGCCGTC
TAGCCCATCA        CATGCTCTGC        AGCCCGCCACG        TCTTACGCTG        AGCGCCGCAT        CGAGCGGCAG 16390             16400             16410             16420             16430             16440
GCTATGCGGC        TCGTCGCCGT        GTGGCCGGGC        CTGGCCGGCT        GTCTGCGTCC        AGATCTGTTG
CGATACGCCG        AGCAGCGGCA        CACCGGCCCG        GACCGGCCGA        CAGACGCAGG        TCTAGACAAC 16450             16460             16470             16480             16490             16500
GCCTTTTGGT        TCCTCTGGCT        GCTGCTGCGT        GTGTGCTTTG        GTAGACGCGG        TGGCAGTTTG
CGGAAAACCA        AGGAGACCGA        CGACGACGCA        CACACGAAAC        CATCTGCGCC        ACCGTCAAAC 16510             16520             16530             16540             16550             16560
CGGTCTGCGG        TAAGTGAGGA        TGTCGCCCGAG        CAAACGCACT        TGCGGCGCGT        GGGCGGCACG
GCCAGACGCC        ATTCACTCCT        ACAGCGGGCTC       GTTTGCGTGA        ACGCCGCGCA        CCCGCCGTGC
```

FIG._1R-1

```
16570      16580      16590      16600      16610      16620
CGTGTCATTG TAGGTTCGTT GCCAGATGGC AAGTGCTGTC AACAGCAGGC GTTGTGGGCG
GCACAGTAAC ATCCAAGCAA CGGTCTACCG TTCACGACAG TTGTCGTCCG CAACACCCGC 16630      16640      16650      16660      16670      16680
GTCGGTGTAT TTTTGTGGGT TGCGGTGAGA GTCGGCACTC GGTGTTTTGT GAGTCATCTC
CAGCCACATA AAAACACCCA ACGCCACTCT CAGCCGTGAG CCACAAAACA CTCAGTAGAG 16690      16700      16710      16720      16730      16740
AACTATCTGT GTTGCTTTGA GCAGGCGTCC AGAACAGCGAC GCGACTTTGG GGATGGCCTC
TTGATAGACA CAACGAAACT CGTCCGCAGGT CTTGTCGCTG CGCTGAAACC CCTACCGGAG 16750      16760      16770      16780      16790      16800
GTGCTCACCT CCGCGGAGAG CGCCGCCGGA CCTGCTCGTC AGCAGCGAGC TACGCAGACG
CACGAGTGGA GGCGCCTCTC GCGGGGGCCT GGACGAGACG TCGTCGCTCG ATGCGTCTGC 16810      16820      16830      16840      16850      16860
GAATATCTGG AGGAGAGTTA CGTGTGTCAC AGGAGAGCGC GGGTCTCCGG CGGTAACGAC
CTTATAGACC TCCTCTCAAT GCACACAGTG TCCTCTCGCG CCCAGAGCCG GCCATTGCTG 16870      16880      16890      16900      16910      16920
GGCGGTGTCG TCGACACGTG TGCGGCCTGT TGTGCTCTGC GGAAAAGTGC CGGTCTCGGA
CCGCCACAGC AGCTGTGCAC ACGCCGGACA ACACGAGACG CCTTTTCACG GCCAGAGCCT 16930      16940      16950      16960      16970      16980
GACCGTGGAC GAAAAAGAGA ACGCAGCAGC TACCGCTGGC GGCGGCGGCG TTAATGCAGC
CTGGCACCTG CTTTTTCTCT TGCGTCGTCG ATGGCGACCG CCGCCGCCGC AATTACGTCG
```

*FIG. _1R-2*

```
                16990                 17000                 17010                 17020                 17030                 17040
           CGTTGATGTT            CGACGTTGTG            AGCACTCGGA            AACAGCGGTG            AGGCAGAAGG            TCGATTCTCC
           GCAACTACAA            GCTGCAACAC            TCGTGAGCCT            TTGTCGCCAC            TCCGTCTTCC            AGCTAAGAGG 17050                 17060                 17070                 17080                 17090                 17100
           AGGGAACGAC            AGTCGATGCG            TGGTAGCCGC            AGCAGGTGAG            GTTGGGGCGG            ACAACGTGTT
           TCCCTTGCTG            TCAGCTACGC            ACCATCGGCG            TCGTCCACTC            CAACCCCGCC            TGTTGCACAA 17110                 17120                 17130                 17140                 17150                 17160
           GCGGATTGTG            GCGAGAACGT            CGTCCCTCCCC           TTCTTCACCG            CCCCACCCAC            CCTCGGTTGG
           CGCCTAACAC            CGCTCTTGCA            GCAGGAGGGG            AAGAAGTGGC            GGGGTGGGTG            GGAGCCAACC 17170                 17180                 17190                 17200                 17210                 17220
           TGTTTCTTTT            TTCTTGTGTC            CTGCAGATAG            TTCCACGGAC            AGCGACGGCA            AGTCCATAAT
           ACAAAGAAAA            AAGAACACAG            GACGTCTATC            AAGGTGCCTG            TCGCTGCCGT            TCAGGTATTA 17230                 17240                 17250                 17260                 17270                 17280
           CAGCGGTGTG            CAAGTGGTGG            AACACGACGA            AGATATCATC            GCGCCGCAGA            GTTGTGTGTG
           GTCGCCACAC            GTTCACCACC            TTGTGCTGCT            TCTATAGTAG            CGCGGCGTCT            CAAACACCAC

17290 UL151         17300                 17310                 17320                 17330                 17340
           CACGGGCGTTC           TCTGGGATGT            GGCTCTGTTG            GAAGTGCCGC            GTTGGGCGTG
           GTGCCGCAAG            AGACCCTACA            CCGAGACAAC            CTTCACGGCG            CAACCCGCAC
                     ─────────▶

17350                 17360                 17370                 17380                 17390                 17400
           GCAGGGCTGG            AAGAGGTGGC            GCAACAGCGA            GGCCGGGCGT            CGATGGAGTG            CTGGGTCTGC
           CGTCCCGACC            TTCTCCACCG            CGTTGTCGCT            CCGGCCCGCA            GCTACCTCAC            GACCCAGACG 17410                 17420                 17430                 17440                 17450                 17460
           GTCGGCTTCC            AGCTTGTCTG            ACTTGGCGGG            CGAGGCCGTT            GGAGAATTGG            TGGGATCGGT
           CAGCCGAAGG            TCGAACCGCC            TGAACCGCCC            GCTCCGACAA            CCTCTTAACC            ACCCTAGCCA
```

```
17470        17480        17490        17500        17510        17520
CGTCGCGTAC   GTGATCCTTG   AACGTCTGTG   GTTGGCAGCC   AGAGGTTGGG   TGTGCGAAAC
GCAGCGCATG   CACTAGGAAC   TTGCAGACAC   CAACCGTCGG   TCTCCAACCC   ACACGCTTTG 17530        17540        17550        17560        17570        17580
AGGTGTGGAA   GCCGAGGAGG   CCATGTCGCG   GCGGCGACAG   CGCATGCTGT   GGCGTATTGT
TCCACACCTT   CGGCTCCTCC   GGTACAGCGC   CGCCGCTGTC   GCGTACGACA   CCGCATAACA 17590        17600        17610        17620        17630        17640
TCTCTCGTGG   AGGCGACGGC   GAATGCAGCA   GACGGTGTTC   GATGGAGATG   GCGTGCGGGG
AGAGAGCACC   TCCGCTGCCG   CTTACGTCGT   CTGCCACAAG   CTACCTCTAC   CGCACGCCCC 17650        17660        17670        17680        17690        17700
AAGAAAGCGC   CGTGTTGTGA   GCAGACGACG   TAGGATGCGG   GACGTCGGAG   CACATGGGCC
TTCTTTCGCG   GCACAACACT   CGTCTGCTGC   ATCCTACGCC   CTGCAGCCTC   GTGTACCCGG 17710        17720        17730        17740        17750        17760
ATGTGTGGTG   GCAGATGGCG   GTGTCCGCTG   CGGCAGTGCA   TAGACGAAGC
TACACACCAC   CGTCTACCGC   CACAGGCGAC   GCCGTCACGT   ATCTGCTTCG

UL150
17770        17780        17790        17800        17810        17820
AACATGTCGC   TGTGAAGAGA   TAGAGTGTGA   GCATAGCTGC   ATGCAGCGTT   GCGTGTATAA
TTGTACAGCG   ACACTTCTCT   ATCTCACACT   CGTATCGACG   TACGTCGCAA   CGCACATATT 17830        17840        17850        17860        17870        17880
GCGGSGGGGA   TTAAGACGTT   AATAAAGAAT   AGCGGCGGTT   CTGATAGGGC   GACCGCTGAA
CGCCCCCCCT   AATTCTGCAA   TTATTTCTTA   TCGCCGCCAA   GACTATCCCG   CTGGCGACTT 17890        17900        17910        17920        17930        17940
GTGAGCTGCG   GTTTGTGGTG   GTTTGTGGAG   TCCCCGCCCC   CCCCGGTCCC   GTGTCCGCCG
CACTCGACGC   ACACGCACAC   CAAACACCTC   AGGGGCGGGG   GGGGCCAGGG   CACAGGCGGC
```

```
        17950           17960           17970           17980           17990           18000
GCAAAGCCCC  CCGGNTCCGC  ACACTCCTGG  CCGGCGCAACC  CTCGTCGCTG  CAAAAGCCCC
CGTTTCGGGG  GGCCNAGGCG  TGTGAGGACC  GGCGCGTTGG  GAGCAGCGAC  GTTTTCGGGG 18010           18020           18030           18040           18050           18060
CCGTCCCCGC  ACACCCCCGC  GACCGCCGGT  CCCGCGAGTC  CCCGTCCCCG  CCGCAAAAGG
GGCAGGGGCG  TGTGGGGGCG  CTGGCGGCCA  GGGCGCTCAG  GGGCAGGGGC  GGCGTTTTCC 18070           18080           18090           18100           18110           18120
CCCCGTCCT   CGCCGCAAAC  ACCCCCGTCA  CCCCCGTCCC  TCAGNCCGGG  TCCGCGAGTC
GGGGCAGGA   GCGGCGTTTG  TGGGGGCAGT  GGGGGCAGGG  AGTCNGGCCC  AGGCGCTCAG 18130           18140           18150           18160           18170           18180
CCCGTTCCCA  GCGTAATCCC  CGTACCCGCA  CCGNCCCGGN  CCCACCGTCG  TCCCGCACAC
GGGCAAGGGT  CGCATTAGGG  GCATGGGCGT  TGCNGGGCCN  GGGTGGCAGC  AGGGCGTGTG 18190           18200           18210           18220           18230           18240
CCCCGTCCC   CCAGCCCGGT  GCCCAGCGTG  CGAAAAAAGC  TCCGTCCCTC  ACACCCGCAG
GGGGCAGGG   GGTCGGGCCA  CGGGTCGCAC  GCTTTTTTCG  AGGCAGGGAG  TGTGGGCGTC 18250           18260           18270           18280           18290           18300
AAAGATCCCT  CAGCGCGGTG  AAACCCCCGTC  CCCAGCGCCG  TGCCGCTGAC  AAAGACCATG
TTTCTAGGGA  GTCGCGCCAC  TTTGGGGCAG  GGGTCGCGGC  ACGGCGACTG  TTTCTGGTAC
                                                                       ▼
                                                                       UL151
        18310           18320           18330           18340           18350           18360
GGACGACACG  CACAGGCA..  ..........  ..........  ..........  ..........
CCTGCTGTGC  GTGTCCGT..  ..........  ..........  ..........  ..........
```

*FIG._1T*

```
         10         20         30         40         50         60
ATCGGGCGCC AGAGCTAGAT CAGGCGTATC AAATTCCACT GCCAGGCGAC CTGATTCTAA
TAGCCCGCGG TCTCGATCTA GTCCGCATAG TTTAAGGTGA CGGTCCGCTG GACTAAGATT 70         80         90        100        110        120
CGGTTCCACG ATCCGGGAGA GCGTTTCTAG ATATAGAGCA AAGCGTACCA CGTCTACCTG
GCCAAGGTGC TAGGCCCTCT CGCAAAGATC TATATCTCGT TTCGCATGGT GCAGATGGAC 130        140        150        160        170        180
CGGTGTAAAA AACTGTTGTG GGCGTTCACC GTCGTTGACC ACGTAAGCCA CGTAGAGGCC
GCCACATTTT TTGACAACAC CCGCAAGTGG CAGCAACTGG TGCATTCGGT GCATCTCCGG 190        200        210        220        230        240
AACATTTCC ACCACGGGTT CTAGCTGCAG GCGGCACGTA AAGCTTAGAA ACGACGGCTG
TTGTAAAAGG TGGTGCCCAA GATCGACGTC CGCCGTGCAT TTCGAATCTT TGCTGCCGAC 250        260        270        280        290        300
TACGGTTTGG TTCCCGTGAA GCTGAAGCGT CACTTCCTTG CCGGGGCTCA CCGTGCTGTA
ATGCCAAACC AAGGGCACTT CGACTTCGCA GTGAAGGAAC GGCCCCGAGT GGCACGACAT 310        320        330        340        350        360
ACGCCGCACC GAGTCGGTCA TCTGCTCCAG ATCGGTAGAC CAGAAGGGCG TGCAATGCAT
TGCGGCGTGG CTCAGCCAGT AGACGAGGTC TAGCCATCTG GTCTTCCCGC ACGTTACGTA 370        380        390        400        410        420
ACTGTCCCAG TCGCGACACG CAGCCCAGCC TAGCTCGGTG AAGGGTCGAC GCACACCCGA
TGACAGGGTC AGCGCTGTGC GTCGGGTCGG ATCGAGCCAC TTCCCAGCTG CGTGTGGGCT 430        440        450        460        470        480
AAAAGTGTGC TTGAAGACCA GGGGGTCGCC TCGGTAGCTC AGTAGCCGAA CATGCACATA
TTTTCACACG AACTTCTGGT CCCCCAGCGG AGCCATCGAG TCATCGGCTT GTACGTGTAT
```

FIG._2A-1

```
       490        500        510        520        530        540
GTCGCGGCTA CGTTGACAGA CGGCCCGTAG ACAGGCAGGA CAAGCCGTGAA CAGCAAGCGC
CAGCGCCGAT GCAACTGTCT GCCGGGCATC TGTCCGTCCT GTTCGCACTT GTCGTTCGCG 550        560        570        580        590        600
AACATGCTGC GGGTTAGAAA ATGCGGCGTG CCGGCCACCG CCCGACTCAT AAACGCTACC
TTGTACGACG CCCAATCTTT TACGCCGCAC GGCCGGTGGC GGGCTGAGTA TTTGCGATGG 610        620        630        640        650        660
AGCATGACGT CTCAGATCAC ACAAGTGACG AGGAGCGTAC CGCAAATCAC TAGGGAAAAG
TCGTACTGCA GAGTCTAGTG TGTTCACTGC TCCTCGCATG GCGTTTAGTG ATCCCTTTTC 670        680        690        700        710        720
GCCAGCAGAG CCCGATAGTC TTGCTCTTCG CGAACGATCT CGTCCGGTTC CTCGCAGTCT
CGGTCGTCTC GGGCTATCAG AACGAGAAGC GCTTGCTAGA GCAGGCCAAG GAGCGTCAGA 730        740        750        760        770        780
TCGTGGTCCA CAGAAGATGA GGAGCAGGAT TCTTCGTTAA TTTCTGCCAG GATACTAGTG
AGCACCAGGT GTCTTCTACT CCTCGTCCTA AGAAGCAATT AAAGACGGTC CTATGATCAC 790        800        810        820        830        840
CTGTACCACA CCAGAGCGCT CAGCGTGCCC AGGGCTACCG CACGGTAAAA TAGGGACATG
GACATGGTGT GGTCTCGCGA GTCGCACGGG TCCCGATGGC GTGCCATTTT ATCCCTGTAC

UL147  850        860        870        880        890        900
ATCACCAGCG CAATCTGAAG TGGTGGTAGT TCAGTTTCTT GGCGTATTTC CAGAGAAAGG
TAGTGGTCGC GTTAGACTTC ACCACCATCA AGTCAAAGAA CCGCATAAAG GTCTCTTTCC
          ←

910        920        930        940        950        960
CTTTGTAGGC CGTAGGGACT GGCCAGGCAC CGAACTCAAT ATTGGTAGAC ACTACGTCGT
GAAACATCCG GCATCCCTGA CCGGTCCGTG GCTTGAGTTA TAACCATCTG TGATGCAGCA
```

FIG._2A-2

```
       970        980        990       1000       1010       1020
AAATGCGTTG TTCCTCGTCT AAGATTAACC GAAAAAATAG CCGGTTGATG TGACGACGCA
TTTACGCAAC AAGGAGCAGA TTCTAATTGG CTTTTTTATC GGCCAACTAC ACTGCTGCGT 1030       1040       1050       1060       1070       1080
CGGCTTGCGC GTTAGGATTG AGACACTTGG TGCCCTTGTC CTTTAAAATA GCCAGCACTT
GCCGAACGCG CAATCCTAAC TCTGTGAACC ACGGGAACAG GAAATTTTAT CGGTCGTGAA 1090       1100       1110       1120       1130       1140
CCTGACGATT GCAGCTTTCG CTCGCCGCGA TTGGCTTAAG CAATTCAGTT CCGATTGGCA
GGACTGCTAA CGTCGAAAGC GAGCGGCGCT AACCGAATTC GTTAAGTCAA GGCTAACCGT 1150       1160       1170       1180       1190       1200
GAGTATTCAA CAGAATTTGG TTGTTACAAC GACAGCGTTT GTCGTAATCT TCCAATTCTA
CTCATAAGTT GTCTTAAACC AACAATGTTG CTGTCGCAAA CAGCATTAGA AGGTTAAGAT 1210       1220       1230       1240       1250       1260
AAAGATGGAC GGCTAGGGGA CATACGACAA ATAACATGTA TGCAGTCAAT TGCATATATC
TTTCTACCTG CCGATCCCCT GTATGCTGTT TATTGTACAT ACGTCAGTTA ACGTATATAG 1270       1280       1290       1300       1310       1320
GTACCGATAA AATGTTAGTG TGCGGATTCA GAATCGGATG ATGCAACCGT CTTAGCATCA
CATGGCTATT TTACAATCAC ACGCCTAAGT CTTAGCCTAC TACGTTGGCA GAATCGTAGT 1330       1340       1350       1360       1370       1380
TATCGAAAAA GTATACATAT TACCGATTCA TTATAATTAG GGAATTATTT CCAACGCGGA
ATAGCTTTTT CATATGTATA ATGGCTAAGT AATATTAATC CCTTAATAAA GGTTGCGCCT
UL147                                                UL152

1390       1400       1410       1420       1430       1440
CGTTTGTTAG TGACAGCGTT TTCTTCTACA TGCGGTCCAT TACTATCCTT TACTTTTACC
GCAAACAATC ACTGTCGCAA AAGAAGATGT ACGCCAGGTA ATGATAGGAA ATGAAAATGG
```

FIG._2B-1

```
1450              1460              1470              1480              1490              1500
AATACTCTGT        GCCATGAGTT        GTCTTTTTTA        CCATCCAGCC        ATTTGGACAA        ATGATGATCG
TTATGAGACA        CGGTACTCAA        CAGAAAAAAT        GGTAGGTCGG        TAAACCTGTT        TACTACTAGC 1510              1520              1530              1540              1550              1560
GGAGCTAAAC        ATACAGGTTT        ACCTCGAGGA        GGCAATAGAT        AATGTTGAGG        TTTGTCACAC
CCTCGATTTG        TATGTCCAAA        TGGAGCTCCT        CCGTTATCTA        TTACAACTCC        AAACAGTGTG 1570              1580              1590              1600              1610              1620
TCAGGAGGAT        TGGGAGGGTC        ACGACCAACC        CAAAATAAGC        CACCTATAGG        ATGATGTAAA
AGTCCTCCTA        ACCCTCCCAG        TGCTGGTTGG        GTTTTATTCG        GTGGATATCC        TACTACATTT 1630              1640              1650              1660              1670              1680
GCTTTGTGGG        TACACGGACA        ACGCAATTCT        CTACTGTGAA        CCCCATGGTA        ATACATAAAT
CGAAACACCC        ATGTGCCTGT        TGCGTTAAGA        GATGACACTT        GGGGTACCAT        TATGTATTTA

UL152
1690              1700              1710              1720        1730              1740
GCCATCAAAA        GACTAATCAG        CGAACCAAAA        ATTAATCGCA        TTCTAATTTT        ATTAACTACG
CGGTAGTTTT        CTGATTAGTC        GCTTGGTTTT        TAATTAGCGT        AAGATTAAAA        TAATTGATGC 1750              1760              1770              1780              1790              1800
TCACTATCAG        TAATTCGTAA        TATCCGGTAT        TCCCGGAAAA        TCACTCAAAA        CTGCGTCCAT
AGTGATAGTC        ATTAAGCATT        ATAGGCCATA        AGGGCCTTTT        AGTGAGTTTT        GACGCAGGTA 1810              1820              1830              1840              1850              1860
GACACATCAA        TTCCCGATAA        GTACCCCCCT        TTGAAATCGG        ATCCCCCCAC        ATACCAATCA
CTGTGTAGTT        AAGGGCTATT        CATGGGGGGA        AACTTTAGCC        TAGGGGGGTG        TATGGTTAGT
```

*FIG._2B-2*

```
      1870       1880       1890       1900       1910       1920
ATCACACAAC ACACAGGTTT AAAAATCGAT CACACGTCAA TTAGGTTTCA AAATCGATAC
TAGTGTGTTG TGTGTCCAAA TTTTTAGCTA GTGTGCAGTT AATCCAAAGT TTTAGCTATG 1930       1940       1950       1960       1970       1980
TGTTTATTAT CAGGAATCTA GACTAATTCT ACAATGACAG CTCTGAATTT CTCTCTCGTC
ACAAATAATA GTCCTTAGAT CTGATTAAGA TGTTACTGTC GAGACTTAAA GAGAGAGCAG 1990       2000       2010       2020       2030       2040
TTTCTTGTCA GGTTCTCATC ATCAATCTTC ACTTCCACCC ATCGAGGAGT CATCGTCGCT
AAAGAACAGT CCAAGAGTAG TAGTTAGAAG TGAAGGTGGG TAGCTCCTCA GTAGCAGCGA 2050       2060       2070       2080       2090       2100
CCAAAACCCT TTGGGGTCGC TGGTTGGAAA AGTCTCCTGAC CACCCCGTAC
GGTTTTGGGA AACCCCAGCG ACCAACCTTT TCAGAGACTG TGCTAGGTCC GTGGGCATG 2110       2120       2130       2140       2150       2160
CCAGTCCGAC TGATCTAGCT TACGGAGCAT CTCAACAGGC ATGAGCTGCA GGGCCACGGC
GGTCAGGCTG ACTAGATCGA ATGCCTCGTA GAGTTGTCCG TACTCGACGT CCCGGTGCCG 2170       2180       2190       2200       2210       2220
TGTCACGGCA GGGATTATTA CTACCGTTCA GGTAAACTGT ATCTCCCTGA GTTACCGTGA
ACAGTGCCGT CCCTAATAAT GATGGCAAGT CCATTTGACA TAGAGGGACT CAATGGCACT 2230       2240       2250       2260       2270       2280
TGGGTCTTTC TACATGTTGA CTTTGCGTAA AAAATCGCCG GTAAAATGTT TTTTCTTGTT
ACCCAGAAAG ATGTACAACT GAAACGCATT TTTTAGCGGC CATTTTACAA AAAAGAACAA 2290       2300       2310       2320       2330       2340
CATGTAAAAG TACCGGAACT AAAATGCTAG TTAGAATGGT TGCAGTTGCT ATTAGCGCGG
GTACATTTTC ATGGCCTTGA TTTTACGATC AATCTTACCA ACGTCAACGA TAATCGCGCC
```

```
           2350       2360       2370       2380       2390       2400
     CTAGTAACAG TAGTTTAGTG TTACATTGTA TACCCATGTT TTTAATAACT ATGAATATTC
     GATCATTGTC ATCAAATCAC AATGTAACAT ATGGGTACAA AAATTATTGA TACTTATAAG 2410       2420       2430       2440       2450       2460
     TGCTTCACAC CATAAGTGCT TAACCCACAA AAACCACACG GAGACATTAT TGGCTAARAA
     ACGAAGTGTG GTATTCACGA ATTGGGTGTT TTTGGTGTGC CTCTGTAATA ACCGATTTTT 2470       2480       2490       2500       UL153 2510       2520
     TAAAAACAAA AGTTTATTGA TGTGCATGTT AGGTTTTAGT CTAAAATTCA TCTGGGTCGT
     ATTTTTGTTT TCAAATAACT ACACGTACAA TCCAAAATCA GATTTTAAGT AGACCCAGCA
                                                          ↓
           2530       2540       2550       2560       2570       2580
     ATTTGGGAAG TTTTGTATAA CGCGGTCTTC TGGGGACGCG ACGGCTACCC ATGTATAAGG
     TAAACCCTTC AAAACATATT GCGCCAGAAG ACCCCTGCGC TGCCGATGGG TACATATTCC 2590       2600       2610       2620       2630       2640
     CTATAAGTGC CACAGATACC ACTATACCCG CCCATACAGC ATGAATTCCC AGGGGAATGT
     GATATTCACG GTGTCTATGG TGATATGGGC GGGTATGTCG TACTTAAGGG TCCCCTTACA 2650       2660       2670       2680       2690       2700
     TAGTGTTTTT TACAGTTTTT ATTACATTGT CCCACGTTCT GCTATTATGC TGGTCTGATT
     ATCACAAAAA ATGTCAAAAA TAATGTAACA GGGTGCAAGA CGATAATACG ACCAGACTAA 2710       2720       2730       2740       2750       2760
     CCTCTTTTGT TTTACATTTA TCAGGTATAG GAGACGATGT TGCAGTTCCT GATAACACGG
     GGAGAAAACA AAATGTAAAT AGTCCATATC CTCTGCTACA ACGTCAAGGA CTATTGTGCC 2770       2780       2790       2800       2810       2820
     TTAAATAGTA GTTTTCCTTT TTACCGTCAC TGTAACGTTG CAAAACGTAT TTTCCAGCGT
     AATTTATCAT CAAAAGGAAA AATGGCAGTG ACATTGCAAC GTTTGCATA AAAGGTCGCA
```

FIG._2C-2

```
                2830       2840       2850       2860       2870       2880
          GTTCGGTAGT TACGTTGTAT ATAGTGAGAG AGGTCTTATT GCAGTCTAAA CACATGCCGT
          CAAGCCATCA ATGCAACATA TATCACTCTC TCCAGAATAA CGTCAGATTT GTGTACGGCA 2890       2900       2910       2920       2930       2940
          TCAGTGGGGA AGTTGAATAA TAATGTCCAA TGCTGCACAG TTGGTGTGCG CGAGGTCCAT
          AGTCACCCCT TCAACTTATT ATTACAGGTT ACGACGTGTC AACCACACGC GCTCCAGGTA 2950       2960       2970       2980       2990       3000
          ATTTTATCCA TTCTATATCG TGCCATACAT CCGTTCTACT GCAGTTTTTC AAAGTGACGT
          TAAAATAGGT AAGATATAGC ACGGTATGTA GGCAAGATGA CGTCAAAAAG TTTCACTGCA 3010       3020       3030       3040       3050       3060
          ATCCACCGAC ATATCCTGTT ACATTAATTA CTTCGTAATT TAAATTAGAG TGTTTATAAA
          TAGGTGGCTG TATAGGACAA TGTAATTAAT GAAGCATTAA ATTTAATCTC ACAAATATTT 3070       3080       3090       3100       3110       3120
          CGGTGTACAA ACTGCCATTG CAAGTTATGT TGCTGGTATT CAACCAGGGA GTAGTACTAT
          GCCACAGTT  TGACGGTAAC GTTCAATACA ACGACCATAA GTTGGTCCCT CATCATGATA 3130       3140       3150       3160       3170       3180
          GAATGGTAGA AAACGTTAAT GTTGGCGTAG CGCTTGACGA TGATTTTGAA AGCGTTGAAG
          CTTACCATCT TTTGCAATTA CAACCGCATC GCGAACTGCT ACTAAAACTT TCGCAACTTC 3190       3200       3210       3220       3230       3240
          TGGTTGCTGA TGCGACTGAA GAAGCGGTAG AGGGTTTGTG CGTGGTTCCA TTTGCGATAG
          ACCAACGACT ACGCTGACTT CTTCGCCATC TCCCAAACAC GCACCAAGGT AAACGCTATC 3250       3260       3270       3280       3290       3300
          CTGAAGTGCT GTTAGCATCG GTGACAGAGT TAGAAGAATT TGTGATAGTG GAGGCGGTGG
          GACTTCACGA CAATCGTAGC CACTGTCTCA ATCTTCTTAA ACACTATCAC CTCCGCCACC
```

FIG._2D-1

```
       3310                3320                3330                3340                3350                3360
AGGTAAAGGC          AATTGCACGG          ACAGGAGCAC          GTGTCATTGC          AACCTTCAGA          TATCGTAATC
TCCATTTCCG          TTAACGTGCC          TGTCCTCGTG          CACAGTAACG          TTGGAAGTCT          ATAGCATTAG
                                                            UL153
       3370                3380                3390                3400                3410                3420
ATCAGTAACG          TCCACTTAAC          CGTAAATCTC          CAGTCCATAA          CGTTATTAAA          TTTCGGTTAA
TAGTCATTGC          AGGTGAATTG          GCATTTAGAG          GTCAGGTATT          GCAATAATTT          AAAGCCAATT 3430                3440                3450                3460                3470                3480
CGGGCATTGA          TGTTTCTTCG          GACGTTGTTG          ATCTTTCTTG          CCCGTTTATT          TTCTGATATG
GCCCGTAACT          ACAAAGAAGC          CTGCAACAAC          TAGAAAGAAC          GGGCAAATAA          AAGACTATAC 3490                3500                3510                3520                3530                3540
GTCTCATAAG          ACATTTATCC          GGAAACGTTG          CTTAGTCCTC          GTGCTCAGGA          TTGTATCGAA
CAGAGTATTC          TGTAAATAGG          CCTTTGCAAC          GAATCAGGAG          CACGAGTCCT          AACATAGCTT
                                                            UL154

3550                3560                3570                3580                3590                3600
CTATGAATTC          TGATTCACTT          ATATCGTCAC          TTAATGGATG          ATATTTTTTA          TTTAGAGCTC
GATACTTAAG          ACTAAGTGAA          TATAGCAGTG          AATTACCTAC          TATAAAAAAT          AAATCTCGAG 3610                3620                3630                3640                3650                3660
GTCGGACGAA          AAATAGGAGA          ATGCAGGCTA          CACAAATTAA          TGCTAACGTC          CACGTAGTGC
CAGCCTGCTT          TTTATCCTCT          TACGTCCGAT          GTGTTTAATT          ACGATTGCAG          GTGCATCACG 3670                3680                3690                3700                3710                3720
GTCTGCCGTG          TGATGTGTTA          GAATGATTGT          TATAGCGGTA          TAAATGATCT          ATAGATGATG
CAGACGGCAC          ACTACACAAT          CTTACTAACA          ATATCGCCAT          ATTTACTAGA          TATCTACTAC 3730                3740                3750                3760                3770                3780
TGGCTGTATT          GTCTTCATAA          TTGGTCGGTT          TATGAGAAGT          GTCCCATTCG          TGCTTTGGTT
ACCGACATAA          CAGAAGTATT          AACCAGCCAA          ATACTCTTCA          CAGGGTAAGC          ACGAAACCAA
```

FIG._2D-2

```
         3790       3800       3810       3820       3830       3840
CTTCACATAC CCAGGGATTC ACGTGTGTCC CGTTTGTGTT GTTTCTAGGA TGTATTTGCA
GAAGTGTATG GGTCCCTAAG TGCACACAGG GCAAACACAA CAAAGATCCT ACATAAACGT 3850       3860       3870       3880       3890       3900
GATTARAGTT TTGATTTTGT TCGGAGGGAT GCCCAGTTTT ATAAACATGA AAGCTATATT
CTAATTTCAA AACTAAAACA AGCCTCCCTA CGGGTCAAAA TATTGTAGCT TTCGATATAA 3910       3920       3930       3940       3950       3960
TACCAGAATG AGTAAAATTA AGACCGTACA GAGATAAAGA TAAATTACGA TCGCATGTAA
ATGGTCTTAC TCATTTTAAT TCTGGCATGT CTCTATTTCT ATTTAATGCT AGCGTACATT 3970       3980       3990       4000       4010       4020
AACATAAATC ATAGTGATGT TTTAGATAAT TTGTGTGCCA CTCACATAGT ATACGCGAAT
TTGTATTTAG TATCACTACA AAATCTATTA AACACACGGT GAGTGTATCA TATGCGCTTA 4030       4040       4050       4060       4070       4080
GGAGGATTTT CAATGAATGG TTATGATATT TTCCATTTCT TATGTTGGGA TGGGTGTATT
CCTCCTAAAA GTTACTTACC AATACTATAA AAGGTAAAGA ATACAACCCT ACCCACATAA 4090       4100       4110       4120       4130       4140
TTCCGTGTGT GGATATATTA AAATGTCTAA GCCAGGCTGT TTTGTAGCAC GATGTGATGG
AAGGCACACA CCTATATAAT TTTACAGATT CGGTCCGACA AAACATCGTG CTACACTACC 4150       4160       4170       4180       4190       4200
TTAGGTTGTG TGTTATAGTA ATATTGTCTC CTTGTGCCGC CTCCAATAAT GTTTCAGATT
AATCCAACAC ACAATATCAT TATAACAGAG GAACACGGCG GAGGTTATTA CAAAGTCTAA 4210       4220       4230       4240       4250       4260
CTTTTGATAT CGTATTATTT GTACTGTTAG GCGATGAGCA AGTTGGAAGC GGTGTAGTGA
GAAAACTATA GCATAATAAA CATGACAATC CGCTACTCGT TCAACCTTCG CCACATCACT
```

FIG. _2E-1

```
                                4270        4280        4290        4300        4310        4320
                          CGTTTTCATT TGCATTTATC ATAGTAGTAG TGTTGGTTGA TAATGATATA GTTTGCAAAG
                          GCAAAAGTAA ACGTAAATAG TATCATCATC ACAACCAACT ATTACTATAT CAAACGTTTC 4330        4340        4350        4360        4370        4380
                          TCACAGTACT ATCGGTTACA TGCTGTGTCG ATGAATTCGT GTCGCCGTTT GGTGAAGTTG
                          AGTGTCATGA TAGCCAATGT ACGACACAGC TACTTAAGCA CAGCGGCAAA CCACTTCAAC 4390        4400        4410        4420        4430        4440
                          TTATTACAGT TACGTTAGTT GTAGATGTTT GGGTAGATAT GGTGGAAATA GTTGAGGTCA
                          AATAATGTCA ATGCAATCAA CATCTACAAA CCCATCTATA CCACCTTTAT CAACTCCAGT 4450        4460        4470        4480        4490        4500
                          CGTCTGTGCC TTTTACAGAG CTTGCAGTGA ATCCTGTGGA TGTGTTGACG TTGCCATTGG
                          GCAGACACGG AAAATGTCTC GAACGTCACT TAGGACACCT ACACAACTGC AACGGTAACC 4510        4520        4530        4540        4550        4560
                          AGGATGTGAA CATAGTGGTA GACATTTCGG TGGTTTGTAA CGTAGATGTC AGTTGTGTAG
                          TCCTACACTT GTATCACCAT CTGTAAAGCC ACCAAACATT GCATCTACAG TCAACACATC 4570        4580        4590        4600        4610        4620
                          TAGATATTAA GCTTGTGGGT GTAATCGACG TGGAAGTATT GGCGATAGTG GTGTTGTTAC
                          ATCTATAATT CGAACACCCA CATTAGCTGC ACCTTCATAA CCGCTATCAC CACAACAATG 4630        4640        4650        4660        4670        4680
                          ACTTGCTTTT CTGCAGAATC CAAAAAATAA TAAACATGCA TATTATTTGC GTATATGATG
                          TGAACGAAAA GACGTCTTAG GTTTTTTATT ATTTGTACGT ATAATAAACG CATATACTAC 4690        4700        4710        4720        4730        4740
                          ACTTGTTCCA CCGTCGATGT TGTGTGCGCA T.......... .......... ..........
                          TGAACAAGGT GGCAGCTACA ACACACGCGT A..........
                                                            └─ UL154
```

FIG._2E-2

| STRAIN: | TOWNE | TOLEDO | TOLEDO |
|---|---|---|---|

| PROBE: | TOLEDO | TOWNE | TOLEDO |
|---|---|---|---|

FIG._3

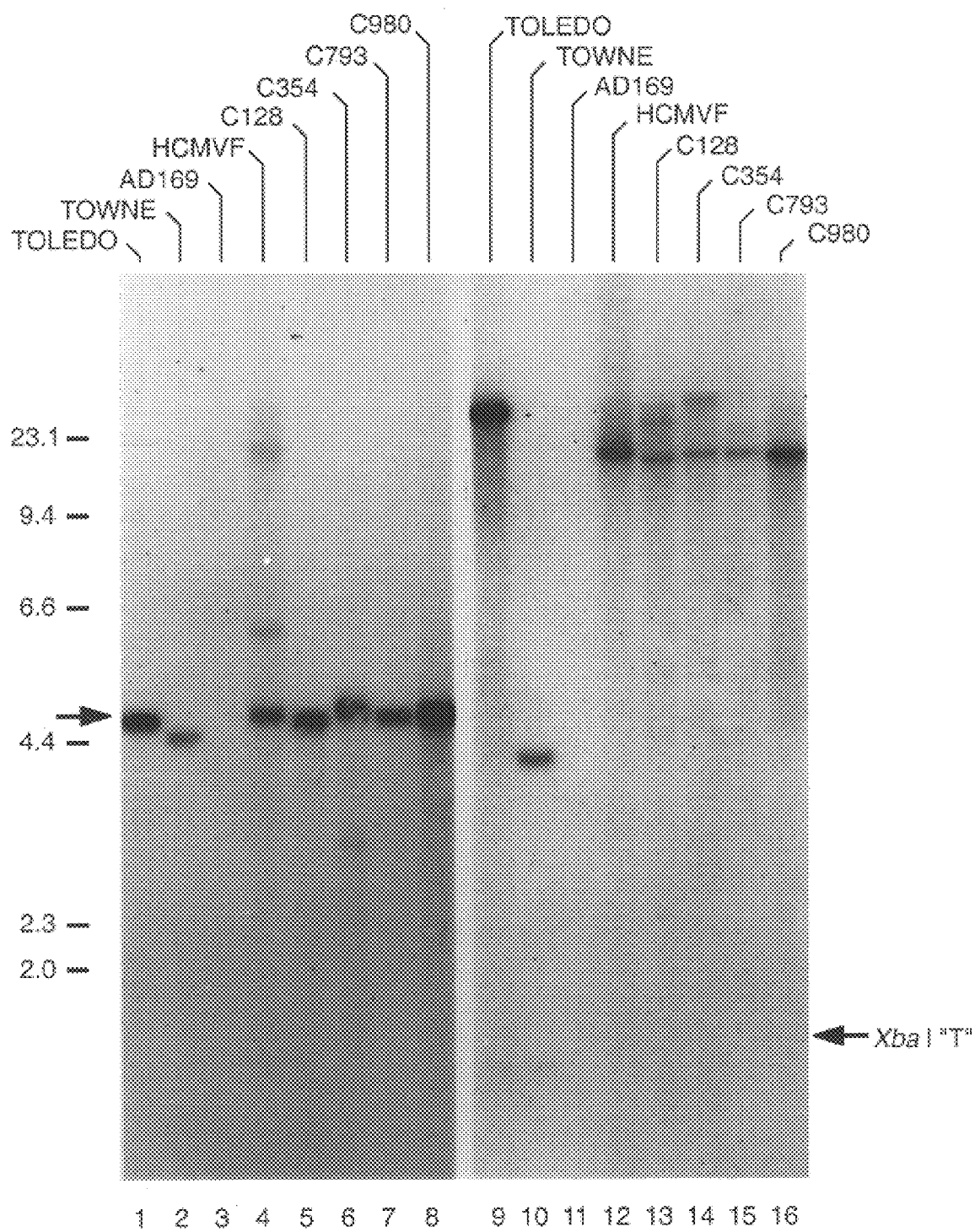
FIG._4

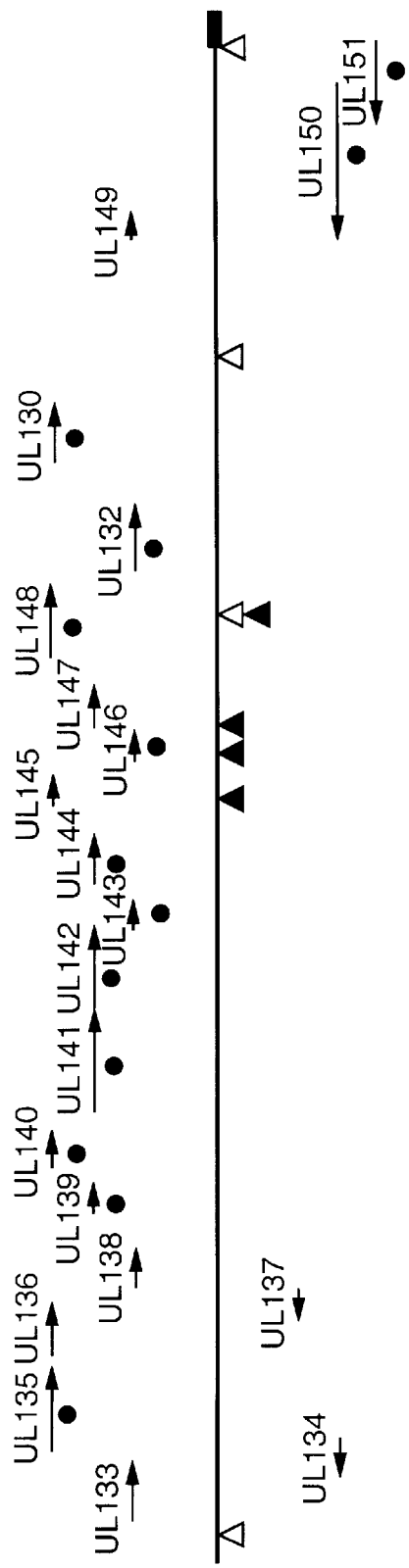
FIG._5

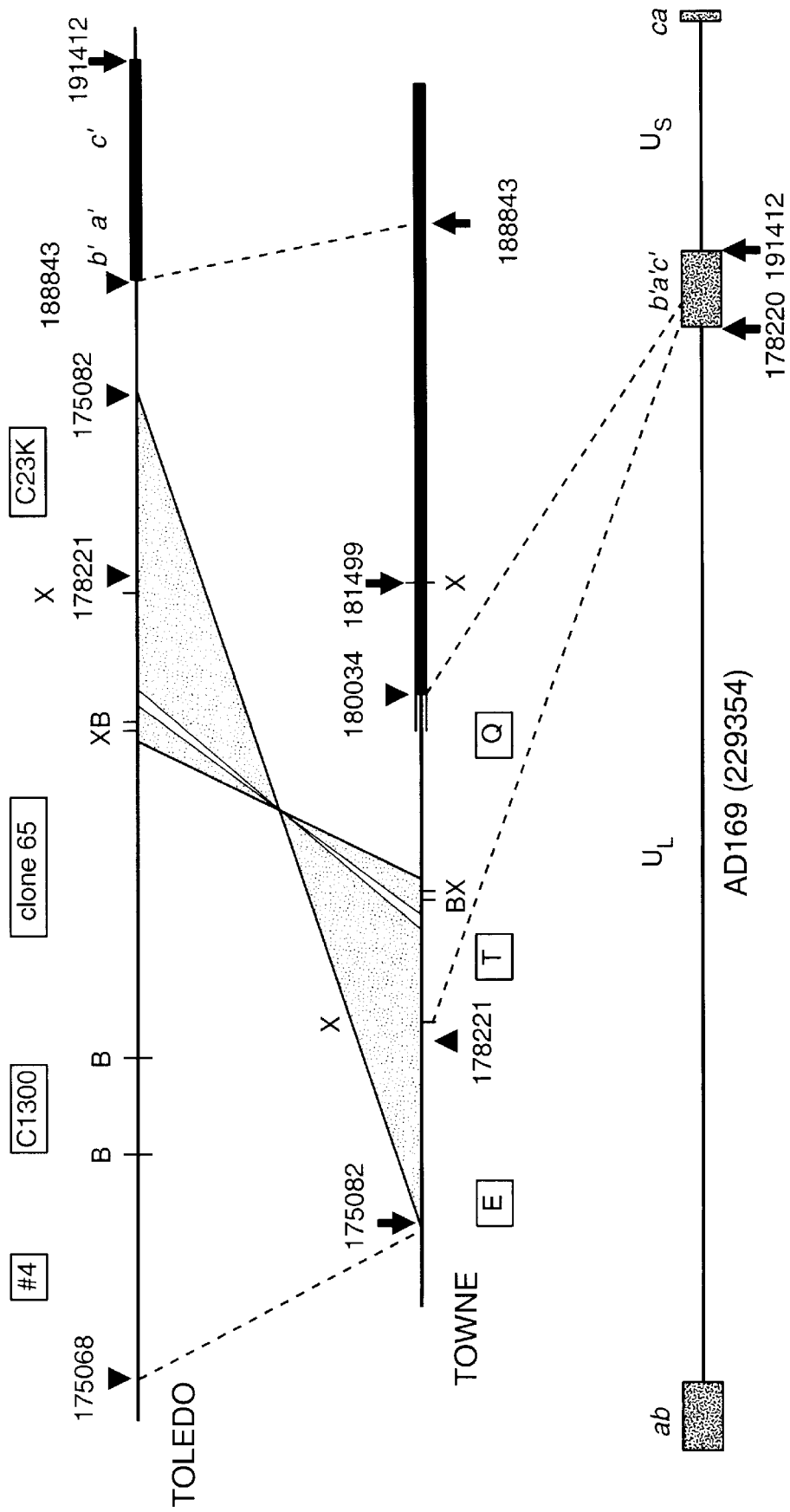
FIG._6

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 4711 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human CMV
        (B) STRAIN: Towne (ix) FEATURE:
        (A) NAME/KEY: CDS
        (B) LOCATION: complement (845..1321)
        (D) OTHER INFORMATION: /product= "UL147"

(ix) FEATURE:
        (A) NAME/KEY: CDS
        (B) LOCATION: complement (1368..1721)
        (D) OTHER INFORMATION: /product= "UL152"

(ix) FEATURE:
        (A) NAME/KEY: CDS
        (B) LOCATION: complement (2504..3337)
        (D) OTHER INFORMATION: /product= "UL153"

(ix) FEATURE:
        (A) NAME/KEY: CDS
        (B) LOCATION: complement (3515..4711)
        (D) OTHER INFORMATION: /product= "UL154"

(xi) SEQUENCE DESCRIPTION: SEQ ID NO:1:

ATCGGGCGCC AGAGCTAGAT CAGGCGTATC AAATTCCACT GCCAGGCGAC CTGATTCTAA      60

CGGTTCCACG ATCCGGGAGA GCGTTTCTAG ATATAGAGCA AAGCGTACCA CGTCTACCTG     120

CGGTGTAAAA AACTGTTGTG GGCGTTCACC GTCGTTGACC ACGTAAGCCA CGTAGAGGCC     180

AACATTTTCC ACCACGGGTT CTAGCTGCAG GCGGCACGTA AAGCTTAGAA ACGACGGCTG     240

TACGGTTTGG TTCCCGTGAA GCTGAAGCGT CACTTCCTTG CCGGGGCTCA CCGTGCTGTA     300

ACGCCGCACC GAGTCGGTCA TCTGCTCCAG ATCGGTAGAC CAGAAGGGCG TGCAATGCAT     360

ACTGTCCCAG TCGCGACACG CAGCCCAGCC TAGCTCGGTG AAGGGTCGAC GCACACCCGA     420

AAAAGTGTGC TTGAAGACCA GGGGGTCGCC TCGGTAGCTC AGTAGCCGAA CATGCACATA     480

GTCGCGGCTA CGTTGACAGA CGGCCCGTAG ACAGGCAGGA CAAGCGTGAA CAGCAAGCGC     540

AACATGCTGC GGGTTAGAAA ATGCGGCGTG CCGGCCACCG CCCGACTCAT AAACGCTACC     600

AGCATGACGT CTCAGATCAC ACAAGTGACG AGGAGCGTAC CGCAAATCAC TAGGGAAAAG     660

GCCAGCAGAG CCCGATAGTC TTGCTCTTCG CGAACGATCT CGTCCGGTTC CTCGCAGTCT     720

TCGTGGTCCA CAGAAGATGA GGAGCAGGAT TCTTCGTTAA TTTCTGCCAG GATACTAGTG     780

CTGTACCACA CCAGAGCGCT CAGCGTGCCC AGGGCTACCG CACGGTAAAA TAGGGACATG     840

ATCACCAGCG CAATCTGAAG TGGTGGTAGT TCAGTTTCTT GGCGTATTTC CAGAGAAAGG     900

CTTTGTAGGC CGTAGGGACT GGCCAGGCAC CGAACTCAAT ATTGGTAGAC ACTACGTCGT     960

AAATGCGTTG TTCCTCGTCT AAGATTAACC GAAAAAATAG CCGGTTGATG TGACGACGCA    1020

CGGCTTGCGC GTTAGGATTG AGACACTTGG TGCCCTTGTC CTTTAAAATA GCCAGCACTT    1080

CCTGACGATT GCAGCTTTCG CTCGCCGCGA TTGGCTTAAG CAATTCAGTT CCGATTGGCA    1140

GAGTATTCAA CAGAATTTGG TTGTTACAAC GACAGCGTTT GTCGTAATCT TCCAATTCTA    1200

AAAGATGGAC GGCTAGGGGA CATACGACAA ATAACATGTA TGCAGTCAAT TGCATATATC    1260

GTACCGATAA AATGTTAGTG TGCGGATTCA GAATCGGATG ATGCAACCGT CTTAGCATCA    1320

TATCGAAAAA GTATACATAT TACCGATTCA TTATAATTAG GGAATTATTT CCAACGCGGA    1380

CGTTTGTTAG TGACAGCGTT TTCTTCTACA TGCGGTCCAT TACTATCCTT TACTTTTACC    1440

AATACTCTGT GCCATGAGTT GTCTTTTTTA CCATCCAGCC ATTTGGACAA ATGATGATCG    1500

-continued

```
GGAGCTAAAC ATACAGGTTT ACCTCGAGGA GGCAATAGAT AATGTTGAGG TTTGTCACAC   1560

TCAGGAGGAT TGGGAGGGTC ACGACCAACC CAAAATAAGC CACCTATAGG ATGATGTAAA   1620

GCTTTGTGGG TACACGGACA ACGCAATTCT CTACTGTGAA CCCCATGGTA ATACATAAAT   1680

GCCATCAAAA GACTAATCAG CGAACCAAAA ATTAATCGCA TTCTAATTTT ATTAACTACG   1740

TCACTATCAG TAATTCGTAA TATCCGGTAT TCCCGGAAAA TCACTCAAAA CTGCGTCCAT   1800

GACACATCAA TTCCCGATAA GTACCCCCCT TTGAAATCGG ATCCCCCCAC ATACCAATCA   1860

ATCACACAAC ACACAGGTTT AAAAATCGAT CACACGTCAA TTAGGTTTCA AAATCGATAC   1920

TGTTTATTAT CAGGAATCTA GACTAATTCT ACAATGACAG CTCTGAATTT CTCTCTCGTC   1980

TTTCTTGTCA GGTTCTCATC ATCAATCTTC ACTTCCACCC ATCGAGGAGT CATCGTCGCT   2040

CCAAAACCCT TGGGGTCGC TGGTTGGAAA AGTCTCTGAC ACGATCCAGG CACCCCGTAC    2100

CCAGTCCGAC TGATCTAGCT TACGGAGCAT CTCAACAGGC ATGAGCTGCA GGGCCACGGC   2160

TGTCACGGCA GGGATTATTA CTACCGTTCA GGTAAACTGT ATCTCCCTGA GTTACCGTGA   2220

TGGGTCTTTC TACATGTTGA CTTTGCGTAA AAAATCGCCG GTAAAATGTT TTTTCTTGTT   2280

CATGTAAAAG TACCGGAACT AAAATGCTAG TTAGAATGGT TGCAGTTGCT ATTAGCGCGG   2340

CTAGTAACAG TAGTTTAGTG TTACATTGTA TACCCATGTT TTTAATAACT ATGAATATTC   2400

TGCTTCACAC CATAAGTGCT TAACCCACAA AAACCACACG GAGACATTAT TGGCTAAAAA   2460

TAAAAACAAA AGTTTATTGA TGTGCATGTT AGGTTTTAGT CTAAAATTCA TCTGGGTCGT   2520

ATTTGGGAAG TTTTGTATAA CGCGGTCTTC TGGGGACGCG ACGGCTACCC ATGTATAAGG   2580

CTATAAGTGC CACAGATACC ACTATACCCG CCCATACAGC ATGAATTCCC AGGGGAATGT   2640

TAGTGTTTTT TACAGTTTTT ATTACATTGT CCCACGTTCT GCTATTATGC TGGTCTGATT   2700

CCTCTTTTGT TTTACATTTA TCAGGTATAG GAGACGATGT TGCAGTTCCT GATAACACGG   2760

TTAAATAGTA GTTTTCCTTT TTACCGTCAC TGTAACGTTG CAAAACGTAT TTTCCAGCGT   2820

GTTCGGTAGT TACGTTGTAT ATAGTGAGAG AGGTCTTATT GCAGTCTAAA CACATGCCGT   2880

TCAGTGGGA AGTTGAATAA TAATGTCCAA TGCTGCACAG TTGGTGTGCG CGAGGTCCAT    2940

ATTTTATCCA TTCTATATCG TGCCATACAT CCGTTCTACT GCAGTTTTTC AAAGTGACGT   3000

ATCCACCGAC ATATCCTGTT ACATTAATTA CTTCGTAATT TAAATTAGAG TGTTTATAAA   3060

CGGTGTACAA ACTGCCATTG CAAGTTATGT TGCTGGTATT CAACCAGGGA GTAGTACTAT   3120

GAATGGTAGA AAACGTTAAT GTTGGCGTAG CGCTTGACGA TGATTTTGAA AGCGTTGAAG   3180

TGGTTGCTGA TGCGACTGAA GAAGCGGTAG AGGGTTTGTG CGTGGTTCCA TTTGCGATAG   3240

CTGAAGTGCT GTTAGCATCG GTGACAGAGT TAGAAGAATT TGTGATAGTG GAGGCGGTGG   3300

AGGTAAAGGC AATTGCACGG ACAGGAGCAC GTGTCATTGC AACCTTCAGA TATCGTAATC   3360

ATCAGTAACG TCCACTTAAC CGTAAATCTC CAGTCCATAA CGTTATTAAA TTTCGGTTAA   3420

CGGGCATTGA TGTTTCTTCG GACGTTGTTG ATCTTTCTTG CCCGTTTATT TTCTGATATG   3480

GTCTCATAAG ACATTTATCC GGAAACGTTG CTTAGTCCTC GTGCTCAGGA TTGTATCGAA   3540

CTATGAATTC TGATTCACTT ATATCGTCAC TTAATGGATG ATATTTTTTA TTTAGAGCTC   3600

GTCGGACGAA AAATAGGAGA ATGCAGGCTA CACAAATTAA TGCTAACGTC CACGTAGTGC   3660

GTCTGCCGTG TGATGTGTTA GAATGATTGT TATAGCGGTA TAAATGATCT ATAGATGATG   3720

TGGCTGTATT GTCTTCATAA TTGGTCGGTT TATGAGAAGT GTCCCATTCG TGCTTTGGTT   3780

CTTCACATAC CCAGGGATTC ACGTGTGTCC CGTTTGTGTT GTTTCTAGGA TGTATTTGCA   3840
```

-continued

```
GATTAAAGTT TTGATTTTGT TCGGAGGGAT GCCCAGTTTT ATAACATCGA AAGCTATATT    3900

TACCAGAATG AGTAAAATTA AGACCGTACA GAGATAAAGA TAAATTACGA TCGCATGTAA    3960

AACATAAATC ATAGTGATGT TTTAGATAAT TTGTGTGCCA CTCACATAGT ATACGCGAAT    4020

GGAGGATTTT CAATGAATGG TTATGATATT TTCCATTTCT TATGTTGGGA TGGGTGTATT    4080

TTCCGTGTGT GGATATATTA AAATGTCTAA GCCAGGCTGT TTTGTAGCAC GATGTGATGG    4140

TTAGGTTGTG TGTTATAGTA ATATTGTCTC CTTGTGCCGC CTCCAATAAT GTTTCAGATT    4200

CTTTTGATAT CGTATTATTT GTACTGTTAG GCGATGAGCA AGTTGGAAGC GGTGTAGTGA    4260

CGTTTTCATT TGCATTTATC ATAGTAGTAG TGTTGGTTGA TAATGATATA GTTTGCAAAG    4320

TCACAGTACT ATCGGTTACA TGCTGTGTCG ATGAATTCGT GTCGCCGTTT GGTGAAGTTG    4380

TTATTACAGT TACGTTAGTT GTAGATGTTT GGGTAGATAT GGTGGAAATA GTTGAGGTCA    4440

CGTCTGTGCC TTTTACAGAG CTTGCAGTGA ATCCTGTGGA TGTGTTGACG TTGCCATTGG    4500

AGGATGTGAA CATAGTGGTA GACATTTCGG TGGTTTGTAA CGTAGATGTC AGTTGTGTAG    4560

TAGATATTAA GCTTGTGGGT GTAATCGACG TGGAAGTATT GGCGATAGTG GTGTTGTTAC    4620

ACTTGCTTTT CTGCAGAATC CAAAAAATAA TAAACATGCA TATTATTTGC GTATATGATG    4680

ACTTGTTCCA CCGTCGATGT TGTGTGCGCA T                                  4711
```

(2) INFORMATION FOR SEQ ID NO:2:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO:2:

```
Met Met Leu Arg Arg Leu His His Pro Ile Leu Asn Pro His Thr Asn
 1               5                  10                  15

Ile Leu Ser Val Arg Tyr Met Gln Leu Thr Ala Tyr Met Leu Phe Val
            20                  25                  30

Val Cys Pro Leu Ala Val His Leu Leu Glu Leu Glu Asp Tyr Asp Lys
        35                  40                  45

Arg Cys Arg Cys Asn Asn Gln Ile Leu Leu Asn Thr Leu Pro Ile Gly
    50                  55                  60

Thr Glu Leu Leu Lys Pro Ile Ala Ala Ser Glu Ser Cys Asn Arg Gln
65                  70                  75                  80

Glu Val Leu Ala Ile Leu Lys Asp Lys Gly Thr Lys Cys Leu Asn Pro
                85                  90                  95

Asn Ala Gln Ala Val Arg Arg His Ile Asn Arg Leu Phe Phe Arg Leu
            100                 105                 110

Ile Leu Asp Glu Glu Gln Arg Ile Tyr Asp Val Ser Thr Asn Ile
        115                 120                 125

Glu Phe Gly Ala Trp Pro Val Pro Thr Ala Tyr Lys Ala Phe Leu Trp
    130                 135                 140

Lys Tyr Ala Lys Lys Leu Asn Tyr His His Phe Arg Leu Arg Trp
145                 150                 155
```

(2) INFORMATION FOR SEQ ID NO:3:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:3:

```
Met Arg Leu Ile Phe Gly Ser Leu Ile Ser Leu Leu Met Ala Phe Met
 1               5                  10                  15

Tyr Tyr His Gly Val His Ser Arg Glu Leu Arg Cys Pro Cys Thr His
            20                  25                  30

Lys Ala Leu His His Pro Ile Gly Gly Leu Phe Trp Val Gly Arg Asp
        35                  40                  45

Pro Pro Asn Pro Pro Glu Cys Asp Lys Pro Gln His Tyr Leu Leu Pro
    50                  55                  60

Pro Arg Gly Lys Pro Val Cys Leu Ala Pro Asp His His Leu Ser Lys
65                  70                  75                  80

Trp Leu Asp Gly Lys Lys Asp Asn Ser Trp His Arg Val Leu Val Lys
                85                  90                  95

Val Lys Asp Ser Asn Gly Pro His Val Glu Glu Asn Ala Val Thr Asn
            100                 105                 110

Lys Arg Pro Arg Trp Lys
        115
```

(2) INFORMATION FOR SEQ ID NO:4:

(i) SEQUENCE CHARACTERISTICS:
        (A) LENGTH: 278 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Arg Ala Pro Val Arg Ala Ile Ala Phe Thr Ser Thr Ala Ser
 1               5                  10                  15

Thr Ile Thr Asn Ser Ser Asn Ser Val Thr Asp Ala Asn Ser Thr Ser
            20                  25                  30

Ala Ile Ala Asn Gly Thr Thr His Lys Pro Ser Thr Ala Ser Ser Val
        35                  40                  45

Ala Ser Ala Thr Thr Ser Thr Leu Ser Lys Ser Ser Ser Ser Ala Thr
    50                  55                  60

Pro Thr Leu Thr Phe Ser Thr Ile His Ser Thr Thr Pro Trp Leu Asn
65                  70                  75                  80

Thr Ser Asn Ile Thr Cys Asn Gly Ser Leu Tyr Thr Val Tyr Lys His
                85                  90                  95

Ser Asn Leu Asn Tyr Glu Val Ile Asn Val Thr Gly Tyr Val Gly Gly
            100                 105                 110

Tyr Val Thr Leu Lys Asn Cys Ser Arg Thr Asp Val Trp His Asp Ile
        115                 120                 125

Glu Trp Ile Lys Tyr Gly Pro Arg Ala His Gln Leu Cys Ser Ile Gly
    130                 135                 140

His Tyr Tyr Ser Thr Ser Pro Leu Asn Gly Met Cys Leu Asp Cys Asn
145                 150                 155                 160

Lys Thr Ser Leu Thr Ile Tyr Asn Val Thr Thr Glu His Ala Gly Lys
                165                 170                 175

Tyr Val Leu Gln Arg Tyr Ser Asp Gly Lys Lys Glu Asn Tyr Tyr Leu
            180                 185                 190

Thr Val Leu Ser Gly Thr Ala Thr Ser Ser Pro Ile Pro Asp Lys Cys
        195                 200                 205
```

```
Lys Thr Lys Glu Glu Ser Asp Gln His Asn Ser Arg Thr Trp Asp Asn
    210                 215                 220

Val Ile Lys Thr Val Lys Asn Thr Asn Ile Pro Leu Gly Ile His Ala
225                 230                 235                 240

Val Trp Ala Gly Ile Val Ser Val Ala Leu Ile Ala Leu Tyr Met
                245                 250                 255

Gly Ser Arg Arg Val Pro Arg Arg Pro Arg Tyr Thr Lys Leu Pro Lys
            260                 265                 270

Tyr Asp Pro Asp Glu Phe
            275

(2) INFORMATION FOR SEQ ID NO:5:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:5:

Met Arg Thr Gln His Arg Arg Trp Asn Lys Ser Ser Tyr Thr Gln Ile
1               5                   10                  15

Ile Cys Met Phe Ile Ile Phe Trp Ile Leu Gln Lys Ser Lys Cys Asn
                20                  25                  30

Asn Thr Thr Ile Ala Asn Thr Ser Thr Ser Ile Thr Pro Thr Ser Leu
            35                  40                  45

Ile Ser Thr Thr Gln Leu Thr Ser Thr Leu Gln Thr Thr Glu Met Ser
    50                  55                  60

Thr Thr Met Phe Thr Ser Ser Asn Gly Asn Val Asn Thr Ser Thr Gly
65                  70                  75                  80

Phe Thr Ala Ser Ser Val Lys Gly Thr Asp Val Thr Ser Thr Ile Ser
                85                  90                  95

Thr Ile Ser Thr Gln Thr Ser Thr Thr Asn Val Thr Val Ile Thr Thr
            100                 105                 110

Ser Pro Asn Gly Asp Thr Asn Ser Ser Thr Gln His Val Thr Asp Ser
            115                 120                 125

Thr Val Thr Leu Gln Thr Ile Ser Leu Ser Thr Asn Thr Thr Thr Met
130                 135                 140

Ile Asn Ala Asn Glu Asn Val Thr Thr Pro Leu Pro Thr Cys Ser Ser
145                 150                 155                 160

Pro Asn Ser Thr Asn Asn Thr Ile Ser Lys Glu Ser Glu Thr Leu Leu
                165                 170                 175

Glu Ala Ala Gln Gly Asp Asn Ile Thr Ile Thr His Asn Leu Thr Ile
            180                 185                 190

Thr Ser Cys Tyr Lys Thr Ala Trp Leu Arg His Phe Asn Ile Ser Thr
        195                 200                 205

His Gly Lys Tyr Thr His Pro Asn Ile Arg Asn Gly Lys Tyr His Asn
    210                 215                 220

His Ser Leu Lys Ile Leu His Ser Arg Ile Leu Cys Glu Trp His Thr
225                 230                 235                 240

Asn Tyr Leu Lys His His Tyr Asp Leu Cys Phe Thr Cys Asp Arg Asn
                245                 250                 255

Leu Ser Leu Ser Leu Tyr Gly Leu Asn Phe Thr His Ser Gly Lys Tyr
            260                 265                 270
```

```
Ser Phe Arg Cys Tyr Lys Thr Gly His Pro Ser Glu Gln Asn Gln Asn
        275                 280                 285

Phe Asn Leu Gln Ile His Pro Arg Asn Asn Thr Asn Gly Thr His Val
        290                 295                 300

Asn Pro Trp Val Cys Glu Glu Pro Lys His Glu Trp Asp Thr Ser His
305                 310                 315                 320

Lys Pro Thr Asn Tyr Glu Asp Asn Thr Ala Thr Ser Ser Ile Asp His
                325                 330                 335

Leu Tyr Arg Tyr Asn Asn His Ser Asn Thr Ser His Gly Arg Arg Thr
            340                 345                 350

Thr Trp Thr Leu Ala Leu Ile Cys Val Ala Cys Ile Leu Leu Phe Phe
        355                 360                 365

Val Arg Arg Ala Leu Asn Lys Lys Tyr His Pro Leu Ser Asp Asp Ile
    370                 375                 380

Ser Glu Ser Glu Phe Ile Val Arg Tyr Asn Pro Glu His Glu Asp
385                 390                 395
```

(2) INFORMATION FOR SEQ ID NO:6:

(i) SEQUENCE CHARACTERISTICS:
      (A) LENGTH: 18318 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Human CMV
      (B) STRAIN: Toledo (ix) FEATURE:
      (A) NAME/KEY: CDS
      (B) LOCATION: 511..1281
      (D) OTHER INFORMATION: /product = "UL133"

(ix) FEATURE:
      (A) NAME/KEY: CDS
      (B) LOCATION: 1401..2384
      (D) OTHER INFORMATION: /product = "UL135"

(ix) FEATURE:
      (A) NAME/KEY: CDS
      (B) LOCATION: 2478..3197
      (D) OTHER INFORMATION: /product = "UL136"

(ix) FEATURE:
      (A) NAME/KEY: CDS
      (B) LOCATION: 3283..3789
      (D) OTHER INFORMATION: /product = "UL138"

(ix) FEATURE:
      (A) NAME/KEY: CDS
      (B) LOCATION: 4355..4759
      (D) OTHER INFORMATION: /product = "UL139"

(ix) FEATURE:
      (A) NAME/KEY: CDS
      (B) LOCATION: 4944..5285
      (D) OTHER INFORMATION: /product = "UL140"

(ix) FEATURE:
      (A) NAME/KEY: CDS
      (B) LOCATION: 5558..6832
      (D) OTHER INFORMATION: /product = "UL141"

(ix) FEATURE:

(A) NAME/KEY: CDS
                (B) LOCATION: 6908..7825
                (D) OTHER INFORMATION: /product = "UL142"

(ix) FEATURE:
                (A) NAME/KEY: CDS
                (B) LOCATION: 7813..8088
                (D) OTHER INFORMATION: /product = "UL143"

(ix) FEATURE:
                (A) NAME/KEY: CDS
                (B) LOCATION: 8468..8995
                (D) OTHER INFORMATION: /product = "UL144"

(ix) FEATURE:
                (A) NAME/KEY: CDS
                (B) LOCATION: 9327..9626
                (D) OTHER INFORMATION: /product = "UL145"

(ix) FEATURE:
                (A) NAME/KEY: CDS
                (B) LOCATION: 9910..10260
                (D) OTHER INFORMATION: /product = "UL146"

(ix) FEATURE:
                (A) NAME/KEY: CDS
                (B) LOCATION: 10328..10804
                (D) OTHER INFORMATION: /product = "UL147"

(ix) FEATURE:
                (A) NAME/KEY: CDS
                (B) LOCATION: 11106..12053
                (D) OTHER INFORMATION: /product = "UL148"

(ix) FEATURE:
                (A) NAME/KEY: CDS
                (B) LOCATION: 12133..12942
                (D) OTHER INFORMATION: /product = "UL132"

(ix) FEATURE:
                (A) NAME/KEY: CDS
                (B) LOCATION: 13569..14210
                (D) OTHER INFORMATION: /product = "UL130"

(ix) FEATURE:
                (A) NAME/KEY: CDS
                (B) LOCATION: 16216..16581
                (D) OTHER INFORMATION: /product = "UL149"

(ix) FEATURE:
                (A) NAME/KEY: CDS
                (B) LOCATION: 1004..1528
                (D) OTHER INFORMATION: /product = "UL134"

(ix) FEATURE:
                (A) NAME/KEY: CDS
                (B) LOCATION: 3063..3350
                (D) OTHER INFORMATION: /product = "UL137"

(ix) FEATURE:
                (A) NAME/KEY: CDS
                (B) LOCATION: 16337..18262
                (D) OTHER INFORMATION: /product = "UL150"

(ix) FEATURE:
                (A) NAME/KEY: CDS
                (B) LOCATION: 17752..18759
                (D) OTHER INFORMATION: /product = "UL151"

(xi) SEQUENCE DESCRIPTION: SEQ ID NO:6:

CGCTGTAGGG ATAAATAGTG CGATGGCGTT TGTGGGAGAA CGCAGTAGCG ATGGGTTGCG      60

ACGTGCACGA TCCTTCGTGG CAATGCCAAT GGGGCGTTCC CACGATTATC GTGGCCTGGA     120

TAACATGCGC GGCTTTAGGA ATTTGGTGTT TGGCGGGATC GTCGGCGGAT GTCTCTTCGG     180

GACCCGGCAT CGCAGCCGTA GTCGGCTGTT CTGTTTTCAT GATTTTCCTC TGCGCGTATC     240

```
-continued

TCATCCGTTA CCGGGAATTC TTCAAAGACT CCGTAATCGA CCTCCTTACC TGCCGATGGG      300

TTCGCTACTG CAGCTGCAGC TGTAAGTGCA GCTGCAAATG CATCTCGGGC CCCTGTAGCC      360

GCTGCTGTTC AGCGTGTTAC AAGGAGACGA TGATTTACGA CATGGTCCAA TACGGTCATC      420

GACGGCGTCC CGGACACGGC GACGATCCCG ACAGGGTGAT CTGCGAGATA GTCGAGAGTC      480

CCCCGGTTTC GGCGCCGACG GTGTCCGTCC CCCCGCCGTC GGAGGAGTCC CACCAGCCCG      540

TCATCCCACC GCAGCCGCCA GCACCGACAT CGGAACCCAA ACCGAAGAAA GGTAGGGCGA      600

AAGATAAACC GAAGGGTAGA CCGAAAGACA AACCTCCGTG CGAACCGACG GTGAGTTCAC      660

AACCACCGTC GCAGCCGACG GCAATGCCCG GCGGTCCGCC CGACGCGCCT CCCCCCGCCA      720

TGCCGCAGAT GCCACCCGGC GTGGCCGAGG CGGTACAAGC TGCCGTGCAG GCGGCCGTGG      780

CCGCGGCTCT ACAACAACAG CAGCAGCATC AGACCGGAAC GTAACCCGCC CCCGGTGCGA      840

TAAGGAATTT TCCGACTTGG CGCACATCTC CTTCCTCAAT GTTTGGACAA TAAACACATT      900

CCTTGCCAAA AAATGACGTT TCCAGAAATC CAAGGCATAA ATGTCCGTAC ACCGGCCCTT      960

CCCAACACGG AGTTTGAGAT TCCAAGCAGG AGAGAAGATC ATGGTGTGGA TATGGCTCGG     1020

CATCGGGCTC CTCGGCGGTA CCGGACTGGC TTCCCTGGTC CTGGCCATTT CCTTATTTAC     1080

CCAGCGCCGA GGCCGCAAGC GATCCGACGA GACTTCGTCG CGAGGCCGGC TCCCGGGTGC     1140

TGCTTCTGAT AAGCGTGGTG CCTGCGCGTG CTGCTATCGA AATCCGAAAG AAGACGTCGT     1200

CGAGCCGCTG GATCTGGAAC TGGGGCTCAT GCGGGTGGAC ACCCACCCGC CGACGCCGCA     1260

GGTGCCGCGG TGTACGTCGC TCTACATAGG AGAGGATGGT CTGCCGATAG ATAAACCCGA     1320

GTTTCCTCCG GCGCGGTTCG AGATCCCCGA CGTATCCACG CCGGGAACGC CGACCAGCAT     1380

CGGCCGATCT CCGTCGCATT GCTCCTCGTC GAGCTCTTTG TCGTCCTCGA CCAGCGTCGA     1440

CACGGTGCTG TATCAGCCGC CGCCATCCTG GAAGCCACCT CCGCCGCCCG GGCGCAAGAA     1500

GCGGCCGCCT ACGCCGCCGG TCCGGGCCCC CACCACGCGG CTGTCGTCGC ACAGACCCCC     1560

GACGCCGATA CCCGCGCCGC GTAAGAACCT GAGCACGCCG CCCACCAAGA AAACGCCGCC     1620

GCCCACGAAA CCCAAGCCGG TCGGCTGGAC ACCGCCGGTG ACACCCAGGC CCTTCCCGAA     1680

AACGCCGACG CCACAAAAGC CGCCGCGGAA TCCGAGACTA CCGCGCACCG TCGGTCTGGA     1740

GAATCTCTCG AAGGTGGGAC TCTCGTGTCC CTGTCCCCGA CCCCGCACGC CGACGGAGCC     1800

GACCACGCTG CCTATCGTGT CGGTTTCCGA GCTAGCCCCG CCTCCTCGAT GGTCGGACAT     1860

CGAGGAACTC TTGGAACAGG CGGTGCAGAG CGTCATGAAG GACGCCGAGT CGATGCAGAT     1920

GACCTGAGAC CGAAAGAGCG AGCGCGTCCG TTGTACAGTT GTATAGCAGC ACACGCCTTC     1980

CCTCTTTTTC ACCGCAGCTA AGAGAGAAA AGAGAGTATG TCAGTCAAGG GCGTGGAGAT     2040

GCCAGAAATG ACGTGGGACT TGGACGTTAG AAATAAATGG CGGCGTCGAA AGGCCCTGAG     2100

TCGCATTCAC CGGTTCTGGG AATGTCGGCT ACGGGTGTGG TGGCTGAGTG ACGCCGGCGT     2160

AAGAGAAACC GACCCACCGC GTCCCCGACG CCGCCCGACT TGGATGACCG CGGTGTTTCA     2220

CGTTATCTGT GCCGTTTTGC TTACGCTTAT GATTATGGCC ATCGGCGCGC TCATCGCGTA     2280

CTTAAGATAT TACCACCAGG ACAGTTGGCG AGACATGCTC CACGATCTAT TTTGCGGCTG     2340

TCATTATCCC GAGAAGTGCC GTCGGCACCA CGAGCGGCAG AGAAGGAGAC GGCAAGCCAT     2400

GGATGTGCCC GACCCGGAAC TCGGCGACCC GGCCCGCCGG CCGTTGAACG GAGCTATGTA     2460

CTACGGCAGC GGCTGTCGCT TCGACACGGT GGAAATGGTG GACGAGACGA GACCCGCGCC     2520

GCCGGCGCTG TCATCGCCCG AAACCGGCGA CGATAGCAAC GACGACGCGG TTGCCGGCGG     2580

AGGTGCTGGC GGGGTAACAT CACCCGCGAC TCGTACGACG TCGCCGAACG CACTGCTGCC     2640
```

-continued

```
AGAATGGATG GATGCGGTGC ATGTGGCGGT CCAAGCCGCC GTTCAAGCGA CCGTGCAAGT    2700

AAGTGGCCCG CGGGAGAACG CCGTATCTCC CGCTACGTAA GAGGGTTGAG GGGGCCGTTC    2760

CCGCGCGAGT GCTGTACAAA AGAGAGAGAC TGGGACGTAG ATCCGGACAG AGGACGGTCA    2820

CCATGGACGA TCTGCCGCTG AATGTCGGGT TACCCATCAT CGGCGTGATG CTCGTGCTGA    2880

TCGTGGCCAT CCTCTGCTAT CTGGCTTACC ACTGGCACGA CACCTTCAAA CTGGTGCGCA    2940

TGTTTCTGAG CTACCGCTGG CTGATCCGCT GTTGCGAGCT GTACGGGGAG TACGAGCGCC    3000

GGTTCGCGGA CCTGTCGTCT CTGGGCCTCG GCGCCGTACG GCGGGAGTCG GACAGACGAT    3060

ACCGTTTCTC CGAACGGCCC GACGAGATCT TGGTCCGTTG GGAGGAAGTG TCTTCCCAGT    3120

GCAGCTACGC GTCGTCGCGG ATAACAGACC GCCGTGTGGG TTCATCGTCT TCGTCGTCGG    3180

TCCACGTCGC TAGCCAGAGA AACAGCGTGC CTCCGCCGGA CATGGCGGTG ACGGCGCCGC    3240

TGACCGACGT CGATCTGTTG AAACCCGTGA CGGGATCCGC GACGCAGTTC ACCACCGTAG    3300

CCATGGTACA TTATCATCAA GAGTACACGT GAATGAGAAA AGAAAAAAG AGGGGAGCGG    3360

ATCGCGATAA TGTCGCTTTG ACATTCTCTG CTCGATCTAC TCAGCGTCTG CACGAAACGG    3420

CATCCGCACG GAGGCGAGCC CAAGCGTATC TGCAGCAAGC GGTTCTTTCC CTCGGTGATG    3480

GTGGCAGCAT CGGTGGCGGG AGCTTGTTCG GACGATGGAC GGTGAGGAGT CCCTGGCGAT    3540

CAGGCGGCTC CCGGGTGTGG AGTTCAACGG GTGGTAATGG TGGCGGTGAT CGGTGTTAGA    3600

AAACGGTGGC CCTGGCAAAC ATATATCTAC TGTAAACCCT CTGCTCTGTT AATAAAAAGC    3660

ACACTTTTCA CATGAGTTCG TAATTTTATT GTGTAGTGGA AATTTTTACG TCATTGGGAA    3720

ACCCCAGAAT GAAAGAGTAT AATGTGCATA TCACCGGGGG TTCCCTGTCA GTACGAATGT    3780

ACACAACGCG GGTTACATTA CGATAAACTT TCCGGTAAAA CGATGCCGAT ACAGCGTGTA    3840

TAACGCTGAT TGTTACGACA AACGAGTTGG TATATCCATT ATATAGTAAC GAACATGCTG    3900

TGGATATTAG TTTTATTTGC ACTCGCCGCA TCGGCGAGTG AAACCACTAC AGGTACCAGC    3960

TCTAATTCCA GTCAATCTAC TAGTGCTACC GCCAACACGA CCGTATCGAC ATGTATTAAT    4020

GCCTCTAACG GCAGTAGCTG GACAGTACCA CAGCTCGCGC TGCTTGCCGC TAGCGGCTGG    4080

ACATTATCTG GACTCCTTCT CTTATTTACC TGCTGCTTTT GCTGCTTTTG GCTAGTACGT    4140

AAAATCTGCA GCTGCTGCGG CAACTCCTCC GAGTCAGAGA GCAAAACAAC CCACGCGTAC    4200

ACCAATGCCG CATTCACTTC TTCCGACGCA ACGTTACCCA TGGGCACTAC AGGGTCGTAC    4260

ACTCCCCCAC AGGACGGCTC ATTTCCACCT CCGCCTCGGT GACGTAGGCT AAACCGAAAC    4320

CCACGTTGAA CCTAACGCGG TTTCGGAAGG CCTGAGACGT CACTTTCACA ATGACGTCCG    4380

TATACACGTT CATCATAAAA CACCGTAGAG GCTAAGGCTT CGGTAGGGAG AGACCTCAAC    4440

TGTTCCTGAT GAGCACCCGT GCTCTCATCT CTTCAGACTT GTCATGACCC CCGCTCAGAC    4500

TAACGCGACT ACCACCGTGC ACCCGCACGA CGCAAAAAAC GGCAGCGGCG GTAGTGCCCT    4560

GCCGACCCTC GTCGTTTTCG GCTTTATCGT TACGCTACTT TTCTTTCTCT TTATGCTCTA    4620

CTTTTGGAAC AACGACGTGT TCCGTAAGCT GCTCCGTGCG CTTGGATCCA GCGCTGTTGC    4680

GACCGCTTCG ACGCGTGGCA AGACGAGGTC ATCTACCGTC GTCCATCACG TCGTTCCCAG    4740

AGCGACGACG AGAGTCGTAC TAACAGCGTG TCATCGTACG TTCTTTTATC ACCCGCGTCC    4800

GATGGCGGTT TTGACAACCC GGCACTGACA GAGGCCGTCG ACAGCGTGGA CGACTGGGCG    4860

ACCACCTCGG TTTTCTACGC CACGTCCGAC GAAACGGCGG ACGCCGAGCG CCGAGACTCG    4920

CAGCAACTGC TCATCGAGCT TCCGCCGGAG CCGCTCCCGC CCGACGTGGT GGCGGCCATG    4980
```

-continued

```
CAGAAAGCAG TGAAACGCGC TGTACAGAAC GCACTACGAC ACAGCCACGA CTCTTGGCAG      5040

CTTCATCAGA CCCTGTGACG CCAGATGAAC GTTCCTTCTT AAACATCCGA GGTAGCAATG      5100

AGACAGGTCG CGTACCGCCG GCGACGCGAG AGTTCCTGCG CGGTGCTGGT CCACCACGTC      5160

GGCCGCGACG GCGACGGCGA GGGGGAGGCA GCAAAAAAGA CCTGCAAAAA AACCGGACGC      5220

TCAGTTGCGG GCATCCCGGG CGAGAAGCTG CGTCGCACGG TGGTCACCAC CACGCCGGCC      5280

CGACGTTTGA GCGGCCGACA CACGGAGCAG GAGCAGGCGG GCATGCGTCT CTGTGAAAAA      5340

GGGAAGAAAA GAATCATCAT GTGCCGCCGG GAGTCGCTCC GAACTCTGCC GTGGCTGTTC      5400

TGGGTGCTGT TGAGCTGCCC GCGACTCCTC GAATATTCTT CCTCTTCGTT CCCCTTCGCC      5460

ACCGCTGACA TTGCCGAAAA GATGTGGGCC GAGAATTATG AGACCACGTC GCCGGCGCCG      5520

GTGTTGGTCG CCGAGGGAGA GCAAGTTACC ATCCCTGCA CGGTCATGAC ACACTCCTGG      5580

CCCATGGTCT CCATTCGCGC ACGTTTCTGT CGTTCCCACG ACGGCAGCGA CGAGCTCATC      5640

CTGGACGCCG TCAAAGGCCA TCGGCTGATG AACGGACTCC AGTACCGCCT GCCGTACGCC      5700

ACTTGGAATT TCTCGCAATT GCATCTCGGC CAAATATTCT CGCTTACTTT TAACGTATCG      5760

ATGGACACAG CCGGCATGTA CGAATGCGTG CTACGCAACT ACAGCCACGG CCTCATCATG      5820

CAACGCTTCG TAATTCTCAC GCAGCTGGAG ACGCTCAGCC GGCCCGACGA ACCTTGCTGC      5880

ACACCGGCGT TAGGTCGCTA CTCGCTGGGA GACCAGATCT GGTCGCCGAC GCCCTGGCGT      5940

CTACGGAATC ACGACTGCGG AACGTACCGC GGCTTTCAAC GCAACTACTT CTATATCGGC      6000

CGCGCCGACG CCGAGGATTG CTGGAAACCC GCATGTCCGG ACGAGGAACC CGACCGCTGT      6060

TGGACAGTGA TACAGCGTTA CCGGCTCCCC GGCGACTGCT ACCGTTCGCA GCCACACCCG      6120

CCGAAATTTT TACCGGTGAC GCCAGCACCG CCGGCCGACA TAGACACCGG GATGTCTCCC      6180

TGGGCCACTC GGGGAATCGC GGCGTTTTTG GGGTTTTGGA GTATTTTTAC CGTATGTTTC      6240

CTATGCTACC TGTGTTATCT GCAGTGTTGT GGACGCTGGT GTCCCACGCC GGGAAGGGGA      6300

CGACGAGGCG GTGAGGGCTA TCGACGCCTA CCGACTTACG ATAGTTACCC CGGTGTTAGA      6360

AAGATGAAGA GGTGAGAACA CGTATAAAAT AAAAAAATAA TATGTTAAAA AATGCAGTGT      6420

GTGAAGTGTG AATAGTGTGA TTAAAATATG CGGATTGAAT GGGTGTGGTG GTTATTCGGA      6480

TACTTTGTGT CATCCGTTGG GAGCGAACGG TCATTATCCT ATCGTTACCA CTTGGAATCT      6540

AATTCATCTA CCAACGTGGT TTGCAACGGA ACATTTCCG TGTTTGTAAA CGGCACCCTA      6600

GGTGTGCGGT ATAACATTAC GGTAGGAATC AGTTCGTCTT TATTAATAGG ACACCTTACT      6660

ATACAAGTAT TGGAATCATG GTTCACACCC TGGGTCCAAA ATAAAAGTTA CAACAAACAA      6720

CCCCTAGGTG ACACTGAAAC GCTTTATAAT ATAGATAGCG AAAACATTCA TCGCGTATCT      6780

CAATATTTTC ACACAAGATG GATAAAATCT CTGCAAGAGA ATCACACTTG CGACCTCACA      6840

AACAGTACAC CTACCTATAC ATATCAAGTA AACGTGAACA ACACGAATTA CCTAACACTA      6900

ACATCCTCGG GATGGCAAGA CCGTCTAAAT TACACCGTCA TAAATAGTAC ACACTTTAAC      6960

CTCACAGAAT CGAACATAAC CAGCATTCAA AAATATCTCA ACACTACCTG CATAGAAAGA      7020

CTCCGTAACT ACACCTTGGA GTCCGTATAC ACCACAACTG TGCCTCAAAA CATAACAACA      7080

TCTCAACACG CAACAACCAC TATGCACACA ATACCTCCAA ATACAATAAC AATTCAAAAT      7140

ACAACTCAAA GCCATACTGT ACAGACGCCG TCTTTTAACG CACACATAA CGTGACGAAA      7200

CACACGTTAA ACATAAGCTA CGTTTTATCA CAAAAAACGA ATAACACAAC ATCACCGTGG      7260

ATATATGCCA TACCTATGGG CGCTACAGCC ACAATAGGCG CCGGTTTATA TATCGGGAAA      7320

CACTTTACGC CGGTTAAGTT CGTATACGAG GTATGGCGCG GTCAGTAAAG ACGATTCGGA      7380
```

-continued

```
TTCAACACAT ATACTCCCCA CGATCCTCGA ACACCTTACA GCATATGAGC AAAAAACAAG    7440

AAAGTATAGC CACAATCACA TTTGGGCGAA TAACATGCTG TCATCCACTA GCGTCTATTA    7500

ATCTAATGTT TAACGGGAGC TGTACTGTCA CCGTTAAAAT ATCCATGGGA ATCAACGGGT    7560

CAACCAACGT CCATCAGCTT GTGATTGTGC TCCATCTGGG TAACCGCTGT CAGCCTTGGC    7620

GACAGGTGTA ATCACAGCTG TCACATAACT CACGAAGCCT CCAATCACAG CAGCACACAT    7680

AGTCCTAACG CCATTGGCGT GTATAAAAGT TCGGAAAACT TGACGGTTGT ACGGCACGAC    7740

AAATCGATGT AGTGGTATGT TTTTCCAGCA GAGACCGTGT GCGGTCTCTT AGGTTCGCTA    7800

TACTGTGGCT GGAAACTGGT TACCTGTGAA GATGGCTAAC TATCCTGTTC TGTCCTGGAA    7860

AAACTTTTGG CGTCGTAGGT GGACTTTGCA GTATGCGGGT TAGTGAAGTT ATGTCATTTA    7920

TTTACGTTTA CGATCTCGTA TTACAAACCG CGGAGAGGAT GATACCGTTC GGCCCCATGA    7980

GTTATTTTTA TTCTTCCGGT AGGAGGCATG AAGCCTCTGA TAATGCTCAT CTGCTTTGCT    8040

GTGATATTAT TGCAGCTTGG AGTGACTAAA GTGTGTCAGC ATAATGAAGT GCAACTGGGC    8100

AATGAGTGCT GCCCTCCGTG TGGTTCGGGA CAAAGAGTTA CTAAAGTATG CACGGATTAT    8160

ACCAGTGTAA CGTGTACCCC TTGCCCCAAC GGCACGTATG TATCGGGACT TTACAACTGT    8220

ACCGATTGCA CTCAATGTAA CGTCACTCAG GTCATGATTC GTAACTGCAC TTCCACCAAT    8280

AATACCGTAT GCGCACCTAA GAACCATACG TACTTTTCCA CTCCAGGCGT CCAACATCAC    8340

AAACAACGAC AGCAAAATCA TACCGCACAT ATAACCGTCA AACAAGGAAA AAGCGGTCGT    8400

CATACTCTAG CCTGGTTGTC TCTCTTTATC TTTCTTGTGG GTATCATACT TTTAATTCTC    8460

TATCTTATAG CCGCCTATCG GAGTGAGAGA TGCCAACAGT GTTGCTCAAT CGGCAAAATT    8520

TTCTACCGCA CCCTGTAAGC TTCCTGTTGT TGTTTTTACA TCACGGTACG ATGAAGTCAC    8580

ACAGATAATT ACAGATGAGC TGTTCATATT TTTTATTATT TTTTCCAATT CCTGCACTAA    8640

AAAAAGAAGC ACTTTACGGA ACCGTGTCTG AGTATCTGTG GGGAATTTAG GTACTTTTTG    8700

CCGACGTCAG GAAAAATAAG TGTCGCCTAC ATAAGAGCCC GGTGCTATCG TGCTGTCACT    8760

CTTTCTTGTT GCCTTCGATG TACGGCGTCC TGGCTCATTA CTACTCCTTC ATCAGTAGCC    8820

CCAGCGTTAT GGTTAATTTT AAGCATCATA ACGCCGTGCA GCTGTTATGT GCACGGACCC    8880

GAGACGCACT GCCGGATGGG AACGTTTAAC CCATCATGCG TCGTATCACG CGAACTACGG    8940

GGCATACGCC GTGTTGATGG CTACATCGCA AAGAAAGTCC CTAGTGTTAC ATCGATACAG    9000

TGCCGTGACA GCCGTGGCCC TGCAGCTCAT GCCTGTTGAG ATCGTCCGCA AGCTAGATCA    9060

GTCGGACTGG GTGCGGGGTG CCTGGATCGT GTCAGAGACT TTTCCAACTA GCGACCCCAA    9120

AGGAGTTTGG AGCGACGATG ACTCCTCGAT GGGTGGAAGT GATGATTGAT GATGAGAACC    9180

TGACAAGAAA GACGAGAGAG AAATTTAGAG CTGTCATTGT AGAATTAGTC TAGATTCCTG    9240

ATAATAAACA GTATCGATTT TGAAACCTAA TTGACGTGTG ATCGATTTTT AAACCTCTGT    9300

GTTGTGTGAT TGATTGGTAT GTGGGGGGAT CCGATTTCAA AGGGGGGTAC TTATCGGGAA    9360

TTGATGTGTC ATGGACGCAG TTTTGAGCGA TTTTCCGGGA ATACCGGATA TTACGAATTA    9420

CTGGTAGTGA CGTAGATAAT AAAATTATAA TGCGATTAAT TTTTGGTGCG TTGATTATTT    9480

TTTTAGCATA TGTGTATCAT TATGAGGTGA ATGGAACAGA ATTACGCTGC AGATGTCTTC    9540

ATAGAAAATG GCCGCCTAAT AAAATTATAT TGGGTAATTA TTGGCTTCAT CGCGATCCCA    9600

GAGGGCCCGG ATGCGATAAA AATGAACATT TATTGTATCC AGACGGAAGG AAACCGCCTG    9660

GACCTGGAGT ATGTTTATCG CCCGATCACC TCTTCTCAAA ATGGTTAGAC AAACACAACG    9720
```

-continued

```
ATAATAGGTG GTATAATGTT AACATAACGA AATCACCAGG ACCGAGACGA ATAAATATAA      9780
CCTTGATAGG TGTTAGAGGA TAATATTTAA TGTATGTTTT CAAACAGACA AGTTCGTTAA      9840
AACAAAATAT TACAGTATGT GTTTAATATG GTGCTAACAT GGTTGCACCA TCCGGTTTCA      9900
AACTCGCATA TCAATCTGTT ATCGGTACGA CACCTGTCAT TAATCGCATA TATGTTACTT      9960
ACCATATGTC CCCTAGCCGT CCATGTTTTA GAACTAGAAG ATTACGACAG GCGCTGCCGT     10020
TGCAACAACC AAATTCTGTT GAATACCCTG CCGGTCGGAA CCGAATTGCT TAAGCCAATC     10080
GCAGCGAGCG AAAGCTGCAA TCGTCAGGAA GTGCTGGCTA TTTTAAAGGA CAAGGGAACC     10140
AAGTGTCTCA ATCCTAACGC GCAAGCCGTG CGTCGTCACA TCAACCGGCT ATTTTTTCGG     10200
TTAATCTTAG ACGAGGAACA ACGCATTTAC GACGTAGTGT CTACCAATAT TGAGTTCGGT     10260
GCCTGGCCAG TCCCTACGGC CTACAAAGCC TTTCTTTGGA AATACGCCAA GAGACTGAAC     10320
TACCACCACT TCAGACTGCG CTGGTGATCA TGTCCCTATT TTACCGTGCG GTAGCTCTGG     10380
GCACGCTAAG CGCTTTGGTG TGGTACAGCA CTAGCATCCT CGCAGAGATT AACGAAAATT     10440
CCTGCTCCTC ATCTTCTGCG GATCACGAAG ACTGCGAGGA ACCGGACGAG ATCGTTCGCG     10500
AAGAGCAAGA CTATCGGGCT CTGCTGGCCT TTTCCCTAGT GATTTGCGGT ACGCTCCTCG     10560
TCACTTGTGT GATCTGAGAC GTCATGCTGG TAGCGTTTAT GAGTCGGGCG GTGGCCGACA     10620
CGCCGCATTT CCTAACCCGC GCAGCATGTT GCGCTTGCTG TTCACGCTCG TCCTGCTGGC     10680
CCTCCACGGG CAGTCTGTCG GCGCTAGCCG CGACTATGTG CATGTTCGGC TACTGAGCTA     10740
CCGAGGCGAC CCCCTGGTCT TCAAGCACAC TTTCTCGGGT GTGCGTCGAC CCTTCACCGA     10800
GCTAGGCTGG GCTGCGTGTC GCGACTGGGA CAGTATGCAT TGCACACCCT TCTGGTCTAC     10860
CGATCTGGAG CAGATGACCG ACTCGGTGCG GCGTTACAGC ACGGTGAGCC CCGGCAAGGA     10920
AGTGACGCTT CAGCTTCACG GGAACCAAAC CGTACAGCCG TCGTTTCTAA GCTTTACGTG     10980
CCGCCTGCAG CTAGAACCCG TGGTGGAAAA TGTTGGCCTC TACGTGGCCT ACGTGGTCAA     11040
CGACGGCGAA CGCCCACAAC AGTTTTTTAC ACCGCAGGTA GACGTGGTAC GCTTTGCTCT     11100
ATATCTAGAA ACACTCTCCC GGATCGTGGA ACCGTTAGAA TCAGGTCGCC TGGCAGTGGA     11160
ATTTGATACG CCTGACCTAG CTCTGGCGCC CGATTTAGTA AGCAGCCTCT TCGTGGCCGG     11220
ACACGGCGAG ACCGACTTTT ACATGAACTG GACGCTGCGT CGCAGTCAGA CCCACTACCT     11280
GGAGGAGATG GCCTTACAGG TGGAGATTCT AAAACCCCGC GGCGTACGTC ACCGCGCTAT     11340
TATCCACCAT CCGAAGCTAC AGCCGGGCGT TGGCCTGTGG ATAGATTTCT GCGTGTACCG     11400
CTACAACGCG CGCCTGACCC GCGGCTACGT ACGATACACC CTGTCACCGA AGCGCGCTT     11460
GCCCGCAAAA GCAGAGGGTT GGCTGGTGTC ACTAGACAGA TTCATCGTGC AGTACCTCAA     11520
CACATTGCTG ATTACAATGA TGGCGGCGAT ATGGGCTCGC GTTTTGATAA CCTACCTGGT     11580
GTCGCGGCGT CGGTAGAGGC TTGCGGAAAC CACGTCCTCG TCACACGTCG TTCGCGGACA     11640
TAGCAAGAAA TCCACGTCGC CACATCTCGA GAATGCCGGC CTTGCGGGGT CCCCTTCGCG     11700
CAACATTCCT GGCCCTGGTC GCGTTCGGGT TGCTGCTTCA GATAGACCTC AGCGACGCTA     11760
CGAATGTGAC CAGCAGCACA AAAGTCCCTA CTAGCACCAG CAACAGAAAT AACGTCGACA     11820
ACGCCACGAG TAGCGGACCC ACAACCGGGA TCAACATGAC CACCACCCAC GAGTCTTCCG     11880
TTCACAACGT GCGCAATAAC GAGATCATGA AAGTGCTGGC TATCCTCTTC TACATCGTGA     11940
CAGGCACCTC CATTTTCAGC TTCATAGCGG TACTGATCGC GGTAGTTTAC TCCTCGTGTT     12000
GCAAGCACCC GGGCCGCTTT CGTTTCGCCG ACGAAGAGGC CGTCAACCTG TTGGACGACA     12060
CGGACGACAG TGGCGGCAGC AGCCCGTTTG GCAGCGGTTC CCGACGAGGT TCTCAGATCC     12120
```

```
CCGCCGGATT TTGTTCCTCG AGCCCTTATC AGCGGTTGGA AACTCGGGAC TGGGACGAGG    12180

AGGAGGAGGC GTCCGCGGCC CGCGAGCGCA TGAAACATGA TCCTGAGAAC GTCATCTATT    12240

TCAGAAAGGA TGGCAACTTG GACACGTCGT TCGTGAATCC CAATTATGGG AGAGGCTCGC    12300

CTTTGACCAT CGAATCTCAC CTCTCGGACA ATGAGGAGGA CCCCATCAGG TACTACGTTT    12360

CGGTGTACGA TGAACTGACC GCCTCGGAAA TGGAAGAACC TTCGAACAGC ACCAGCTGGC    12420

AGATTCCCAA ACTAATGAAA GTTGCCATGC AACCCGTCTC GCTCAGAGAT CCCGAGTACG    12480

ACTAGGCTTT TTTTTTTGTC TTTCGGTTCC AACTCTTTCC CCGCCCCATC ACCTCGCCTG    12540

TACTATGTGT ATGATGTCTC ATAATAAAGC TTTCTTTCTC AGTCTGCAAC ATGCAGCTGT    12600

GTCGGGTGTG GCTGTCTGTT TGTCTGTGCG CCGTGGTGCT GGGTCAGTGC CAGCGGGAAA    12660

CCGCGGAAAA AAACGATTAT TACCGAGTAC CGCATTACTG GGACGCGTGC TCTCGCGCGC    12720

TGCCCGACCA AACCCGTTAC AAGTATGTGG AACAGCTCGT GGACCTCACG TTGAACTACC    12780

ACTACGATGC GAGCCACGGC TTGGACAACT TTGACGTGCT CAAGAGGTGA GGGTACGCGC    12840

TAAAGGTGCA TGACAACGGG AAGGTAAGGG CGAACGGGTA ACGGCTAAGT AACCGCATGG    12900

GGTATGAAAT GACGTTTGGA ACCTGTGCTT GCAGAATCAA CGTGACCGAG GTGTCGTTGC    12960

TCATCAGCGA CTTTAGACGT CAGAACCGTC GCGGCGGCAC CAACAAAAGG ACCACGTTCA    13020

ACGCCGCCGG TTCGCTGGCG CCACACGCCC GGAGCCTCGA GTTCAGCGTG CGGCTCTTTG    13080

CCAACTAGCC TGCGTCACGG GAAATAATAT GCTGCGGCTT CTGCTTCGTC ACCACTTTCA    13140

CTGCCTGCTT CTGTGCGCGG TTTGGGCAAC GCCCTGTCTG GCGTCTCCGT GGTCGACGCT    13200

AACGGCAAAC CAGAATCCGT CCCCGCCATG GTCTAAACTG ACGTATTCCA AACCGCATGA    13260

CGCGGCGACG TTTTACTGTC CTTTTCTCTA TCCCTCGCCC CCACGGTCCC CCTTGCAATT    13320

CTCGGGGTTC CAGCAGGTAT CAACGGGTCC CGAGTGTCGC AACGAGACCC TGTATCTGCT    13380

GTACAACCGG GAAGGCCAGA CCTTGGTGGA GAGAAGCTCC ACCTGGGTGA AAAAGGTGAT    13440

CTGGTATCTG AGCGGTCGCA ACCAGACCAT CCTCCAACGG ATGCCCCAAA CGGCTTCGAA    13500

ACCGAGCGAC GGAAACGTGC AGATCAGCGT GGAAGACGCC AAGATTTTTG GAGCGCACAT    13560

GGTGCCCAAG CAGACCAAGC TGCTACGCTT CGTCGTCAAC GATGGCACGC GTTATCAGAT    13620

GTGTGTGATG AAGCTGGAGA GCTGGGCCCA CGTCTTCCGG GACTACAGCG TGTCTTTTCA    13680

GGTGCGATTG ACGTTCACCG AGGCCAATAA CCAGACTTAC ACCTTCTGTA CCCATCCCAA    13740

TCTCATCATT TGAGCCCGTC GCGCGCGCAG GGAATTTTGA AAACCGCGCG TCATGAGTCC    13800

CAAAGACCTG ACGCCGTTCT TGACGACGTT GTGGCTGCTA TTGGGTCACA GCCGCGTGCC    13860

GCGGGTGCGC GCAGAAGAAT GTTGCGAATT CATAAACGTC AACCACCCGC CGGAACGCTG    13920

TTACGATTTC AAAATGTGCA ATCGCTTCAC CGTCGCGTAC GTATTTTCAT GATTGTCTGC    13980

GTTCTGTGGT GCGTCTGGAT TTGTCTCTCG ACGTTTCTGA TAGCCATGTT CCATCGACGA    14040

TCCTCGGGAA TGCCAGAGTA GATTTTCATG AATCCACAGG CTGCGGTGTC CGGACGGCGA    14100

AGTCTGCTAC AGTCCCGAGA AAACGGCTGA GATTCGCGGG ATCGTCACCA CCATGACCCA    14160

TTCATTGACA CGCCAGGTCG TACACAACAA ACTGACGAGC TGCAACTACA ATCCGTAAGT    14220

CTCTTCCTCG AGGGCCTTAC AGCCTATGGG AGAGTAAGAC AGAGAGGGAC AAAACATCAT    14280

TAAAAAAAAA AGTCTAATTT CACGTTTTGT ACCCCCCTTC CCCTCCGTGT TGTAGCCCAT    14340

CGGCCGCGGC GATCTCCTAG TAACACTCGT CCGACACTTC CACCATCTCC AGCTCGGCCG    14400

GCGGTTCGGC ATCCTCTACC AGCGGCGTCG TCTCATCTTT GCCGCAGCAG CGGACGCACA    14460
```

-continued

```
CCTTCTCCAG GCAGAACGCC ACCAGCTGCC GCCGAACGTA CCACAGGTAC ACGTGCAGAC    14520
CTGCGAACAG GACTACGGAG GTCATGACCA CCACGACGCA CACGGGAATC CAGGGATCGA    14580
GATTGTTGCT GGAACTCATG GCTATCGCCA CCGACGTGCC CGCGTCTGTC TCACCGCCGC    14640
TCGCCCGATG TCGCGCGGCT TGTTATACGC TAGCCCGTCG CCGCCTCGGG GCACGGTGCC    14700
CTCCTACCCA CGTAACTTCC TCCGTGACTT AAAGTCGCGT GTGGTAGATC TCCTGCTCCG    14760
TGGACGAACC GTCCGGCAGG ATAGCGGTTA AGGATTCGGT GCTAAGGCCG TGTCGCCAAC    14820
GTCGAATGCT ACGTTGCAAC AGCTTCGACG GACGGCCATC CCCTCTCTCA TCGCAATAAT    14880
AAAACACCAG CAGCGCGCAC GACGCGATCA CGGTGACACC CATGATTAGA CCCACGCAGA    14940
TAGCCAGCCC CGCTAGCGTA TCTAGCGCCA TCCCGTTCGC TCCCGTTGTC TCCTGAGCGA    15000
AGCAACTTCT CGGTCCCCGT TTTCAACAGT TTTTGTTTCC TTCTCCGCGA CTAGATGTTA    15060
ACGCCCGCGG TCTTTCCGGC CGTGCTCTAC CTCCTGGCGC TTGTCGTCTG GGTTGAGATG    15120
TTCTGCCTCG TCGCCGTAGC CGTCGTCGAG CGCGAGATCG CCTGGGCGCT GCTGCTGCGG    15180
ATGCTGGTCG TTGGCCTGAT GGTGGAAGTC GGCGCCGCCG CCGCTTGGAC CTTCGTGCGT    15240
TGTCTTGCCT ATCAGCGCTC CTTCCCCGTG CTTACGGCCT TCCCCTGAAA CCCACGTTAA    15300
CCGACCGTCC CAAAAACGCC GGTGTTAACA CAGGAAAAAA AGAAACCACG CAGGAACCGC    15360
GCAGGAACCA CGCGGAACAT GGGACACTAT CTGGAAATCC TGTTCAACGT CATCGTCTTC    15420
ACTCTGCTGC TCGGCGTCAT GGTCAGTATC GTCGCTTGGT ACTTCACGTG AACCACCGTC    15480
GTCCCGGTTT AAAAACCATC ATCGACGGCC GTTATAAAGC CACCCGGACA CGCGCCGCGG    15540
CACTTGCCTA CGGCGCTGCT TCAGGGAAAC TCCTCTTCCT TCTGCTCTTC CTCCTTCACC    15600
GCAGGGATCG TTTCCCTCGA CCAGGGACTC GCCGAAGCAA CCGCCGGAGC AACCTGGAGG    15660
AGTCGCGGCA TGACGGCGCC CAAGTGTGTC ACCACCAGTA CTTATCTGGT CAAGACCAAG    15720
GAACAGCCCT GGTGGCCCGA CAACGCCATC AGGAGATGGT GGATCAGTGT TGCTATCGTC    15780
ATCTTCATCG GAGTCTGTCT GGTGGCCCTG ATGTACTTTA CGCAGCAGCA GGCACGCAGC    15840
GGGAGCAGCA GCGGCTAGAC AAGTCTCTGG CGGCTACAGC TCCAAGCGCC GTAGCCGGGC    15900
CGCCTGCCGA TCGCGACGTC GTGGACCATC GAACAGAGAC TCACGCGTAC GAGACCCCGA    15960
GGTACGCCAC GCGGTGCCTA ACGCGGTATA CCACACCCGT ACGGTCTGCA GTGCGGCGTA    16020
CAACGTGTGG AAAACGCGTT GCGTCGCAGA GTCCGCCACG TTCCTGTCTT GTCGCTCCCC    16080
AATCGTCTCC CGCACACCCC CCGCGACACC CAGAGGGCGG GTGAGCCAAG TATTCTTAAG    16140
GCCGTTCTTT GTTCCATAGC CCATAAATTG TTGATTCCGG AGCTCGTTGG CGCGGAAATA    16200
GCCGGATAAG GGGAGCAACA ACCGTTGGCG AAAGCCGTCC CGCTCATTCA GTCCGGGTTT    16260
CGCGTCCAGT CGGACGTGTG ACCGTTGGGC AACGGAACGG CGTTTCACTG CCAAAATCGT    16320
ATCGGGTAGT GTACGAGACG TCGGCGGTGC AGAATGCGAC TCGCGGCGTA GCTCGCCGTC    16380
GCTATGCGGC TCGTCGCCGT GTGGCGCGGC CTGGCCGGCT GTCTGCGTCC AGATCTGTTG    16440
GCCTTTTGGT TCCTCTGGCT GCTGCTGCGT GTGTGCTTTG GTAGACGCGG TGGCAGTTTG    16500
CGGTCTGCGG TAAGTGAGGA TGTCGCCGAG CAAACGCACT TGCGGCGCGT GGGCGGCACG    16560
CGTGTCATTG TAGGTTCGTT GCCAGATGGC AAGTGCTGTC AACAGCAGGC GTTGTGGGCG    16620
GTCGGTGTAT TTTTGTGGGT TGCGGTGAGA GTCGGCACTC GGTGTTTTGT GAGTCATCTC    16680
AACTATCTGT GTTGCTTTGA GCAGCGTCCA GAACAGCGAC GCGACTTTGG GGATGGCCTC    16740
GTGCTCACCT CCGCGGAGAG CGCCGCCGGA CCTGCTCGTC AGCAGCGAGC TACGCAGACG    16800
GAATATCTGG AGGAGAGTTA CGTGTGTCAC AGGAGAGCGC GGGTCTCCGG CGGTAACGAC    16860
```

```
GGCGGTGTCG TCGACACGTG TGCGGCCTGT TGTGCTCTGC GGAAAAGTGC CGGTCTCGGA    16920

GACCGTGGAC GAAAAAGAGA ACGCAGCAGC TACCGCTGGC GGCGGCGGCG TTAATGCAGC    16980

CGTTGATGTT CGACGTTGTG AGCACTCGGA AACAGCGGTG AGGCAGAAGG TCGATTCTCC    17040

AGGGAACGAC AGTCGATGCG TGGTAGCCGC AGCAGGTGAG GTTGGGGCGG ACAACGTGTT    17100

GCGGATTGTG GCGAGAACGT CGTCCTCCCC TTCTTCACCG CCCCACCCAC CCTCGGTTGG    17160

TGTTTCTTTT TTCTTGTGTC CTGCAGATAG TTCCACGGAC AGCGACGGCA AGTCCATAAT    17220

CAGCGGTGTG CAAGTGGTGG AACACGACGA AGATATCATC GCGCCGCAGA GTTTGTGGTG    17280

CACGGCGTTC AAGGAAGCCC TCTGGGATGT GGCTCTGTTG GAAGTGCCGC GTTGGGCGTG    17340

GCAGGGCTGG AAGAGGTGGC GCAACAGCGA GGCCGGGCGT CGATGGAGTG CTGGGTCTGC    17400

GTCGGCTTCC AGCTTGTCTG ACTTGGCGGG CGAGGCCGTT GGAGAATTGG TGGGATCGGT    17460

CGTCGCGTAC GTGATCCTTG AACGTCTGTG GTTGGCAGCC AGAGGTTGGG TGTGCGAAAC    17520

AGGTGTGGAA GCCGAGGAGG CCATGTCGCG GCGGCGACAG CGCATGCTGT GGCGTATTGT    17580

TCTCTCGTGG AGGCGACGGC GAATGCAGCA GACGGTGTTC GATGGAGATG GCGTGCGGGG    17640

AAGAAAGCGC CGTGTTGTGA GCAGACGACG TAGGATGCGG GACGTCGGAG CACATGGGCC    17700

ATGTGTGGTG GCAGATGGCG GTGTCCGCTG GTGTCTGCTG CGGCAGTGCA TAGACGAAGC    17760

AACATGTCGC TGTGAAGAGA TAGAGTGTGA GCATAGCTGC ATGCAGCGTT GCGTGTATAA    17820

GCGGGGGGGA TTAAGACGTT AATAAAGAAT AGCGGCGGTT CTGATAGGGC GACCGCTGAA    17880

GTGAGCTGCG TGTGCGTGTG GTTTGTGGAG TCCCCGCCGC CCCCGGTCCC GTGTCCGCCG    17940

GCAAAGCCCC CCGGNTCCGC ACACTCCTGG CCGCGCAACC CTCGTCGCTG CAAAAGCCCC    18000

CCGTCCCCGC ACACCCCGC GACCGCCGGT CCCGCGAGTC CCCGTCCCCG CCGCAAAAGG     18060

CCCCCGTCCT CGCCGCAAAC ACCCCCGTCA CCCCCGTCCC TCAGNCCGGG TCCGCGAGTC    18120

CCCGTTCCCA GCGTAATCCC CGTACCCGCA ACGNCCCGGN CCCACCGTCG TCCCGCACAC    18180

CCCCCGTCCC CCAGCCCGGT GCCCAGCGTG CGAAAAAAGC TCCGTCCCTC ACACCCGCAG    18240

AAAGATCCCT CAGCGCGGTG AAACCCCGTC CCCAGCGCCG TGCCGCTGAC AAAGACCATG    18300

GGACGACACG CACAGGCA                                                 18318
```

(2) INFORMATION FOR SEQ ID NO:7:

(i) SEQUENCE CHARACTERISTICS:
        (A) LENGTH: 257 amino acids
        (B) TYPE: amino acid
        (D) TOPOLOGY: linear (ii) MOLECULE TYPE: protein (vii) IMMEDIATE SOURCE:
        (B) CLONE: tol.01

(ix) FEATURE:
        (A) NAME/KEY: Protein
        (B) LOCATION: 1..257
        (D) OTHER INFORMATION: /label= UL133

(xi) SEQUENCE DESCRIPTION: SEQ ID NO:7:

```
Met Gly Cys Asp Val His Asp Pro Ser Trp Gln Cys Gln Trp Gly Val
1               5                   10                  15

Pro Thr Ile Ile Val Ala Trp Ile Thr Cys Ala Ala Leu Gly Ile Trp
            20                  25                  30

Cys Leu Ala Gly Ser Ser Ala Asp Val Ser Ser Gly Pro Gly Ile Ala
        35                  40                  45
```

```
Ala Val Val Gly Cys Ser Val Phe Met Ile Phe Leu Cys Ala Tyr Leu
     50                  55                  60

Ile Arg Tyr Arg Glu Phe Phe Lys Asp Ser Val Ile Asp Leu Leu Thr
 65                  70                  75                  80

Cys Arg Trp Val Arg Tyr Cys Ser Cys Ser Cys Lys Cys Ser Cys Lys
                 85                  90                  95

Cys Ile Ser Gly Pro Cys Ser Arg Cys Cys Ser Ala Cys Tyr Lys Glu
                100                 105                 110

Thr Met Ile Tyr Asp Met Val Gln Tyr Gly His Arg Arg Arg Pro Gly
            115                 120                 125

His Gly Asp Asp Pro Asp Arg Val Ile Cys Glu Ile Val Glu Ser Pro
    130                 135                 140

Pro Val Ser Ala Pro Thr Val Ser Val Pro Pro Ser Glu Glu Ser
145                 150                 155                 160

His Gln Pro Val Ile Pro Pro Gln Pro Ala Pro Thr Ser Glu Pro
                165                 170                 175

Lys Pro Lys Lys Gly Arg Ala Lys Asp Lys Pro Lys Gly Arg Pro Lys
                180                 185                 190

Asp Lys Pro Pro Cys Glu Pro Thr Val Ser Ser Gln Pro Pro Ser Gln
            195                 200                 205

Pro Thr Ala Met Pro Gly Gly Pro Pro Asp Ala Pro Pro Pro Ala Met
210                 215                 220

Pro Gln Met Pro Pro Gly Val Ala Glu Ala Val Gln Ala Ala Val Gln
225                 230                 235                 240

Ala Ala Val Ala Ala Ala Leu Gln Gln Gln Gln His Gln Thr Gly
                245                 250                 255

Thr (2) INFORMATION FOR SEQ ID NO:8:

(i) SEQUENCE CHARACTERISTICS:
        (A) LENGTH: 175 amino acids
        (B) TYPE: amino acid
        (D) TOPOLOGY: linear (ii) MOLECULE TYPE: protein (vii) IMMEDIATE SOURCE:
        (B) CLONE: tol.02

(ix) FEATURE:
        (A) NAME/KEY: Protein
        (B) LOCATION: 1..175
        (D) OTHER INFORMATION: /label= UL134

(xi) SEQUENCE DESCRIPTION: SEQ ID NO:8:

Met Ala Arg Thr Arg Glu Ala Ser Pro Val Pro Pro Arg Ser Pro Met
  1               5                  10                  15

Pro Ser His Ile His Thr Met Ile Phe Ser Pro Ala Trp Asn Leu Lys
                 20                  25                  30

Leu Arg Val Gly Lys Gly Arg Cys Thr Asp Ile Tyr Ala Leu Asp Phe
             35                  40                  45

Trp Lys Arg His Phe Leu Ala Arg Asn Val Phe Ile Val Gln Thr Leu
 50                  55                  60

Arg Lys Glu Met Cys Ala Lys Ser Glu Asn Ser Leu Ser His Arg Gly
 65                  70                  75                  80

Arg Val Thr Phe Arg Ser Asp Ala Ala Val Val Glu Pro Arg
                 85                  90                  95
```

```
Pro Arg Pro Pro Ala Arg Gln Leu Val Pro Pro Arg Pro Arg Arg Val
            100                 105                 110

Ala Ser Ala Ala Trp Arg Gly Glu Ala Arg Arg Ala Asp Arg Arg Ala
            115                 120                 125

Leu Pro Ser Ala Ala Thr Val Val Asn Ser Pro Ser Val Arg Thr
            130                 135                 140

Glu Val Cys Leu Ser Val Tyr Pro Ser Val Tyr Leu Ser Pro Tyr Leu
145                 150                 155                 160

Ser Ser Val Trp Val Pro Met Ser Val Leu Ala Ala Val Gly
                165                 170                 175
```

(2) INFORMATION FOR SEQ ID NO:9:

(i) SEQUENCE CHARACTERISTICS:
        (A) LENGTH: 328 amino acids
        (B) TYPE: amino acid
        (D) TOPOLOGY: linear (ii) MOLECULE TYPE: protein (vii) IMMEDIATE SOURCE:
        (B) CLONE: tol.03

(ix) FEATURE:
        (A) NAME/KEY: Protein
        (B) LOCATION: 1..328
        (D) OTHER INFORMATION: /label= UL135

(xi) SEQUENCE DESCRIPTION: SEQ ID NO:9:

```
Met Ser Val His Arg Pro Phe Pro Thr Arg Ser Leu Arg Phe Gln Ala
1               5                   10                  15

Gly Glu Lys Ile Met Val Trp Ile Trp Leu Gly Ile Gly Leu Leu Gly
            20                  25                  30

Gly Thr Gly Leu Ala Ser Leu Val Leu Ala Ile Ser Leu Phe Thr Gln
            35                  40                  45

Arg Arg Gly Arg Lys Arg Ser Asp Glu Thr Ser Ser Arg Gly Arg Leu
        50                  55                  60

Pro Gly Ala Ala Ser Asp Lys Arg Gly Ala Cys Ala Cys Cys Tyr Arg
65                  70                  75                  80

Asn Pro Lys Glu Asp Val Val Glu Pro Leu Asp Leu Glu Leu Gly Leu
            85                  90                  95

Met Arg Val Asp Thr His Pro Pro Thr Pro Gln Val Pro Arg Cys Thr
            100                 105                 110

Ser Leu Tyr Ile Gly Glu Asp Gly Leu Pro Ile Asp Lys Pro Glu Phe
            115                 120                 125

Pro Pro Ala Arg Phe Glu Ile Pro Asp Val Ser Thr Pro Gly Thr Pro
            130                 135                 140

Thr Ser Ile Gly Arg Ser Pro Ser His Cys Ser Ser Ser Ser Ser Leu
145                 150                 155                 160

Ser Ser Ser Thr Ser Val Asp Thr Val Leu Tyr Gln Pro Pro Pro Ser
            165                 170                 175

Trp Lys Pro Pro Pro Pro Gly Arg Lys Lys Arg Pro Pro Thr Pro
            180                 185                 190

Pro Val Arg Ala Pro Thr Thr Arg Leu Ser Ser His Arg Pro Pro Thr
            195                 200                 205

Pro Ile Pro Ala Pro Arg Lys Asn Leu Ser Thr Pro Thr Lys Lys
            210                 215                 220

Thr Pro Pro Pro Thr Lys Pro Lys Pro Val Gly Trp Thr Pro Pro Val
```

```
            225                 230                 235                 240
Thr Pro Arg Pro Phe Pro Lys Thr Pro Thr Pro Gln Lys Pro Pro Arg
                245                 250                 255

Asn Pro Arg Leu Pro Arg Thr Val Gly Leu Glu Asn Leu Ser Lys Val
                260                 265                 270

Gly Leu Ser Cys Pro Cys Pro Arg Pro Arg Thr Pro Thr Glu Pro Thr
                275                 280                 285

Thr Leu Pro Ile Val Ser Val Ser Glu Leu Ala Pro Pro Pro Arg Trp
                290                 295                 300

Ser Asp Ile Glu Glu Leu Leu Glu Gln Ala Val Gln Ser Val Met Lys
305                 310                 315                 320

Asp Ala Glu Ser Met Gln Met Thr
                325
```

(2) INFORMATION FOR SEQ ID NO:10:

(i) SEQUENCE CHARACTERISTICS:
        (A) LENGTH: 240 amino acids
        (B) TYPE: amino acid
        (D) TOPOLOGY: linear (ii) MOLECULE TYPE: protein (vii) IMMEDIATE SOURCE:
        (B) CLONE: tol.04

(ix) FEATURE:
        (A) NAME/KEY: Protein
        (B) LOCATION: 1..240
        (D) OTHER INFORMATION: /label= UL136

(xi) SEQUENCE DESCRIPTION: SEQ ID NO:10:

```
Met Ser Val Lys Gly Val Glu Met Pro Glu Met Thr Trp Asp Leu Asp
1               5                   10                  15

Val Arg Asn Lys Trp Arg Arg Lys Ala Leu Ser Arg Ile His Arg
                20                  25                  30

Phe Trp Glu Cys Arg Leu Arg Val Trp Trp Leu Ser Asp Ala Gly Val
                35                  40                  45

Arg Glu Thr Asp Pro Pro Arg Pro Arg Arg Pro Thr Trp Met Thr
50                  55                  60

Ala Val Phe His Val Ile Cys Ala Val Leu Leu Thr Leu Met Ile Met
65                  70                  75                  80

Ala Ile Gly Ala Leu Ile Ala Tyr Leu Arg Tyr Tyr His Gln Asp Ser
                85                  90                  95

Trp Arg Asp Met Leu His Asp Leu Phe Cys Gly Cys His Tyr Pro Glu
                100                 105                 110

Lys Cys Arg Arg His His Glu Arg Gln Arg Arg Arg Gln Ala Met
                115                 120                 125

Asp Val Pro Asp Pro Glu Leu Gly Asp Pro Ala Arg Arg Pro Leu Asn
130                 135                 140

Gly Ala Met Tyr Tyr Gly Ser Gly Cys Arg Phe Asp Thr Val Glu Met
145                 150                 155                 160

Val Asp Glu Thr Arg Pro Ala Pro Pro Ala Leu Ser Ser Pro Glu Thr
                165                 170                 175

Gly Asp Asp Ser Asn Asp Asp Ala Val Ala Gly Gly Ala Gly Gly
                180                 185                 190

Val Thr Ser Pro Ala Thr Arg Thr Thr Ser Pro Asn Ala Leu Leu Pro
                195                 200                 205
```

```
Glu Trp Met Asp Ala Val His Val Ala Val Gln Ala Val Gln Ala
    210                 215                 220

Thr Val Gln Val Ser Gly Pro Arg Glu Asn Ala Val Ser Pro Ala Thr
225                 230                 235                 240
```

(2) INFORMATION FOR SEQ ID NO:11:

(i) SEQUENCE CHARACTERISTICS:
  (A) LENGTH: 96 amino acids
  (B) TYPE: amino acid
  (D) TOPOLOGY: linear (ii) MOLECULE TYPE: protein (vii) IMMEDIATE SOURCE:
  (B) CLONE: tol.05

(ix) FEATURE:
  (A) NAME/KEY: Protein
  (B) LOCATION: 1..96
  (D) OTHER INFORMATION: /label= UL137

(xi) SEQUENCE DESCRIPTION: SEQ ID NO:11:

```
Met Ala Thr Ile Ser Thr Ser Ile Thr Pro Met Met Gly Asn Pro Thr
1               5                   10                  15

Phe Ser Gly Arg Ser Ser Met Val Thr Val Leu Cys Pro Asp Leu Arg
                20                  25                  30

Pro Ser Leu Ser Leu Leu Tyr Ser Thr Arg Ala Gly Thr Ala Pro Ser
            35                  40                  45

Thr Leu Leu Arg Ser Gly Arg Tyr Gly Val Leu Pro Arg Ala Thr Tyr
        50                  55                  60

Leu His Gly Arg Leu Asn Gly Gly Leu Asp Arg His Met His Arg Ile
65                  70                  75                  80

His Pro Phe Trp Gln Gln Cys Val Arg Arg Arg Thr Ser Arg Gly
                85                  90                  95
```

(2) INFORMATION FOR SEQ ID NO:12:

(i) SEQUENCE CHARACTERISTICS:
  (A) LENGTH: 169 amino acids
  (B) TYPE: amino acid
  (D) TOPOLOGY: linear (ii) MOLECULE TYPE: protein (vii) IMMEDIATE SOURCE:
  (B) CLONE: tol.06

(ix) FEATURE:
  (A) NAME/KEY: Protein
  (B) LOCATION: 1..169
  (D) OTHER INFORMATION: /label= UL138

(xi) SEQUENCE DESCRIPTION: SEQ ID NO:12:

```
Met Asp Asp Leu Pro Leu Asn Val Gly Leu Pro Ile Ile Gly Val Met
1               5                   10                  15

Leu Val Leu Ile Val Ala Ile Leu Cys Tyr Leu Ala Tyr His Trp His
                20                  25                  30

Asp Thr Phe Lys Leu Val Arg Met Phe Leu Ser Tyr Arg Trp Leu Ile
            35                  40                  45

Arg Cys Cys Glu Leu Tyr Gly Glu Tyr Glu Arg Arg Phe Ala Asp Leu
        50                  55                  60

Ser Ser Leu Gly Leu Gly Ala Val Arg Arg Glu Ser Asp Arg Arg Tyr
65                  70                  75                  80
```

-continued

```
Arg Phe Ser Glu Arg Pro Asp Glu Ile Leu Val Arg Trp Glu Glu Val
                85                  90                  95

Ser Ser Gln Cys Ser Tyr Ala Ser Ser Arg Ile Thr Asp Arg Arg Val
            100                 105                 110

Gly Ser Ser Ser Ser Ser Val His Val Ala Ser Gln Arg Asn Ser
        115                 120                 125

Val Pro Pro Asp Met Ala Val Thr Ala Pro Leu Thr Asp Val Asp
    130                 135                 140

Leu Leu Lys Pro Val Thr Gly Ser Ala Thr Gln Phe Thr Thr Val Ala
145                 150                 155                 160

Met Val His Tyr His Gln Glu Tyr Thr
                165
```

(2) INFORMATION FOR SEQ ID NO:13:

(i) SEQUENCE CHARACTERISTICS:
        (A) LENGTH: 135 amino acids
        (B) TYPE: amino acid
        (D) TOPOLOGY: linear (ii) MOLECULE TYPE: protein (vii) IMMEDIATE SOURCE:
        (B) CLONE: tol.07

(ix) FEATURE:
        (A) NAME/KEY: Protein
        (B) LOCATION: 1..135
        (D) OTHER INFORMATION: /label= UL139

(xi) SEQUENCE DESCRIPTION: SEQ ID NO:13:

```
Met Leu Trp Ile Leu Val Leu Phe Ala Leu Ala Ala Ser Ala Ser Glu
1               5                   10                  15

Thr Thr Thr Gly Thr Ser Ser Asn Ser Ser Gln Ser Thr Ser Ala Thr
            20                  25                  30

Ala Asn Thr Thr Val Ser Thr Cys Ile Asn Ala Ser Asn Gly Ser Ser
        35                  40                  45

Trp Thr Val Pro Gln Leu Ala Leu Leu Ala Ala Ser Gly Trp Thr Leu
    50                  55                  60

Ser Gly Leu Leu Leu Leu Phe Thr Cys Cys Phe Cys Cys Phe Trp Leu
65                  70                  75                  80

Val Arg Lys Ile Cys Ser Cys Cys Gly Asn Ser Ser Glu Ser Glu Ser
                85                  90                  95

Lys Thr Thr His Ala Tyr Thr Asn Ala Ala Phe Thr Ser Ser Asp Ala
            100                 105                 110

Thr Leu Pro Met Gly Thr Thr Gly Ser Tyr Thr Pro Pro Gln Asp Gly
        115                 120                 125

Ser Phe Pro Pro Pro Pro Arg
    130                 135
```

(2) INFORMATION FOR SEQ ID NO:14:

(i) SEQUENCE CHARACTERISTICS:
        (A) LENGTH: 114 amino acids
        (B) TYPE: amino acid
        (D) TOPOLOGY: linear (ii) MOLECULE TYPE: protein (vii) IMMEDIATE SOURCE:
        (B) CLONE: tol.08

(ix) FEATURE:

(A) NAME/KEY: Protein
            (B) LOCATION: 1..114
            (D) OTHER INFORMATION: /label= UL140

(xi) SEQUENCE DESCRIPTION: SEQ ID NO:14:

Met Thr Pro Ala Gln Thr Asn Ala Thr Thr Val His Pro His Asp
1               5                   10                  15

Ala Lys Asn Gly Ser Gly Gly Ser Ala Leu Pro Thr Leu Val Val Phe
            20                  25                  30

Gly Phe Ile Val Thr Leu Leu Phe Phe Leu Phe Met Leu Tyr Phe Trp
            35                  40                  45

Asn Asn Asp Val Phe Arg Lys Leu Leu Arg Ala Leu Gly Ser Ser Ala
50                      55                  60

Val Ala Thr Ala Ser Thr Arg Gly Lys Thr Arg Ser Ser Thr Val Val
65                  70                  75                  80

His His Val Val Pro Arg Ala Thr Thr Arg Val Val Leu Thr Ala Cys
                    85                  90                  95

His Arg Thr Phe Phe Tyr His Pro Arg Pro Met Ala Val Leu Thr Thr
                100                 105                 110

Arg His (2) INFORMATION FOR SEQ ID NO:15:

(i) SEQUENCE CHARACTERISTICS:
        (A) LENGTH: 425 amino acids
        (B) TYPE: amino acid
        (D) TOPOLOGY: linear (ii) MOLECULE TYPE: protein (vii) IMMEDIATE SOURCE:
        (B) CLONE: tol.09

(ix) FEATURE:
        (A) NAME/KEY: Protein
        (B) LOCATION: 1..425
        (D) OTHER INFORMATION: /label= UL141

(xi) SEQUENCE DESCRIPTION: SEQ ID NO:15:

Met Arg Gln Val Ala Tyr Arg Arg Arg Glu Ser Ser Cys Ala Val
1               5                   10                  15

Leu Val His His Val Gly Arg Asp Gly Asp Gly Glu Gly Glu Ala Ala
            20                  25                  30

Lys Lys Thr Cys Lys Lys Thr Gly Arg Ser Val Ala Gly Ile Pro Gly
            35                  40                  45

Glu Lys Leu Arg Arg Thr Val Val Thr Thr Thr Pro Ala Arg Arg Leu
50                      55                  60

Ser Gly Arg His Thr Glu Gln Glu Gln Ala Gly Met Arg Leu Cys Glu
65                  70                  75                  80

Lys Gly Lys Lys Arg Ile Ile Met Cys Arg Arg Glu Ser Leu Arg Thr
                    85                  90                  95

Leu Pro Trp Leu Phe Trp Val Leu Leu Ser Cys Pro Arg Leu Leu Glu
                100                 105                 110

Tyr Ser Ser Ser Phe Pro Phe Ala Thr Ala Asp Ile Ala Glu Lys
                115                 120                 125

Met Trp Ala Glu Asn Tyr Glu Thr Thr Ser Pro Ala Pro Val Leu Val
130                 135                 140

Ala Glu Gly Glu Gln Val Thr Ile Pro Cys Thr Val Met Thr His Ser
145                 150                 155                 160

-continued

```
Trp Pro Met Val Ser Ile Arg Ala Arg Phe Cys Arg Ser His Asp Gly
            165                 170                 175

Ser Asp Glu Leu Ile Leu Asp Ala Val Lys Gly His Arg Leu Met Asn
            180                 185                 190

Gly Leu Gln Tyr Arg Leu Pro Tyr Ala Thr Trp Asn Phe Ser Gln Leu
            195                 200                 205

His Leu Gly Gln Ile Phe Ser Leu Thr Phe Asn Val Ser Met Asp Thr
            210                 215                 220

Ala Gly Met Tyr Glu Cys Val Leu Arg Asn Tyr Ser His Gly Leu Ile
225                 230                 235                 240

Met Gln Arg Phe Val Ile Leu Thr Gln Leu Glu Thr Leu Ser Arg Pro
            245                 250                 255

Asp Glu Pro Cys Cys Thr Pro Ala Leu Gly Arg Tyr Ser Leu Gly Asp
            260                 265                 270

Gln Ile Trp Ser Pro Thr Pro Trp Arg Leu Arg Asn His Asp Cys Gly
            275                 280                 285

Thr Tyr Arg Gly Phe Gln Arg Asn Tyr Phe Tyr Ile Gly Arg Ala Asp
            290                 295                 300

Ala Glu Asp Cys Trp Lys Pro Ala Cys Pro Asp Glu Pro Asp Arg
305                 310                 315                 320

Cys Trp Thr Val Ile Gln Arg Tyr Arg Leu Pro Gly Asp Cys Tyr Arg
            325                 330                 335

Ser Gln Pro His Pro Pro Lys Phe Leu Pro Val Thr Pro Ala Pro Pro
            340                 345                 350

Ala Asp Ile Asp Thr Gly Met Ser Pro Trp Ala Thr Arg Gly Ile Ala
            355                 360                 365

Ala Phe Leu Gly Phe Trp Ser Ile Phe Thr Val Cys Phe Leu Cys Tyr
            370                 375                 380

Leu Cys Tyr Leu Gln Cys Cys Gly Arg Trp Cys Pro Thr Pro Gly Arg
385                 390                 395                 400

Gly Arg Arg Gly Gly Glu Gly Tyr Arg Arg Leu Pro Thr Tyr Asp Ser
            405                 410                 415

Tyr Pro Gly Val Arg Lys Met Lys Arg
            420                 425

(2) INFORMATION FOR SEQ ID NO:16:

(i) SEQUENCE CHARACTERISTICS:
        (A) LENGTH: 306 amino acids
        (B) TYPE: amino acid
        (D) TOPOLOGY: linear (ii) MOLECULE TYPE: protein (vii) IMMEDIATE SOURCE:
        (B) CLONE: tol.10

(ix) FEATURE:
        (A) NAME/KEY: Protein
        (B) LOCATION: 1..306
        (D) OTHER INFORMATION: /label= UL142

(xi) SEQUENCE DESCRIPTION: SEQ ID NO:16:

Met Arg Ile Glu Trp Val Trp Trp Leu Phe Gly Tyr Phe Val Ser Ser
1               5                   10                  15

Val Gly Ser Glu Arg Ser Leu Ser Tyr Arg Tyr His Leu Glu Ser Asn
                20                  25                  30

Ser Ser Thr Asn Val Val Cys Asn Gly Asn Ile Ser Val Phe Val Asn
            35                  40                  45
```

```
Gly Thr Leu Gly Val Arg Tyr Asn Ile Thr Val Gly Ile Ser Ser Ser
        50                  55                  60

Leu Leu Ile Gly His Leu Thr Ile Gln Val Leu Glu Ser Trp Phe Thr
 65                  70                  75                  80

Pro Trp Val Gln Asn Lys Ser Tyr Asn Lys Gln Pro Leu Gly Asp Thr
                 85                  90                  95

Glu Thr Leu Tyr Asn Ile Asp Ser Glu Asn Ile His Arg Val Ser Gln
                100                 105                 110

Tyr Phe His Thr Arg Trp Ile Lys Ser Leu Gln Glu Asn His Thr Cys
            115                 120                 125

Asp Leu Thr Asn Ser Thr Pro Thr Tyr Thr Tyr Gln Val Asn Val Asn
130                 135                 140

Asn Thr Asn Tyr Leu Thr Leu Thr Ser Ser Gly Trp Gln Asp Arg Leu
145                 150                 155                 160

Asn Tyr Thr Val Ile Asn Ser Thr His Phe Asn Leu Thr Glu Ser Asn
                165                 170                 175

Ile Thr Ser Ile Gln Lys Tyr Leu Asn Thr Thr Cys Ile Glu Arg Leu
            180                 185                 190

Arg Asn Tyr Thr Leu Glu Ser Val Tyr Thr Thr Thr Val Pro Gln Asn
            195                 200                 205

Ile Thr Thr Ser Gln His Ala Thr Thr Thr Met His Thr Ile Pro Pro
210                 215                 220

Asn Thr Ile Thr Ile Gln Asn Thr Thr Gln Ser His Thr Val Gln Thr
225                 230                 235                 240

Pro Ser Phe Asn Asp Thr His Asn Val Thr Lys His Thr Leu Asn Ile
                245                 250                 255

Ser Tyr Val Leu Ser Gln Lys Thr Asn Asn Thr Thr Ser Pro Trp Ile
            260                 265                 270

Tyr Ala Ile Pro Met Gly Ala Thr Ala Thr Ile Gly Ala Gly Leu Tyr
            275                 280                 285

Ile Gly Lys His Phe Thr Pro Val Lys Phe Val Tyr Glu Val Trp Arg
        290                 295                 300

Gly Gln
305

(2) INFORMATION FOR SEQ ID NO:17:

(i) SEQUENCE CHARACTERISTICS:
        (A) LENGTH: 92 amino acids
        (B) TYPE: amino acid
        (D) TOPOLOGY: linear (ii) MOLECULE TYPE: protein (vii) IMMEDIATE SOURCE:
        (B) CLONE: tol.11

(ix) FEATURE:
        (A) NAME/KEY: Protein
        (B) LOCATION: 1..92
        (D) OTHER INFORMATION: /label= UL143

(xi) SEQUENCE DESCRIPTION: SEQ ID NO:17:

Met Ala Arg Ser Val Lys Thr Ile Arg Ile Gln His Ile Tyr Ser Pro
 1               5                  10                  15

Arg Ser Ser Asn Thr Leu Gln His Met Ser Lys Lys Gln Glu Ser Ile
                20                  25                  30

Ala Thr Ile Thr Phe Gly Arg Ile Thr Cys Cys His Pro Leu Ala Ser
```

```
                    35                  40                  45
Ile Asn Leu Met Phe Asn Gly Ser Cys Thr Val Thr Val Lys Ile Ser
 50                  55                  60

Met Gly Ile Asn Gly Ser Thr Asn Val His Gln Leu Val Ile Val Leu
 65                  70                  75                  80

His Leu Gly Asn Arg Cys Gln Pro Trp Arg Gln Val
                 85                  90
```

(2) INFORMATION FOR SEQ ID NO:18:

(i) SEQUENCE CHARACTERISTICS:
        (A) LENGTH: 176 amino acids
        (B) TYPE: amino acid
        (D) TOPOLOGY: linear (ii) MOLECULE TYPE: protein (vii) IMMEDIATE SOURCE:
        (B) CLONE: tol.12

(ix) FEATURE:
        (A) NAME/KEY: Protein
        (B) LOCATION: 1..176
        (D) OTHER INFORMATION: /label= UL144

(xi) SEQUENCE DESCRIPTION: SEQ ID NO:18:

```
Met Lys Pro Leu Ile Met Leu Ile Cys Phe Ala Val Ile Leu Leu Gln
  1                   5                  10                  15

Leu Gly Val Thr Lys Val Cys Gln His Asn Glu Val Gln Leu Gly Asn
                 20                  25                  30

Glu Cys Cys Pro Pro Cys Gly Ser Gly Gln Arg Val Thr Lys Val Cys
                 35                  40                  45

Thr Asp Tyr Thr Ser Val Thr Cys Thr Pro Cys Pro Asn Gly Thr Tyr
 50                  55                  60

Val Ser Gly Leu Tyr Asn Cys Thr Asp Cys Thr Gln Cys Asn Val Thr
 65                  70                  75                  80

Gln Val Met Ile Arg Asn Cys Thr Ser Thr Asn Asn Thr Val Cys Ala
                 85                  90                  95

Pro Lys Asn His Thr Tyr Phe Ser Thr Pro Gly Val Gln His His Lys
                100                 105                 110

Gln Arg Gln Gln Asn His Thr Ala His Ile Thr Val Lys Gln Gly Lys
                115                 120                 125

Ser Gly Arg His Thr Leu Ala Trp Leu Ser Leu Phe Ile Phe Leu Val
                130                 135                 140

Gly Ile Ile Leu Leu Ile Leu Tyr Leu Ile Ala Ala Tyr Arg Ser Glu
145                 150                 155                 160

Arg Cys Gln Gln Cys Cys Ser Ile Gly Lys Ile Phe Tyr Arg Thr Leu
                165                 170                 175
```

(2) INFORMATION FOR SEQ ID NO:19:

(i) SEQUENCE CHARACTERISTICS:
        (A) LENGTH: 100 amino acids
        (B) TYPE: amino acid
        (D) TOPOLOGY: linear (ii) MOLECULE TYPE: protein (vii) IMMEDIATE SOURCE:
        (B) CLONE: tol.13

(ix) FEATURE:
        (A) NAME/KEY: Protein

```
            (B) LOCATION: 1..100
            (D) OTHER INFORMATION: /label= UL145

(xi) SEQUENCE DESCRIPTION: SEQ ID NO:19:

Met Cys Thr Asp Pro Arg Arg Thr Ala Gly Trp Glu Arg Leu Thr His
1               5                  10                  15

His Ala Ser Tyr His Ala Asn Tyr Gly Ala Tyr Ala Val Leu Met Ala
            20                  25                  30

Thr Ser Gln Arg Lys Ser Leu Val Leu His Arg Tyr Ser Ala Val Thr
        35                  40                  45

Ala Val Ala Leu Gln Leu Met Pro Val Glu Ile Val Arg Lys Leu Asp
    50                  55                  60

Gln Ser Asp Trp Val Arg Gly Ala Trp Ile Val Ser Glu Thr Phe Pro
65              70                  75                  80

Thr Ser Asp Pro Lys Gly Val Trp Ser Asp Asp Ser Ser Met Gly
            85                  90                  95

Gly Ser Asp Asp
            100

(2) INFORMATION FOR SEQ ID NO:20:

(i) SEQUENCE CHARACTERISTICS:
        (A) LENGTH: 117 amino acids
        (B) TYPE: amino acid
        (D) TOPOLOGY: linear (ii) MOLECULE TYPE: protein (vii) IMMEDIATE SOURCE:
        (B) CLONE: tol.14

(ix) FEATURE:
        (A) NAME/KEY: Protein
        (B) LOCATION: 1..117
        (D) OTHER INFORMATION: /label= UL146

(xi) SEQUENCE DESCRIPTION: SEQ ID NO:20:

Met Arg Leu Ile Phe Gly Ala Leu Ile Ile Phe Leu Ala Tyr Val Tyr
1               5                  10                  15

His Tyr Glu Val Asn Gly Thr Glu Leu Arg Cys Arg Cys Leu His Arg
            20                  25                  30

Lys Trp Pro Pro Asn Lys Ile Ile Leu Gly Asn Tyr Trp Leu His Arg
        35                  40                  45

Asp Pro Arg Gly Pro Gly Cys Asp Lys Asn Glu His Leu Leu Tyr Pro
    50                  55                  60

Asp Gly Arg Lys Pro Pro Gly Pro Gly Val Cys Leu Ser Pro Asp His
65              70                  75                  80

Leu Phe Ser Lys Trp Leu Asp Lys His Asn Asp Asn Arg Trp Tyr Asn
            85                  90                  95

Val Asn Ile Thr Lys Ser Pro Gly Pro Arg Arg Ile Asn Ile Thr Leu
            100                 105                 110

Ile Gly Val Arg Gly
            115

(2) INFORMATION FOR SEQ ID NO:21:

(i) SEQUENCE CHARACTERISTICS:
        (A) LENGTH: 159 amino acids
        (B) TYPE: amino acid
        (D) TOPOLOGY: linear (ii) MOLECULE TYPE: protein
```

(vii) IMMEDIATE SOURCE:
        (B) CLONE: tol.15

(ix) FEATURE:
        (A) NAME/KEY: Protein
        (B) LOCATION: 1..159
        (D) OTHER INFORMATION: /label= UL147

(xi) SEQUENCE DESCRIPTION: SEQ ID NO:21:

```
Met Val Leu Thr Trp Leu His His Pro Val Ser Asn Ser His Ile Asn
1               5                   10                  15

Leu Leu Ser Val Arg His Leu Ser Leu Ile Ala Tyr Met Leu Leu Thr
                20                  25                  30

Ile Cys Pro Leu Ala Val His Val Leu Glu Leu Glu Asp Tyr Asp Arg
            35                  40                  45

Arg Cys Arg Cys Asn Asn Gln Ile Leu Leu Asn Thr Leu Pro Val Gly
        50                  55                  60

Thr Glu Leu Leu Lys Pro Ile Ala Ala Ser Glu Ser Cys Asn Arg Gln
65                  70                  75                  80

Glu Val Leu Ala Ile Leu Lys Asp Lys Gly Thr Lys Cys Leu Asn Pro
                85                  90                  95

Asn Ala Gln Ala Val Arg Arg His Ile Asn Arg Leu Phe Phe Arg Leu
            100                 105                 110

Ile Leu Asp Glu Glu Gln Arg Ile Tyr Asp Val Val Ser Thr Asn Ile
        115                 120                 125

Glu Phe Gly Ala Trp Pro Val Pro Thr Ala Tyr Lys Ala Phe Leu Trp
130                 135                 140

Lys Tyr Ala Lys Arg Leu Asn Tyr His His Phe Arg Leu Arg Trp
145                 150                 155
```

(2) INFORMATION FOR SEQ ID NO:22:

(i) SEQUENCE CHARACTERISTICS:
    (A) LENGTH: 316 amino acids
    (B) TYPE: amino acid
    (D) TOPOLOGY: linear (ii) MOLECULE TYPE: protein (vii) IMMEDIATE SOURCE:
        (B) CLONE: tol.16

(ix) FEATURE:
        (A) NAME/KEY: Protein
        (B) LOCATION: 1..316
        (D) OTHER INFORMATION: /label= UL148

(xi) SEQUENCE DESCRIPTION: SEQ ID NO:22:

```
Met Leu Arg Leu Leu Phe Thr Leu Val Leu Leu Ala Leu His Gly Gln
1               5                   10                  15

Ser Val Gly Ala Ser Arg Asp Tyr Val His Val Arg Leu Leu Ser Tyr
                20                  25                  30

Arg Gly Asp Pro Leu Val Phe Lys His Thr Phe Ser Gly Val Arg Arg
            35                  40                  45

Pro Phe Thr Glu Leu Gly Trp Ala Ala Cys Arg Asp Trp Asp Ser Met
        50                  55                  60

His Cys Thr Pro Phe Trp Ser Thr Asp Leu Glu Gln Met Thr Asp Ser
65                  70                  75                  80

Val Arg Arg Tyr Ser Thr Val Ser Pro Gly Lys Glu Val Thr Leu Gln
                85                  90                  95
```

-continued

```
Leu His Gly Asn Gln Thr Val Gln Pro Ser Phe Leu Ser Phe Thr Cys
            100                 105                 110

Arg Leu Gln Leu Glu Pro Val Val Glu Asn Val Gly Leu Tyr Val Ala
        115                 120                 125

Tyr Val Val Asn Asp Gly Glu Arg Pro Gln Gln Phe Phe Thr Pro Gln
    130                 135                 140

Val Asp Val Val Arg Phe Ala Leu Tyr Leu Glu Thr Leu Ser Arg Ile
145                 150                 155                 160

Val Glu Pro Leu Glu Ser Gly Arg Leu Ala Val Glu Phe Asp Thr Pro
                165                 170                 175

Asp Leu Ala Leu Ala Pro Asp Leu Val Ser Ser Leu Phe Val Ala Gly
            180                 185                 190

His Gly Glu Thr Asp Phe Tyr Met Asn Trp Thr Leu Arg Arg Ser Gln
        195                 200                 205

Thr His Tyr Leu Glu Glu Met Ala Leu Gln Val Glu Ile Leu Lys Pro
    210                 215                 220

Arg Gly Val Arg His Arg Ala Ile Ile His His Pro Lys Leu Gln Pro
225                 230                 235                 240

Gly Val Gly Leu Trp Ile Asp Phe Cys Val Tyr Arg Tyr Asn Ala Arg
                245                 250                 255

Leu Thr Arg Gly Tyr Val Arg Tyr Thr Leu Ser Pro Lys Ala Arg Leu
            260                 265                 270

Pro Ala Lys Ala Glu Gly Trp Leu Val Ser Leu Asp Arg Phe Ile Val
        275                 280                 285

Gln Tyr Leu Asn Thr Leu Leu Ile Thr Met Met Ala Ala Ile Trp Ala
    290                 295                 300

Arg Val Leu Ile Thr Tyr Leu Val Ser Arg Arg Arg
305                 310                 315
```

(2) INFORMATION FOR SEQ ID NO:23:

(i) SEQUENCE CHARACTERISTICS:
        (A) LENGTH: 214 amino acids
        (B) TYPE: amino acid
        (D) TOPOLOGY: linear (ii) MOLECULE TYPE: protein (vii) IMMEDIATE SOURCE:
        (B) CLONE: tol.19

(ix) FEATURE:
        (A) NAME/KEY: Protein
        (B) LOCATION: 1..214
        (D) OTHER INFORMATION: /label= UL130

(xi) SEQUENCE DESCRIPTION: SEQ ID NO:23:

```
Met Leu Arg Leu Leu Leu Arg His His Phe His Cys Leu Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
        50                  55                  60

Pro Arg Ser Pro Leu Gln Phe Ser Gly Phe Gln Gln Val Ser Thr Gly
65                  70                  75                  80

Pro Glu Cys Arg Asn Glu Thr Leu Tyr Leu Leu Tyr Asn Arg Glu Gly
                85                  90                  95
```

```
Gln Thr Leu Val Glu Arg Ser Ser Thr Trp Val Lys Lys Val Ile Trp
                100                 105                 110

Tyr Leu Ser Gly Arg Asn Gln Thr Ile Leu Gln Arg Met Pro Gln Thr
            115                 120                 125

Ala Ser Lys Pro Ser Asp Gly Asn Val Gln Ile Ser Val Glu Asp Ala
        130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Ile
        210

(2) INFORMATION FOR SEQ ID NO:24:

(i) SEQUENCE CHARACTERISTICS:
        (A) LENGTH: 122 amino acids
        (B) TYPE: amino acid
        (D) TOPOLOGY: linear (ii) MOLECULE TYPE: protein (vii) IMMEDIATE SOURCE:
        (B) CLONE: tol.20

(ix) FEATURE:
        (A) NAME/KEY: Protein
        (B) LOCATION: 1..122
        (D) OTHER INFORMATION: /label= UL149

(xi) SEQUENCE DESCRIPTION: SEQ ID NO:24:

Met Val Asp Gln Cys Cys Tyr Arg His Leu His Arg Ser Leu Ser Gly
1               5                   10                  15

Gly Pro Asp Val Leu Tyr Ala Ala Gly Thr Gln Arg Glu Gln Gln
            20                  25                  30

Arg Leu Asp Lys Ser Leu Ala Ala Thr Ala Pro Ser Ala Val Ala Gly
        35                  40                  45

Pro Pro Ala Asp Arg Asp Val Val Asp His Arg Thr Glu Thr His Ala
    50                  55                  60

Tyr Glu Thr Pro Arg Tyr Ala Thr Arg Cys Leu Thr Arg Tyr Thr Thr
65                  70                  75                  80

Pro Val Arg Ser Ala Val Arg Arg Thr Thr Cys Gly Lys Arg Val Ala
                85                  90                  95

Ser Gln Ser Pro Pro Arg Ser Cys Leu Val Ala Pro Gln Ser Ser Pro
            100                 105                 110

Ala His Pro Pro Arg His Pro Glu Gly Gly
        115                 120

(2) INFORMATION FOR SEQ ID NO:25:

(i) SEQUENCE CHARACTERISTICS:
        (A) LENGTH: 642 amino acids
        (B) TYPE: amino acid
        (D) TOPOLOGY: linear (ii) MOLECULE TYPE: protein
```

(vii) IMMEDIATE SOURCE:
          (B) CLONE: tol.21

(ix) FEATURE:
         (A) NAME/KEY: Protein
         (B) LOCATION: 1..642
         (D) OTHER INFORMATION: /label= UL150

(xi) SEQUENCE DESCRIPTION: SEQ ID NO:25:

Met Gln Leu Cys Ser His Ser Ile Ser Ser Gln Arg His Val Ala Ser
1               5                   10                  15

Ser Met His Cys Arg Ser Arg His Gln Arg Thr Pro Pro Ser Ala Thr
            20                  25                  30

Thr His Gly Pro Cys Ala Pro Thr Ser Arg Ile Leu Arg Arg Leu Leu
            35                  40                  45

Thr Thr Arg Arg Phe Leu Pro Arg Thr Pro Ser Pro Ser Asn Thr Val
50                  55                  60

Cys Cys Ile Arg Arg Arg Leu His Glu Arg Thr Ile Arg His Ser Met
65                  70                  75                  80

Arg Cys Arg Arg Arg Asp Met Ala Ser Ser Ala Ser Thr Pro Val Ser
            85                  90                  95

His Thr Gln Pro Leu Ala Ala Asn His Arg Arg Ser Arg Ile Thr Tyr
            100                 105                 110

Ala Thr Thr Asp Pro Thr Asn Ser Pro Thr Ala Ser Pro Ala Lys Ser
            115                 120                 125

Asp Lys Leu Glu Ala Asp Ala Asp Pro Ala Leu His Arg Arg Pro Ala
            130                 135                 140

Ser Leu Leu Arg His Leu Phe Gln Pro Cys His Ala Gln Arg Gly Thr
145                 150                 155                 160

Ser Asn Arg Ala Thr Ser Gln Arg Ala Ser Leu Asn Ala Val His His
            165                 170                 175

Lys Leu Cys Gly Ala Met Ile Ser Ser Ser Cys Ser Thr Thr Cys Thr
            180                 185                 190

Pro Leu Ile Met Asp Leu Pro Ser Leu Ser Val Glu Leu Ser Ala Gly
            195                 200                 205

His Lys Lys Lys Glu Thr Pro Thr Glu Gly Gly Trp Gly Gly Glu Glu
    210                 215                 220

Gly Glu Asp Asp Val Leu Ala Thr Ile Arg Asn Thr Leu Ser Ala Pro
225                 230                 235                 240

Thr Ser Pro Ala Ala Ala Thr Thr His Arg Leu Ser Phe Pro Gly Glu
            245                 250                 255

Ser Thr Phe Cys Leu Thr Ala Val Ser Glu Cys Ser Gln Arg Arg Thr
            260                 265                 270

Ser Thr Ala Ala Leu Thr Pro Pro Pro Ala Val Ala Ala Ala Phe
            275                 280                 285

Ser Phe Ser Ser Thr Val Ser Glu Thr Gly Thr Phe Pro Gln Ser Thr
            290                 295                 300

Thr Gly Arg Thr Arg Val Asp Asp Thr Ala Val Val Thr Ala Gly Asp
305                 310                 315                 320

Pro Arg Ser Pro Val Thr His Val Thr Leu Leu Gln Ile Phe Arg Leu
            325                 330                 335

Arg Ser Ser Leu Leu Thr Ser Arg Ser Gly Gly Ala Leu Arg Gly Gly
            340                 345                 350

Glu His Glu Ala Ile Pro Lys Val Ala Ser Leu Phe Trp Thr Leu Leu
            355                 360                 365

-continued

```
Lys Ala Thr Gln Ile Val Glu Met Thr His Lys Thr Pro Ser Ala Asp
        370                 375                 380

Ser His Arg Asn Pro Gln Lys Tyr Thr Asp Arg Pro Gln Arg Leu Leu
385                 390                 395                 400

Leu Thr Ala Leu Ala Ile Trp Gln Arg Thr Tyr Asn Asp Thr Arg Ala
                405                 410                 415

Ala His Ala Pro Gln Val Arg Leu Leu Gly Asp Ile Leu Thr Tyr Arg
                420                 425                 430

Arg Pro Gln Thr Ala Thr Ala Ser Thr Lys Ala His Thr Gln Gln Gln
                435                 440                 445

Pro Glu Glu Pro Lys Gly Gln Gln Ile Trp Thr Gln Thr Ala Gly Gln
                450                 455                 460

Ala Ala Pro His Gly Asp Glu Pro His Ser Asp Gly Glu Leu Arg Arg
465                 470                 475                 480

Glu Ser His Ser Ala Pro Pro Thr Ser Arg Thr Leu Pro Asp Thr Ile
                485                 490                 495

Leu Ala Val Lys Arg Arg Ser Val Ala Gln Arg Ser His Val Arg Leu
                500                 505                 510

Asp Ala Lys Pro Gly Leu Asn Glu Arg Asp Gly Phe Arg Gln Arg Leu
                515                 520                 525

Leu Leu Pro Leu Ser Gly Tyr Phe Arg Ala Asn Glu Leu Arg Asn Gln
530                 535                 540

Gln Phe Met Gly Tyr Gly Thr Lys Asn Gly Leu Lys Asn Thr Trp Leu
545                 550                 555                 560

Thr Arg Pro Leu Gly Val Ala Gly Val Arg Glu Thr Ile Gly Glu
                565                 570                 575

Arg Gln Asp Arg Asn Val Ala Asp Ser Ala Thr Gln Arg Val Phe His
                580                 585                 590

Thr Leu Tyr Ala Ala Leu Gln Thr Val Arg Val Trp Tyr Thr Ala Leu
                595                 600                 605

Gly Thr Ala Trp Arg Thr Ser Gly Ser Arg Thr Arg Glu Ser Leu Phe
610                 615                 620

Asp Gly Pro Arg Arg Arg Asp Arg Gln Ala Ala Arg Leu Arg Arg Leu
625                 630                 635                 640

Glu Leu
```

(2) INFORMATION FOR SEQ ID NO:26:

(i) SEQUENCE CHARACTERISTICS:
        (A) LENGTH: 336 amino acids
        (B) TYPE: amino acid
        (D) TOPOLOGY: linear (ii) MOLECULE TYPE: protein (vii) IMMEDIATE SOURCE:
        (B) CLONE: tol.22

(ix) FEATURE:
        (A) NAME/KEY: Protein
        (B) LOCATION: 1..336
        (D) OTHER INFORMATION: /label= UL151

(xi) SEQUENCE DESCRIPTION: SEQ ID NO:26:

```
Met Val Phe Val Ser Gly Thr Ala Leu Gly Thr Gly Phe His Arg Ala
1               5                   10                  15

Glu Gly Ser Phe Cys Gly Cys Glu Gly Arg Ser Phe Phe Arg Thr Leu
                20                  25                  30
```

-continued

```
Gly Thr Gly Leu Gly Asp Gly Gly Cys Ala Gly Arg Arg Trp Xaa Arg
             35                  40                  45

Xaa Val Ala Gly Thr Gly Ile Thr Leu Gly Thr Gly Thr Arg Gly Pro
 50                  55                  60

Gly Leu Arg Asp Gly Gly Asp Gly Gly Val Cys Gly Glu Asp Gly Gly
 65                  70                  75                  80

Leu Leu Arg Arg Gly Arg Gly Leu Ala Gly Pro Ala Val Ala Gly Val
                 85                  90                  95

Cys Gly Asp Gly Gly Leu Leu Gln Arg Arg Gly Leu Arg Gly Gln Glu
            100                 105                 110

Cys Ala Xaa Pro Gly Gly Phe Ala Gly Gly His Gly Thr Gly Gly Gly
            115                 120                 125

Gly Asp Ser Thr Asn His Thr His Thr Gln Leu Thr Ser Ala Val Ala
130                 135                 140

Leu Ser Glu Pro Pro Leu Phe Phe Ile Asn Val Leu Ile Pro Pro Ala
145                 150                 155                 160

Tyr Thr Arg Asn Ala Ala Cys Ser Tyr Ala His Thr Leu Ser Leu His
                165                 170                 175

Ser Asp Met Leu Leu Arg Leu Cys Thr Ala Ala Ala Asp Thr Ser Gly
            180                 185                 190

His Arg His Leu Pro Pro His Met Ala His Val Leu Arg Arg Pro Ala
            195                 200                 205

Ser Tyr Val Val Cys Ser Gln His Gly Ala Phe Phe Pro Ala Arg His
210                 215                 220

Leu His Arg Thr Pro Ser Ala Ala Phe Ala Val Ala Ser Thr Arg Glu
225                 230                 235                 240

Gln Tyr Ala Thr Ala Cys Ala Val Ala Ala Thr Trp Pro Pro Arg
                245                 250                 255

Leu Pro His Leu Phe Arg Thr Pro Asn Leu Trp Leu Pro Thr Thr Asp
            260                 265                 270

Val Gln Gly Ser Arg Thr Arg Arg Pro Ile Pro Pro Ile Leu Gln Arg
            275                 280                 285

Pro Arg Pro Pro Ser Gln Thr Ser Trp Lys Pro Thr Gln Thr Gln His
290                 295                 300

Ser Ile Asp Ala Arg Pro Arg Cys Cys Ala Thr Ser Ser Ser Pro Ala
305                 310                 315                 320

Thr Pro Asn Ala Ala Leu Pro Thr Glu Pro His Pro Arg Gly Leu Pro
                325                 330                 335
```

(2) INFORMATION FOR SEQ ID NO:27:

(i) SEQUENCE CHARACTERISTICS:
        (A) LENGTH: 270 amino acids
        (B) TYPE: amino acid
        (D) TOPOLOGY: linear (ii) MOLECULE TYPE: protein (vii) IMMEDIATE SOURCE:
        (B) CLONE: tol.23

(ix) FEATURE:
        (A) NAME/KEY: Protein
        (B) LOCATION: 1..270
        (D) OTHER INFORMATION: /label= UL132

(xi) SEQUENCE DESCRIPTION: SEQ ID NO:27:

```
Met Pro Ala Leu Arg Gly Pro Leu Arg Ala Thr Phe Leu Ala Leu Val
 1               5                  10                  15
```

-continued

```
Ala Phe Gly Leu Leu Leu Gln Ile Asp Leu Ser Asp Ala Thr Asn Val
            20                  25                  30

Thr Ser Ser Thr Lys Val Pro Thr Ser Thr Ser Asn Arg Asn Asn Val
        35                  40                  45

Asp Asn Ala Thr Ser Ser Gly Pro Thr Thr Gly Ile Asn Met Thr Thr
    50                  55                  60

Thr His Glu Ser Ser Val His Asn Val Arg Asn Asn Glu Ile Met Lys
65                  70                  75                  80

Val Leu Ala Ile Leu Phe Tyr Ile Val Thr Gly Thr Ser Ile Phe Ser
                85                  90                  95

Phe Ile Ala Val Leu Ile Ala Val Val Tyr Ser Ser Cys Cys Lys His
            100                 105                 110

Pro Gly Arg Phe Arg Phe Ala Asp Glu Glu Ala Val Asn Leu Leu Asp
        115                 120                 125

Asp Thr Asp Asp Ser Gly Gly Ser Ser Pro Phe Gly Ser Gly Ser Arg
    130                 135                 140

Arg Gly Ser Gln Ile Pro Ala Gly Phe Cys Ser Ser Ser Pro Tyr Gln
145                 150                 155                 160

Arg Leu Glu Thr Arg Asp Trp Asp Glu Glu Glu Ala Ser Ala Ala
                165                 170                 175

Arg Glu Arg Met Lys His Asp Pro Glu Asn Val Ile Tyr Phe Arg Lys
            180                 185                 190

Asp Gly Asn Leu Asp Thr Ser Phe Val Asn Pro Asn Tyr Gly Arg Gly
        195                 200                 205

Ser Pro Leu Thr Ile Glu Ser His Leu Ser Asp Asn Glu Glu Asp Pro
    210                 215                 220

Ile Arg Tyr Tyr Val Ser Val Tyr Asp Glu Leu Thr Ala Ser Glu Met
225                 230                 235                 240

Glu Glu Pro Ser Asn Ser Thr Ser Trp Gln Ile Pro Lys Leu Met Lys
            245                 250                 255

Val Ala Met Gln Pro Val Ser Leu Arg Asp Pro Glu Tyr Asp
            260                 265                 270
```

HUMAN CYTOMEGALOVIRUS DNA SEQUENCES

This is a divisional of application U.S. Ser. No. 08/926,922 filed Sep. 10, 1997 now U.S. Pat. No. 5,925,751, which is a divisional of U.S. Ser. No. 08/414,926 filed Mar. 31, 1995 now U.S. Pat. No. 5,721,354.

TECHNICAL FIELD

This invention pertains to the field of virology, specifically to the diagnosis, treatment and prevention of viral infections in humans. More specifically, this invention relates to the diagnosis, treatment and prevention of human cytomegalovirus infections.

BACKGROUND

Human cytomegalovirus (HCMV) is a ubiquitous agent in human populations. Infections are generally asymptomatic, but there can be serious medical sequelae in immunocompromised individuals and in congenitally infected newborns. In immunocompromised individuals, HCMV infection can result in interstitial pneumonia, retinitis progressing to blindness and disseminated infection. Infections in newborns can be severely damaging, with multiple organ involvement including the central nervous system and may also result in auditory damage. The mechanisms of pathogenesis are not understood, although it is believed that host factors, such as cellular and/or humoral immune responses might be involved. See, Alford and Britt, "The Human Herpesviruses", eds Roizman, B., R. J. Whitley and C. Lopez, Raven Press, New York, 1993, pp 227–55. It has also been speculated that genetic variability (either structural or antigenic or both) among different strains of HCMV could be responsible for the variance in clinical manifestations observed. Pritchett, *J. Virol.* 36:152–61(1980); Lehner, *J. Clin. Microbiol.* 29:2494–2502(1991); Fries, *J. Infect. Dis.* 169:769–74(1994).

Considerable attention has been focused recently on the analysis of strain variation among HCMV isolates. Some twenty different HCMV strains have been isolated and differentiated by restriction analysis of PCR amplified DNA fragments. Chou, *J. Infect. Dis.* 162:738–42(1990).

One strain, the Towne strain, has been developed into a live, attenuated vaccine and administered with some success in renal transplant patients. See Quinnan, *Annals of Int. Med.* 101:478–83(1984); Plotkin, *Lancet* 1:528–30(1984). However, Towne strain vaccines who were directly challenged by low-passaged Toledo strain wild-type virus in one study were found to resist challenge doses of only 10 plaque-forming units (pfu) or less. Plotkin, *J. Infect. Dis.* 159:860–65(1989). Therefore, it appears the Towne strain may be overly attenuated, i.e., genetically modified so extensively resulting from serial passage in cell culture that it has lost significant immunogenicity presumably due to the loss of genetic information during the cell passage. Advantageously however, the Towne strain has never been shown to reactivate.

DNA sequence heterogeneity between the Towne strain and another strain of HCMV, AD169, has been found. Pritchett, *J. Virol.* 36:152–61(1980). (A restriction map of the AD 169 HCMV genome is disclosed in U.S. Pat. No. 4,762,780.) Variation in the DNA content among other isolated strains of HCMV has also been detected. Huang, *Yale J. Biol. and Med.* 49:29–43(1976). Cleavage patterns of restriction enzyme digests of HCMV DNA of various strains has been analyzed. Kilpatrick, *J. Virol.* 18:1095–1105 (1976); LaFemina, "Structural Organization of the DNA Molecules from Human Cytomegalovirus" in *Animal Virus Genetics*, eds. Field, B N and R. Jaenish, Academic Press, NY (1980); Chandler, *J. Gen. Virol.* 67:2179–92(1986); Zaia, *J. Clin. Microbiol.* 28:2602–07(1990). However, although the gross structural organization of the HCMV genome has been determined and strain-to-strain restriction site polymorphism mapped for many of the strains, strain-to-strain differences in the DNA sequences of the HCMV genome have not been determined. Only partial sequences have been deduced and compared. For example, the DNA and amino acid sequences of the envelope glycoprotein B [gpUL55(gB)] of both Towne and AD169 strains have been deduced, see Spaete, *Virology* 167:207–25(1988), and compared with various clinical isolates, see Chou, *J. Infect. Dis.* 163:1229–34(1991), to identify conserved regions and regions of variability. In addition, DNA sequence analysis of certain regions of the gp58/116 gene [gpUL55(gB)], the IMP gene and the IE-1/2 enhancer/promoter has been accomplished. Lehner, *J. Clin. Microbiol.* 29:2494–2502(1991).

Whereas the complete DNA sequence of the AD169 strain of HCMV has been deduced, (EMBL Accession No. X17403), the complete DNA sequence of the Towne strain has not to our knowledge been deduced. However, it has been speculated that AD169 and another laboratory strain, Davis, are missing two to four kilobase pairs (kb) of DNA sequence compared to the Towne strain at the extreme internal portions of both L repeats. LeFemina, supra, at 52–53.

The public health impact of HCMV infections has not been well controlled by current treatment strategies or available antiviral chemotherapies. Preventative vaccine strategies are likely to prove efficacious because of the observations that seropositive renal allograft recipients are protected from severe HCMV disease and maternal immunity protects the fetus from disease after intrauterine infection. Marshall and Plotkin, "Cytomegalovirus Vaccines" in The Human Herpesviruses, eds Roizman, B., R. J. Whitley and C. Lopez, Raven Press, New York, 1993, pps 381–95. However, an additional obstacle to the development of a vaccine for HCMV is the lack of an animal model system that can be used to test the safety and efficacy of vaccine candidates.

There remains a need in the art for efficacious vaccines for the prophylactic treatment of HCMV in humans.

SUMMARY OF THE INVENTION

In one aspect, the invention provides novel HCMV DNA sequences not heretofore recognized or known in the art. These novel HCMV sequences were isolated from the Toledo and Towne strains of HCMV and comprise DNA that is not shared by reference strain AD169 of HCMV. Accordingly, in this aspect the invention provides novel, isolated, Toledo strain HCMV DNA sequences. As used herein, "isolated" means substantially free from other viral DNA sequences with which the subject DNA is typically found in its native, i.e., endogenous, state. These novel Toledo HCMV DNA sequences are characterized by comprising the same or substantially the same nucleotide sequence as in FIG. 1 (SEQ ID NO:6), or active fragments thereof. The DNA sequences may include 5' and 3' non-coding sequences flanking the coding sequence. The DNA sequences may be in inverted orientation with respect to the orientation shown in FIG. 1. Segments or fragments of the DNA sequence shown in FIG. 1 (SEQ ID NO:6) may be rearranged or inverted internally. The DNA sequences of the invention also comprise nucleotide sequences capable of hybridizing under stringent conditions, or which would be capable of hybridizing under said conditions but for the degeneracy of the genetic code to a sequence corresponding to the sequence of FIG. 1. FIG. 1 (SEQ ID NO:6) illustrates the DNA sequence of the novel Toledo strain HCMV. Twenty one open reading frames (ORFs) were identified in this sequence. The putative amino acid sequences of these novel Toledo strain HCMV ORFs are enumerated in sequence identification numbers 7 through 27, pages 58 through 78, infra. In FIG. 1, the beginning and ending of the 21 ORFs are identified by the arrows and the designations "UL133", "UL134", etc. (see infra.). In rearranged sequences of the invention, novel open reading frames may be created or destroyed.

In another aspect, the invention provides additional novel HCMV DNA sequences not heretofore recognized or known in the art. These additional sequences were isolated from the Towne strain of HCMV and comprise DNA that is not shared by the AD169 strain or by the Toledo strain of RCMV. Accordingly, in this aspect the invention provides novel Towne strain HCMV sequences. These novel Towne HCMV DNA sequences are characterized by as comprising the same or substantially the same nucleotide sequence as in FIG. 2 (SEQ ID NO: 1), or active fragments thereof. The DNA sequence may include 5' and 3' non-coding sequences flaring the coding sequence. The DNA sequences of the invention also comprise nucleotide sequences capable of hybridizing under stringent conditions, or which would be capable of hybridizing under said conditions but for the degeneracy of the genetic code to a sequence corresponding to the sequence of FIG. 2 (SEQ ID NO:1). FIG. 2 (SEQ ID NO:1) illustrates the DNA sequence of the novel Towne strain HCMV. Four ORFs were identified in this sequence. The putative amino acid sequences of these novel ORFs are enumerated in sequence identification numbers 2 through 5, pages 42 through 45 infra. In FIG. 2, the beginning and ending of the 4 ORFs are identified by the arrows and the designations UL147, UL152, UL153 and UL154.

It is understood that the DNA sequences of this invention may exclude some or all of the signal and/or flanking sequences. In addition, the DNA sequences of the present invention may also comprise DNA capable of hybridizing under stringent conditions, or which would be capable of hybridizing under such conditions but for the degeneracy of the genetic code, to an isolated DNA sequence of FIG. 1 or FIG. 2. (SEQ ID NOS:6 and 1). As used herein, "stringent conditions" means conditions of high stringency, for example 6×SSC, 0.2% polyvinylpyrrolidone, 0.2% Ficoll, 0.2% bovine serum albumin, 0.1% sodium dodecyl sulfate, 100 μg/ml salmon sperm DNA and 15% formamide at 68 degrees C. (See Materials and Methods, Part C, infra.)

Accordingly, the DNA sequences of this invention may contain modifications in the non-coding sequences, signal sequences or coding sequences, based on allelic variation, species or clinical isolate variation or deliberate modification. Using the sequences of FIG. 1 and 2 (SEQ ID NOS:6 and 1), it is within the skill in the art to obtain other modified DNA sequences: the sequences can be truncated at their 3'-termini and/or their 5'-termini, the gene can be manipulated by varying individual nucleotides, while retaining the original amino acid(s), or varying the nucleotides, so as to modify amino acid(s). Nucleotides can be substituted, inserted or deleted by known techniques, including for example, in vitro mutagenesis and primer repair. In addition, short, highly degenerate oligonucleotides derived from regions of imperfect amino acid conservation can be used to identify new members of related viral and cellular families. RNA molecules, transcribed from a DNA of the invention as described above, are an additional aspect of the invention.

In another aspect, the invention provides novel HCMV proteins, which are substantially free from other HCMV proteins with which they are typically found in their native state. These novel HCMV proteins comprise the open reading frames (ORFs) UL133 (SEQ ID NO:7), UL134 (SEQ ID NO:8), UL135 (SEQ ID NO:9), UL136 (SEQ ID NO:10), UL137 (SEQ ID NO:11), UL138 (SEQ ID NO:12), UL139 (SEQ ID NO:13), UL140 (SEQ ID NO:14), UL141 (SEQ ID NO:15), UL142 (SEQ ID NO:16), UL143 (SEQ ID NO:17), UL144 (SEQ ID NO:18), UL145 (SEQ ID NO:19), UL146 (SEQ ID NO:20), UL147 (SEQ ID NO:21), UL148 (SEQ ID NO:22), UL149 (SEQ ID NO:24), UL150 (SEQ ID NO:25), and/or UL151 (SEQ ID NO:26) identified in the novel Toledo strain DNA sequence and UL147 (SEQ ID NO:2), UL152 (SEQ ID NO:3), UL153 (SEQ ID NO:4) and/or UL154 (SEQ ID NO:5) identified in the novel Towne strain DNA sequence. Two additional HCMV ORIs were identified in the novel Toledo strain DNA sequence, UL130 and UL132 (SEQ ID NOS:23 and 27). These two sequences are also present in AD169 (see FIG. 5). The proteins may be produced by recombinant genetic engineering techniques. They may additionally be purified from cellular sources infected with HCMV. They may also be synthesized by chemical techniques. One skilled in the art could apply a combination of the above-identified methodologies to synthesize the protein. Additionally, analogs of the HCMV proteins of the invention are provided and include truncated polypeptides, e.g., mutants in which there are variations in the amino acid sequence that retain biological activity, as defined below, and preferably have a homology of at least 80%, more preferably 90%; and most preferably 95%, with the corresponding regions of the HCMV Towne or Toledo amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27). Examples include polypeptides with minor amino acid variations from the native amino acid sequences of HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27); in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) nonpolar=alanine, valine, leucine, isoleucine, proline, phenylalanine, methionine, typtophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on activity or functionality.

Using the Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27) it is within the a skill in the art to obtain other polypeptides or other DNA sequences encoding the HCMV Toledo or Towne protein from clinical isolates of HCMV. For example, the structural gene can be manipulated by varying individual nucleotides, while retaining the correct amino acid(s), or varying the nucleotides, so as to modify the amino acids, without loss of activity. Nucleotides can be substituted, inserted, or deleted by known techniques, including, for example, in vitro mutagenesis and primer repair. The structural gene can be truncated at its 3'-terminus and/or its 5'-terminus while retaining its activity. It also may be desirable to remove the region encoding the signal sequence, and/or to replace it with a heterologous sequence. It may also be desirable to ligate a portion of the HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27), particularly that which includes the amino terminal domain to a heterologous coding sequence, and thus to create a fusion peptide of HCMV Toledo or Towne.

In designing such modifications, it is expected that changes to nonconserved regions of the HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27) will have relatively smaller effects on activity, whereas changes in the conserved regions, and particularly in or near the amino terminal domain are expected to produce larger effects. Amino acid residues that are conserved between the HCMV Toledo or Towne amino acid sequences (SEQ ID NOS:2, 3, 4, 5, 7, 8, 9, 10, 11, 12, 14, 15, 17, 18, 19, 21, 22, 23, 24, 25, 26, and 27) and at least two other sequences, for example, from HCMV clinical isolates are not expected to be candidates for substitution. A residue which shows conservative variations among the HCMV sequences and at least two of the other sequences is expected to be capable of similar conservative substitution of the HCMV sequences. Similarly, a residue which varies nonconservatively among the HCMV sequences and at least three of the other sequences is expected to be capable of either conservative or nonconservative substitution. When designing substitutions to the HCMV sequences, replacement by an amino acid which is found in the comparable aligned position of one of the other sequences is especially preferred.

Additionally provided by this invention is a recombinant DNA vector comprising vector DNA and a DNA sequence encoding an HCMV Toledo polypeptide or HCMV Towne polypeptide. The vector provides the HCMV Toledo or Towne DNA in operative association with a regulatory sequence capable of directing the replication and expression of an HCMV Toledo or Towne protein in a selected host cell. Host cells transformed with such vectors for use in expressing recombinant HCMV Toledo or Towne proteins are also provided by this invention. Also provided is a novel process for producing recombinant HCMV Toledo or Towne proteins or active fragments thereof. In this process, a host cell line transformed with a vector as described above containing a DNA sequence (SEQ ID NOS:1 and 6) encoding expression of an HCMV Toledo or Towne protein in operative association with a suitable regulatory sequence capable of directing replication and controlling expression of an HCMV Toledo or Towne protein is cultured under appropriate conditions permitting expression of the recombinant DNA. The expressed protein is then harvested from the host cell or culture medium using suitable conventional means. This novel process may employ various known cells as host cell lines for expression of the protein. Currently preferred cells are mammalian cell lines, yeast, insect and bacterial cells. Especially preferred are mammalian cell lines.

The practice of the invention will employ, unless otherwise indicated, conventional techniques of molecular biology, microbiology, recombinant DNA manipulation and production, and immunology, which are within the skill of the art. Such techniques are explained fully in the literature.

See, e.g., Sambrook, *Molecular Cloning: A Laboratory Manual,* Second Edition (1989); *DNA Cloning,* Volumes I and II (D. N. Glover, Ed. 1985); *Oligonucleotide Synthesis* (M. J. Gait, Ed. 1984); *Nucleic Acid Hybridization* (B. D. Hames and S. J. Higgins, Eds. 1984); *Transcription and Translation* (B. D. Hames and S. J. Higgins, Eds. 1984); *Animal Cell Culture* (R. I. Freshney, Ed. 1986); *Immobilized Cells and Enzymes* (IRL Press, 1986); B. Perbal, *A Practical Guide to Molecular Cloning* (1984); the series, *Methods in Enzymology* (Academic Press, Inc.); *Gene Transfer Vectors for Mammalian Cells* (J. H. Miller and M. P. Calos, Eds. 1987, Cold Spring Harbor Laboratory), *Methods in Enzymology,* Volumes 154 and 155 (Wu and Grossman, and Wu, Eds., respectively), (Mayer and Walker, Eds.) (1987); *Immunochemical Methods in Cell and Molecular Biology* (Academic Press, London), Scopes, (1987); *Protein Purification: Principles and Practice,* Second Edition (Springer-Verlag, N.Y.); and *Handbook of Experimental Immunology,* Volumes I–IV (D. M. Weir and C. C. Blackwell, Eds 1986). All patents, patent applications and publications mentioned herein, both supra and infra, are hereby incorporated by reference.

Additionally provided by this invention are compositions for detecting HCMV infections in humans. These compositions comprise probes having at least one single-stranded fragment of at least 10 bases in length, more preferably 15 bases in length, of the novel Toledo sequence, and fragments hybridizing to these single-stranded fragments under stringent hybridization conditions and non-cross-hybridizing with human DNA. Additionally, these compositions comprise at least one single-stranded fragment of at least 10 bases in length, more preferably 15 bases in length, of the novel Towne sequence, and fragments hybridizing to these single-stranded fragments under stringent hybridizing with human DNA. Such probe compositions may additionally comprise a label, attached to the fragment, to provide a detectable signal, as is taught in U.S. Pat. No. 4,762,780.

Further provided by this invention are methods for detecting an HCMV infection in a human host. Such methods comprise combining under predetermined stringency conditions a clinical sample suspected of containing HCMV DNA with at least one single-stranded DNA fragment of the novel Toledo or Towne strain of HCMV having at least 10 bases, more preferably 15 bases, and being non-ross-hybridizing with human DNA, and detecting duplex formation between the single-stranded Toledo or Towne strain HCMV fragments and the sample DNA. Alternatively, PCR may be used to increase the viral nucleic acid copy number by amplification to facilitate the identification of HCMV in infected individuals. In such case, the single-stranded Toledo or Towne strain DNA sequence fragments of the present invention can be used to construct PCR primers for PCR-based amplification systems for the diagnosis of HCMV. Such systems are well known in the art. See for example, U.S. Pat. No. 5,008,182 (detection of AIDS associated virus by PCR) and Hedrum, PCR Methods and Applications 2:167–71(1992) (detection of *Chlamydia trachomatis* by PCR and immunomagnetic recovery).

The DNA sequences of this invention may also be used to prepare immunizing compositions. The novel Toledo DNA sequences are recombined into the Towne strain or AD169 strain of HCMV and these recombinant viruses tested for growth properties in endothelial cells or in human tissues transplanted into SCID mice or tested in the rat eye model. Mocarski, *Proc. Nat. Acad. Sci* 90:104–08(1993). Such recombinants will show increased immunogenicity over that shown by the Towne-125 strain currently in use in humans, without exhibiting the full virulence shown by the Toledo-1 strain. Therefore, a further aspect of the invention is immunizing compositions comprising either the Towne strain or the AD169 reference strain of HCMV to which the novel Toledo DNA sequence, or analogs or fragments thereof, have been added, resulting in increased immunogenicity of the recombinant virus. The invention also includes a method for the prophylactic treatment of HCMV in humans comprising administering to a human patient an immunogenically inducing effective amount of an immunizing composition of the invention in a suitable pharmaceutical carrier. Still another aspect of the invention is a method of stimulating an immune response against CMV by administering to a patient an immunogenically inducing effective amount of an immunizing composition of the invention in a suitable pharmaceutical vehicle.

Other aspects and advantages of this invention are described in the following detailed description.

BRIEF DESCRIPTION OF THE DRAWINGS

FIGS. 1A–T illustrates the novel Toledo DNA sequence of the invention isolated from the Toledo strain of HCMV. The arrows indicate the beginnings and ends of nucleotide sequences encoding the 21 putative amino acid sequences identified.

FIGS. 2A–2E illustrates the novel Towne DNA sequence of the invention isolated from the Towne strain of HCMV. The arrows indicate the beginnings and ends of the nucleotide sequences encoding the 4 putative amino acid sequences identified.

FIG. 3 is a schematic representation of a Southern blot of restriction enzyme digested Towne and Toledo HCMV strain DNA as detailed in Example 1. The arrow indicates a 5 kbp (kilobase pair) band of Toledo DNA on the BamHI digest that is lacking in the Towne DNA, signifying the presence of additional Toledo DNA sequence.

FIG. 4 illustrates a composite autoradiograph of the restriction enzyme digested DNA from AD169, Towne, Toledo and five clinical isolates of HCMV as described in Example 3.

FIG. 5 is a schematic presentation of the novel open reading frames identified in the novel Toledo and Towne DNA sequences.

FIG. 6 is a schematic illustration of the relative positions of novel sequences identified in Toledo genomic DNA, Towne genomic DNA in a comparison with AD169 strain genomic DNA.

DETAILED DESCRIPTION

A. Introduction

The invention provides two novel HCMV DNA sequences, termed Toledo sequence and Towne sequence, not heretofore recognized or known in the art. The invention also provides immunization compositions and methods using the novel HCMV DNA sequences of the invention and also provides other diagnostic and therapeutic uses for the sequences and their protein products. The new DNA sequences were originally found in the Toledo and Towne strains of HCMV. Details of the sequences and structural characteristics are provided in the Examples below.

Most desirably, HCMV immunogenic compositions are provided that comprise reference strain AD169 or Towne to which the novel Toledo DNA sequences, or analogs or fragments thereof, have been added in order to increase the imunogenicity of the overly-attenuated strain. Thus, one aspect of this invention includes isolated DNA and corresponding RNA sequences as disclosed in FIGS. 1 and 2 (SEQ ID NOS:6 and 1). As used herein, "isolated" means substantially free from other nucleotide or polypeptide sequences with which the subject nucleotide sequence or polypeptide sequence is typically found in its native, i.e., endogenous, state. In another aspect, the invention comprises isolated HCMV Towne or Toledo protein encoded by the respective HCMV Towne or Toledo DNA sequences (SEQ ID NOS:2, 3, 4, 5, 7, 8, 9, 10, 11, 12, 13, 14, 15, 16, 17, 18, 19, 20, 21, 22, 23, 24, 25, 26, and 27).

Another aspect of this invention includes diagnostic assays for the detection of HCMV strain variants. In brief, such diagnostic assays include the use of DNA sequence fragments of the invention as primers for amplifying HCMV related nucleic acids in a polymerase chain reaction (PCR) or by direct detection by hybridization. The diagnostic assays of the invention may also include the use of specific antibodies against the novel ORFs encoded by the Toledo or Towne DNA sequences disclosed here. Yet another aspect of the invention is the use of the novel DNA sequences modified with a unique restriction site, to act as vaccine markers.

It is anticipated that the invention will enable the production of vaccines that offer advantages over the current HCMV vaccine, which is overly attenuated and therefore not consistently effective in eliciting an immune response. More specifically, the introduction or insertion of the novel Toledo strain sequences of the present invention into the Towne strain or into the AD169 strain will result in the introduction of specific DNA sequences in the HCMV Towne genome that are not possible using the cell passage vaccines. Importantly for vaccine production, this enables precise measurement of the degree of attenuation introduced by different fragments of the DNA sequences of the invention, thereby enabling the controlled modification in the attenuation of the Towne strain that is needed in the art to correct the Towne's strain's overly attenuated characteristic and improve its function as an immunogenic composition.

B. Recombinant AD169 or Towne HCMV

Recombinant AD169 or Towne DNA is derived by co-transfecting a plasmid containing the novel Toledo sequence, or analogs or fragments thereof, and a selectable marker such as gpt or β-galactosidase in primary fibroblast cells, or other cell lines known to be permissive for growth of CMV. Recombinant viruses are selected by growth in media containing mycophenolic acid or identified by blue plaque phenotypes after applying a chromogenic substrate such as X-gal. Recombinant viruses are plaque purified and characterized by restriction enzyme analysis and Southern blotting procedures. The novel HCMV Toledo sequence, or analogs or fragments thereof, may be vised unmodified with respect to the endogenous promoter and transcription termination signals. Alternatively, the HCMV Toledo strain DNA coding region can be placed under transcriptional control of a promoter such as the CMV (cytomegalovirus) major immediate early promoter, the SV40 early promoter or some other viral or cellular promoter that generates adequate levels of expression, as discussed herein.

Modified Towne or AD169 strain HCMV is grown in tissue culture cells. For a experiments with mammals, not including humans, cells such as human foreskin fibroblasts (HF) or MRC-5 cells are used to propagate the virus. The virus is harvested from cultures of these cells and the isolated recombinant virus is then be further studied for its ability to elicit an immune response and provide protection against HCMT infection.

For use in humans, the recombinant virus is produced from an HCMV approved cell line in large scale amounts.

Such cells include MRC-5 or WI-38 cells (both are primary human diploid fibroblasts). The recombinant virus is generated in the production cell line by transfection of viral DNA or capsids prepared from recombinant virus isolated from another cell line. The method of transfection should prevent the contamination of FDA approved cells with adventitious agents or contaminants from a non-qualified cell line. A HCMV virus produced from the above cell lines will be used to infect progressively larger flasks of tissue culture cells. Infected cells will be used as subsequent inoculums. Viable infected tissue culture cells are removed from the tissue culture vessels using trypsin and added to a 1 to 100 fold (or more) excess of uninfected cells to accomplish progressively larger inoculations. Once an optimal yield is obtained the virus will be harvested from the tissue culture cells. This process can be repeated until a large scale production is achieved. Infected cells will be removed from the tissue culture vessel and disrupted using for example, sonication, dounce homogenization or some combination of the above. The viruses are then isolated from cellular material using centrifugation techniques known in the art. Once the virus is isolated a stabilizing agent is added, such as a carbohydrate or carbohydrate derivative and the virus is then aliquoted and lyophilized.

C. Immunogenic Compositions

Immunogenic compositions can be administered to subjects to prevent HCMV infections. The immunogenic compositions prevent HCMV infections by stimulating the immune system with an attenuated virus incapable of fully manifesting the disease. A major advantage of the HCMV immunogenic compositions provided herein is that its increased degree of immunogenicity will result in move effective prevention of an HCMV infection in the population.

The Towne strain of HCMV will preferably serve as the parent strain due to its proven inability to reactivate. To make HCMV immunogenic compositions, full, truncated and/or modified novel Toledo DNA sequences are introduced into a HCMV AD169 or Towne strain virus as discussed herein. The effectiveness of the immunogenic composition in preventing HCMV infections will be measured in humans. Humans will be first inoculated with PFU's ranging from 100–20,000 PFU of mutant virus per inoculation, PFUs are measured as discussed herein. After the first inoculation, a second booster injection of similar or increased dosage usually may be given. Subjects will be exposed to wild-type HCMV after the first or second inoculation and the occurrence of CMV infections observed. Potential side effects of the vaccine will be monitored in volunteer adults previously exposed to CMV, before inoculating subjects that have not ever developed CMV infections. Attenuated virus is used without an adjuvant and with a physiologically suitable carrier.

As is known in the art and discussed herein, the novel DNA is inserted into the Towne or AD169 viral genome using, for example, homologous recombination techniques. The insertion is generally made into a gene which is non-essential in nature. Plasmid shuttle vectors that greatly facilitate the construction of recombinant viruses have been described. See, for example, Spaete and Mocarski, *Proc. Nat. Acad. Sci* 84:7213–17(1987). Expression of the polypeptide encoded by the novel Toledo DNA then occurs in cells or individuals which are immunized with the live recombinant virus.

Alternatively, the purified novel HCMV proteins may be employed in therapeutic and/or subunit immunogenic compositions for preventing and treating HCMV related conditions. Such pharmaceutical compositions comprise an immunogenically-inducing effective amount of one or more of the proteins of the present invention in admixture with a pharmaceutically acceptable carrier, for example an adjuvant/antigen presentation system such as alum. Other adjuvant/antigen presentation systems, for instance, MF59 (Chiron Corp.), QS-21 (Cambridge Biotech Corp.), 3-DMPL (3-Deacyl-Monophosphoryl Lipid A) (RibiImmunoChem Research, Inc.), clinical grade incomplete Freund's adjuvant (IFA), fasogenic liposomes, water soluble polymers or Iscoms (Immune stimulating complexes) may also be used. Other exemplary pharmaceutically acceptable carriers or solutions are aluminum hydroxide, saline and phosphate buffered saline. The composition can be systemically administered, preferably subcutaneously or intramuscularly, in the form of an acceptable subcutaneous or intramuscular solution. Also inoculation can be effected by surface scarification or by inoculation of a body cavity. The preparation of such solutions, having due regard to pH, isotonicity, stability and the like is within the skill in the art. The dosage regimen will be determined by the attending physician considering various factors known to modify the action of drugs such as for example, physical condition, body weight, sex, diet, severity of the condition, time of administration and other clinical factors. Exemplary dosage ranges comprise between about 1 $\mu$g to about 1000 $\mu$g of protein.

In practicing the method of treatment of this invention, an immunologically-inducing effective amount of protein is administered to a human patient in need of therapeutic or prophylactic treatment. An immunologically inducing effective amount of a composition of this invention is contemplated to be in the range of about 1 microgram to about 1 milligram per dose administered. The number of doses administered may vary, depending on the above mentioned factors.

D. Diagnostic Assays and Use as a Vaccine Marker

The novel Toledo and Towne DNA sequences of the present invention can be used in diagnostic assays to detect HCMV in a sample, to detect Toledo and Towne-like sequences and to detect strain differences in clinical isolates of HCMV using either chemically synthesized or recombinant Toledo or Towne DNA fragments. Additionally, the novel sequences can be used as a vaccine marker to differentiate between an individual or sample infected with or containing wild type HCMV and an individual or sample infected with or containing a HCMV vaccine, i.e., a live attenuated HCMV vaccine currently in use such as the Towne vaccine. In yet another embodiment, fragments of the DNA sequences can also be linked to secondary nucleic acids with sequences that either bind a solid support or other detection probes for use in diagnostic assays. In one aspect of the invention, fragments of the novel Toledo or Towne DNA sequences (SEQ ID NOS:1 and 3) comprising at least between 10 and 20 nucleotides can be used as primers to amplify nucleic acids using polymerase chain reaction (PCR) methods well known in the art and as probes in nucleic acid hybridization assays to detect target genetic material such as HCMV DNA in clinical specimens (with or without PCR). See for example, U.S. Pat. Nos. 4,683,202; 4,683,195; 5,091,310; 5,008,182 and 5,168,039. In an exemplary assay, a conserved region of the novel DNA sequence among virus variants is selected as the sequence to be amplified and detected in the diagnostic assay. Oligonucleotide primers at least substantially complementary to (but preferably identical with) the sequence to be amplified are constructed and a sample suspected of containing a HCMV nucleic acid sequence to be detected is treated with primers for each strand of HCMV nucleic acid sequence to be detected, four different deoxynucleotide triphosphates and a polymerization agent under appropriate hybridization conditions such that an extension product of each primer is synthesized that is complementary to the HCMV nucleic acid sequences suspected in the sample, which extension products synthesized from one primer, when separated from its complement can serve as a template for synthesis of the extension product of the other primer in a polymerase chain reaction. After amplification, the product of the PCR can be detected by the addition of a labeled probe, likewise constructed from the novel DNA sequence, capable of hybridizing with the amplified sequence as is well known in the art. See, e.g. U.S. Pat. No. 5,008,182.

In another embodiment the probes or primers can be used in a vaccine marker assay to detect a vaccine or wild type infection. Alternatively, introduction of a restriction site into the novel DNA sequence will provide a vaccine marker that can be used with PCR fragments to detect such differences in a restriction digest. Such procedures and techniques for detecting sequence variants, such as, point mutations with the expected location or configuration of the mutation, are known in the art and have been applied in the detection of sickle cell anemia, hemoglobin C disease, diabetes and other diseases and conditions as disclosed in U.S. Pat. No. 5,137, 806. These methods are readily applied by one skilled in the art to detect and differentiate between wild type and vaccine infections in HCMV.

In another embodiment the novel Toledo or Towne DNA sequences can be used in their entirety or as fragments to detect the presence of DNA sequences, related sequences, or transcription products in cells, tissues, samples and the like using hybridization probe techniques known in the art or in conjunction with one of the methods discussed herein. When used as a hybridization probe, fragments of the novel DNA sequences of the invention are preferably 50–200 nucleotides long, more preferably 100–300 nucleotides long and most preferably greater than 300 nucleotides long.

E. Vectors and Chimeric Virus Production

The novel DNA sequences of the invention can be expressed in different vectors using different techniques known in the art resulting in the generation of chimeric virus. Useful and known techniques include marker transfer or homologous recombination, direct in vitro ligation, defective vector technology and amplicon generation (see, e.g., Frenkel, N. et al., Gene Transfer and Cancer, edited by M. L. Pearson and N. L. Sternberg(1984), Kwong, A. D. and Frenkel, Virology 142, 421–425(1985); U.S. patent (Ser. No. 071923,015 by Roizman). Vectors used in such techniques include cosmids, plasmids, and infective or defective viruses. Such vectors are known in the art. (A cosmid as used herein is a plasmid containing a lambda bacteriophage cos site. The cos site is the cis signal for packaging lambda DNA. Therefore, a cosmid, unlike a plasmid, can be packaged with high efficiency into a lambda head in vitro. This technique allows cloning of very large (30–45 kbp) fragments of DNA.) The vectors can be either single stranded or double stranded and made of either DNA or RNA.

Generally, the DNA sequence is inserted into the vector alone or linked to other HCMV genomic DNA. In direct in vitro ligation applications, the isolated sequence alone is used. In homologous recombination and marker transfer flanking nucleic acid sequences are required to effect transfer of the sequence into a HCMV viral genome. For use in viral complementation using cosmids and other vectors discussed herein the sequence (or a fragment thereof) in a vector is preferably operatively linked to at least 1 kb of HCMV genomic nucleic acid and more preferably at least 5 kb of HCMV nucleic acid. The HCMV genomic nucleic acid can be on one side or both sides of the open reading frame. If only a specific region of the open reading frame is to be used to generate a mutant virus, an open reading frame or fragment thereof is inserted into a vector.

F. Novel Toledo and Towne Protein

Another aspect of the invention includes the isolated proteins encoded by the Toledo or Towne DNA sequence as taught herein. The proteins can be used to study and modify the life cycle of HCMV because they may encode surface glycoproteins that may be immunogenic and responsible for tissue tropism or influence the immune response in an infected individual. Such proteins could therefore be used in the production of a subunit vaccine against CMV. The construction of such CMV subunits vaccine candidates is known in the art. See, for example, Spaete, Virology 167:207–25(1988).

Twenty-one novel Toledo and four novel Towne proteins have been identified by ORF analysis. The novel Toledo proteins include UL130 (SEQ ID NO:23), UL132 (SEQ ID NO:27), UL133 (SEQ ID NO:7), UL134 (SEQ ID NO:8), UL135 (SEQ ID NO:9), UL136 (SEQ ID NO:10), UL137 (SEQ ID NO:11), UL138 (SEQ ID NO:12), UL139 (SEQ ID NO:13), UL140 (SEQ ID NO:14), UL141 (SEQ ID NO:15), UL142 (SEQ ID NO:16), UL143 (SEQ ID NO:17), UL144 (SEQ ID NO:18), UL145 (SEQ ID NO:19), UL146 (SEQ ID NO:20), UL147 (SEQ ID NO:21), UL148 (SEQ ID NO:22), UL149 (SEQ ID NO:24), UL150 (SEQ ID NO:25), and/or UL151 (SEQ ID NO:26). UL130 is encoded by nucleotides 13109 through 13753, as shown in FIG. 1. UL132 is encoded by nucleotides 11673 through 12485, as shown in FIG. 1. UL133 is encoded by nucleotides 51 through 824, as shown in FIG. 1. UL134 is encoded by nucleotides 541 through 1068, as shown in FIG. 1. UL135 is encoded by nucleotides 941 through 1927, as shown in FIG. 1. UL136 is encoded by nucleotides 2018 through 2740, as shown in FIG. 1. UL137 is encoded by nucleotides 2599 through 2890, as shown in FIG. 1. UL138 is encoded by nucleotides 2823 through 3332, as shown in FIG. 1. UL139 is encoded by nucleotides 3895 through 4302, as shown in FIG. 1. UL140 is encoded by nucleotides 4484 through 4828, as shown in FIG. 1. UL141 is encoded by nucleotides 5098 through 6375, as shown in FIG. 1. UL142 is encoded by nucleotides 6448 through 7368, as shown in FIG. 1. UL143 is encoded by nucleotides 7353 through 7631, as shown in FIG. 1. UL144 is encoded by nucleotides 8008 through 8538, as shown in FIG. 1. UL145 is encoded by nucleotides 8867 through 9169, as shown in FIG. 1. UL146 is encoded by nucleotides 9450 through 9803, as shown in FIG. 1. UL147 is encoded by nucleotides 9868 through 10347, as shown in FIG. 1. UL148 is encoded by nucleotides 10646 through 11596, as shown in FIG. 1. UL149 is encoded by nucleotides 15756 through 16124, as shown in FIG. 1. UL150 is encoded by nucleotides 15874 through 17802, as shown in FIG. 1. UL151 is encoded by nucleotides 17289 through 18299, as shown in FIG. 1.

The novel Towne proteins include UL147, UL152, UL153 and UL154 (SEQ ID NOS:2, 3, 4 and 5, respectively). UL147 is encoded by nucleotides 841 through 1321, as shown in FIG. 2. UL152 is encoded by nucleotides 1365 through 1721, as shown in FIG. 2. UL153 is encoded by nucleotides 2501 through 3337, as shown in FIG. 2. UL154 is encoded by nucleotides 3512 through 4711, as shown in FIG. 2.

"Toledo and/or Towne protein or proteins" as used herein refer to the above sequences, also enumerated in the sequence listing. "Toledo and/or Towne protein or proteins" also refers to an homologous protein from any strain or clinical isolate of HCMV, including HCMV proteins that are at least 90% homologous to the Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27). The Toledo or Towne protein can be modified to affect HCMV life cycle by deletion, insertion and substitution into the DNA sequence, as discussed herein, or by chemical synthesis of different amino acid sequence or by chemical modification. Truncated proteins can be formed by deletion of a portion of the DNA sequence or the introduction of termination signal(s) into the DNA sequence. Preferred deletions to the protein correspond to deleted amino acid sequence or sequences that contain at least one amino acid selected from the group consisting of Glu, Asp, Arg, Lys, Cys and Pro. More preferably at the deleted amino acid sequence or sequences contain at least two amino acids selected from the group consisting of Glu, Asp, Arg, Lys, Cys and Pro. More preferably the deleted amino acid sequence or sequences contain at least two prolines.

Other mutations of the protein useful in modifying HCMV life cycle include, but are not limited to, modification of cAMP phosphorylation (Arg/Lys-Arg/Lys-X-X-Asp/Glu) and/or, myristylization sites (Glycine-X1-X2-X3-Ser/Thr-X-X-Asp/Glu; where X1 is not Glu,Asp,Arg, Lys, His Pro, Phe, Tyr, Trp, where X2 is any amino acid and where X3 is not Pro), or modification of the PKC phosphorylation sites (Ser/Thr-X-Arg/Lys) and/or N-linked glycosylation sites (Asn-X-Ser/Thr; where X is not Pro).

The Toledo or Towne DNA sequences, analogs or fragments thereof can be expressed in a mammalian, insect, or microorganism host. The polynucleotide is inserted into a suitable expression vector compatible with the type of host cell employed and is operably linked to the control elements within that vector. Vector construction employs techniques which are known in the art. Site-specific DNA cleavage involved in such construction is performed by treating with suitable restriction enzymes under conditions which generally are specified by the manufacturer of these commercially available enzymes. A suitable expression vector is one that is compatible with the desired function (e.g., transient expression, long term expression, integration, replication, amplification) and in which the control elements are compatible with the host cell.

Mammalian Cell Expression

Vectors suitable for replication in mammalian cells are known in the art, and can include viral replicons, or sequences that ensure integration of the sequence encoding the Toledo or Towne DNA into the host genome. Exemplary vectors include those derived from SV40, retroviruses, bovine papilloma virus, vaccinia virus, other herpesviruses and adenovirus.

Such suitable mammalian expression vectors contain a promoter to mediate transcription of foreign DNA sequences and, optionally, an enhancer. Suitable promoters are known in the art and include viral promoters such as those from SV40, cytomegalovirus (CMV), Rous sarcoma virus (RSV), adenovirus (ADV), and bovine papilloma virus (BPV).

The optional presence of an enhancer, combined with the promoter described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when placed upstream or downstream from the transcription initiation site, in either normal or flipped orientation, or at a distance of more than 1000 nucleotides from the promoter. See Maniatis, *Science* 236:1237(1987), Alberts, *Molecular Biology of the Cell,* 2nd Ed. (1989). Enhancers derived from viruses may be particularly useful, because they typically have a broader host range. Examples include the SV40 early gene enhancer (see Dijkema, *EMBO J.* 4:761(1985)) and the enhancer/promoters derived from the long terminal repeat (LTR) of the RSV (see Gorman, *Proc. Natl. Acad. Sci.* 79:6777(1982b)) and from human cytomegalovirus (see Boshart, *Cell* 41:521(1985)). Additionally, some enhancers are regulatable and become active only in the presence of an inducer, such as a hormone or metal ion (see Sassone-Corsi and Borelli, *Trends Genet.* 2:215(1986)); Maniatis, *Science* 236:1237(1987)), In addition, the expression vector can and will typically also include a termination sequence and poly(A) addition sequences which are operably linked to the Toledo or Towne coding sequence.

Sequences that cause amplification of the gene may also be desirably included in the expression vector or in another vector that is co-translated with the expression vector containing a Towne or Toledo DNA sequence, as are sequences which encode selectable markers. Selectable markers for mammalian cells are known in the art, and include for example, thymidine kinase, diliydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

The vector that encodes a novel Toledo or Towne protein or polypeptide of this invention can be used for transformation of a suitable mammalian host cell. Transformation can be by any known method for introducing polynucleotide into a host cell, including, for example packaging the polynucleotide in a virus and transducing a host cell with the virus. The transformation procedure used depends upon the host to be transformed. Methods for introduction of heterologous polynucleotide into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

Insect Cell Expression

The components of an insect cell expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media. Exemplary transfer vectors for introducing foreign genes into insect cells include pAc373 and pVL985. See Luckow and Summers, *Virology* 17:31(1989).

The plasmid can also contains the polyhedron polyadenylation signal and a procaryotic ampicillin-resistance (amp) gene and origin of replication for selection and propagation in *E. coli.* See Miller, *Ann. Rev. Microbiol.* 42:177(1988).

Baculovirus transfer vectors usually contain a baculovirus promoter, i.e., a DNA sequence capable of binding a baculovirus RNA polymerase and initiating the downstream (5' to 3') transcription of a coding sequence (e.g., structural gene) into mRNA. The promoter will have a transcription initiation region which is usually placed proximal to the 5' end of the coding sequence and typically includes an RNA polymerase binding site and a transcription initiation site. A baculovirus transfer vector can also have an enhancer, which, if present, is usually distal to the structural gene. Expression can be either regulated or constitutive.

Yeast And Bacteria Expression

A yeast expression system can typically include one or more of the following: a promoter sequence, fusion partner sequence, leader sequence, transcription termination sequence. A yeast promoter, capable of binding yeast RNA polymerase and initiating the downstream (3') transcription of a coding sequence (e.g. structural gene) into mRNA, will have a transcription initiation region usually placed proximal to the 5' end of the coding sequence. This transcription initiation region typically includes an RNA polymerase binding site (a "TATA Box") and a transcription initiation site. The yeast promoter can also have an upstream activator sequence, usually distal to the structural gene. The activator sequence permits inducible expression of the desired heterologous DNA sequence. Constitutive expression occurs in the absence of an activator sequence. Regulated expression can be either positive or negative, thereby either enhancing or reducing transcription.

Particularly useful yeast promoters include alcohol dehydrogenase (ADH) (EP Patent Pub. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK)(EP Patent Pub. No. 329 203). The yeast PHO5 gene, encoding acid phosphatase, also provides useful promoter sequences. See Myanohara, *Proc. Natl. Acad. Sci. USA* 80:1(1983).

A Toledo or Towne DNA sequence, analog or an active fragment thereof can be expressed intracellularly in yeast. A promoter sequence can be directly linked with the sequence or fragment, in which case the first amino acid at the N-terminus of the recombinant protein will always be a methionine, which is encoded by the ATG start codon. If desired, methionine at the N-terminus can be cleaved from the protein by in vitro incubation with cyanogen bromide.

Intracellularly expressed fusion proteins provide an alternative to direct expression of a sequence. Typically, a DNA sequence encoding the N-terminal portion of a stable protein, a fusion partner, is fused to the 5' end of heterologous DNA encoding the desired polypeptide. Upon expression, this construct will provide a fusion of the two amino acid sequences. For example, the yeast or human superoxide dismutase (SOD) gene, can be linked at the 5' terminus of a sequence and expressed in yeast. The DNA sequence at the junction of the two amino acid sequences may or may not encode a clearable site. See, e.g., EP Patent Pub. No. 196 056. Alternatively, the polypeptides can also be secreted from the cell into the growth media by creating a fusion protein comprised of a leader sequence fragment that provides for secretion in yeast or bacteria of the polypeptides. Preferably, there are processing sites encoded between the leader fragment and the sequence that can be cleaved either in vivo or in vitro. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (FP Patent Pub. No. 12 873) and the A-factor gene (U.S. Pat. No. 4,588,684). Alternatively, leaders of non-yeast origin, such as an interferon leader, can be used to provide for secretion in yeast (EP Patent Pub. No. 60057). Transcription termination sequences recognized by yeast are regulatory regions located 3' to the translation stop codon. Together with the promoter they flank the desired heterologous coding sequence. These flanking sequences direct the transcription of an mRNA which can be translated into the polypeptide encoded by the DNA.

Typically, the above described components, comprising a promoter, leader (if desired), coding sequence of interest, and transcription termination sequence, are put together in plasmids capable of stable maintenance in a host, such as yeast or bacteria. The plasmid can have two replication systems, so it can be maintained as a shuttle vector, for example, in yeast for expression and in a procaryotic host for cloning and amplification. Examples of such yeast-bacteria shuttle vectors include YEp24 (see Botstein, *Gene* 8:17–24 (1979)), pCl/1 (see Brake, *Proc. Natl. Acad. Sci. USA* 81:4642–4646(1984)), and YRp17 (see Stinchcomb, *J. Mol. Biol.* 158:157(1982)). In addition, the plasmid can be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect on the host of the vector and the polypeptides. See, e.g., Brake, et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. See Orr-Weaver, *Methods In Enzymol.* 101:228–245(1983) and Rine, *Proc. Natl. Acad. Sci. USA* 80:6750(1983).

Typically, extrachromosomal and integrating expression vectors can contain selectable markers to allow for the selection of yeast strains that have been transformed. Selectable markers can include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker can also provide yeast with the ability to grow in the presence of toxic compounds, such as metal. For example, the presence of CUP1 allows yeast to grow in the presence of copper ions. See Butt, *Microbiol. Rev.* 51:351(1987).

Alternatively, some of the above described components can be put together into transformation vectors. Transformation vectors are typically comprised of a selectable marker that is either maintained in a replicon or developed into an integrating vector, as described above. Expression and transformation vectors, either extrachromosomal or integrating, have been developed for transformation into many yeasts. Exemplary yeasts cell lines are *Candida albicans* (Kurtz, *Mol. Cell. Biol.* 6:142(1986), *Candida maltosa* (Kunze, *J. Basic Microbiol.* 25:141(1985), *Hansenula polymorpha* (Gleeson, *J. Gen. Microbiol* 132:3459(1986) and Roggenkamp, *Mol. Gen. Genet.* 202:302(1986), *Kluyveromyces fragilis* (Das, *J. Bacteriol.* 158:1165(1984), *Kluyveromyces lactis* (De Louvencourt, *J. Bacteriol.* 154:737(1983) and Van den Berg, *Bio/Technology* 8:135(1990), *Pichia*

*guillerimondii* (Kunze, *J. Basic Microbiol.* 25:141(1985), *Pichia pastoris* (Cregg, *Mol. Cell. Biol.* 5:3376 (1985), *Saccharomyces cerevisiae* (Hinnen, *Proc. Natl. Acad. Sci. USA* 75:1929(1978) and Ito, *J. Bacteriol.* 153:163(1983), *Schizosaccharomyces pombe* (Beach and Nurse, *Nature* 300:706(1981), and *Yarrowia lipolytica* (Davidow, *Curr. Genet.* 10:380471(1985) and Gaillardin, *Curr. Genet.* 10:49 (1985).

Methods of introducing exogenous DNA into yeast hosts are well-known in the art, and typically include either the transformation of spheroplasts or of intact yeast cells treated with alkali cations. Transformation procedures usually vary with the yeast species to be transformed. See the publications listed in the foregoing paragraph for appropriate transformation techniques.

Additionally, the gene or fragment thereof can be expressed in a bacterial system. In such system, a bacterial promoter is any DNA sequence capable of binding bacterial RNA polymerase and initiating the downstream (3') transcription of a coding sequence (e.g. a desired heterologous gene) into MRNA. A promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*). See Raibaud, *Ann. Rev. Genet.* 18:173(1984). Regulated expression can therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (see Chang, *Nature* 198:1056(1977), and maltose. Additional examples include promoter sequences derived from biosynthetic enzymes such as tryptophan (trp) (see Goeddel, *Nuc. Acids Res.* 8:4057(1981), Yelverton, *Nuc. Acids Res.* 9:731(1981), U.S. Pat. No. 4,738,921 and EP Patent Pub. Nos. 36 776 and 121 775). The lactomase (bla) promoter system (see Weissmann, *Interferon* 3 (ed. I. Gresser), the bacteriophage lambda PL promoter system (see Shimatake, *Nature* 292:128(128) and the T5 promoter system (U.S. Pat. No. 4,689,406) also provides useful promoter sequences.

In addition, synthetic promoters which do not occur in nature also function as bacterial promoters. For example, transcription activation sequences of one bacterial or bacteriophage promoter can be joined with the operon sequences of another bacterial or bacteriophage promoter, creating a synthetic hybrid promoter such as the tac promoter (see U.S. Pat. No. 4,551,433, Amann, *Gene* 25:167 (1983) and de Boer, *Proc. Natl. Acad. Sci.* 80:21(1983)). A bacterial promoter can include naturally occurring promoters of non-bacterial origin that have the ability to bind bacterial RNA polymerase and initiate transcription. A naturally occurring promoter of non-bacterial origin can be coupled with a compatible RNA polymerase to produce high levels of expression of some genes in prokaryotes. The bacteriophage T7 RNA polymerase/promoter system is exemplary. (see Studier, *J. Mol. Biol.* 189:113(1986) and Tabor, *Proc. Natl. Acad. Sci.* 82:1074(1985)).

In addition to a functioning promoter sequence, an efficient ribosome binding site is also useful for the expression of the DNA sequence or fragment thereof in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon (see Shine, *Nature* 254:34(1975). The SD sequence is thought to promote binding of mRNA to the ribosome by the pairing of bases between the SD sequence and the 3' and of *E. coli* 16S rRNA (see Steitz, *Biological Regulation and Development: Gene Expression* (ed. R. F. Goldberger)(1979)).

The novel Toledo or Towne proteins of the invention can be expressed intracellularly. A promoter sequence can be directly linked with a novel Toledo or Towne DNA sequence, analog or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase. See EP Patent Pub. No. 219 237.

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of an sequence fragment thereof and expressed in bacteria. The resulting fusion protein preferably retains a site for a processing enzyme (factor Xa) to cleave the bacteriophage protein from the sequence or fragment thereof (see Nagai, *Nature* 309:810(1984). Fusion proteins can also be made with sequences from the lacZ gene (Jia, *Gene* 60:197 (1987),the trpE gene (Allen, *J. Biotechnol.* 5:93(1987) and Makoff, *J. Gen. Microbiol.* 135:11(1989), and the Chey gene (EP Patent Pub. No. 324 647) genes. The DNA sequence at the junction of the two amino acid sequences may or may not encode a clearable site. Another example is a ubiquitin fusion protein. Such a fusion protein is made with the ubiquitin region that preferably retains a site for a processing enzyme (e.g., ubiquitin specific processing-protease) to cleave the ubiquitin from the polypeptide. Through this method, mature Towne or Toledo polypeptides can be isolated. See Miller, *Bio/Technology* 7:698(1989).

Alternatively, proteins or polypeptides can also be secreted from the cell by creating chimeric DNA molecules that encode a fusion protein comprised of a signal peptide sequence fragment that provides for secretion of the proteins or polypeptides in bacteria. (See, for example, U.S. Pat. No. 4,336,336). The signal sequence fragment typically encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the protein or polypeptide.

DNA encoding suitable signal sequences can be derived from genes for secreted bacterial proteins, such as the *E. coli* outer membrane protein gene (ompA) (Masui, Experimental Manipulation of Gene Expression (1983) and Ghrayeb, *EMBO J.* 3:2437(1984)) and the *E. coli* alkaline phosphatase signal sequence (ohoA) (see Oka, *Proc. Natl. Acad. Sci.* 82:7212(1985). The signal sequence of the alpha-amylase gene from various Bacilus strains can be used to secrete heterologous proteins from *B. subtilis* (see Palva, *Proc. Natl. Acad. Sci.* 79:5582(1982) and EP Patent Pub. No. 244 042).

Transcription termination sequences recognized by bacteria are regulatory regions located 3' to the translation stop codon. Together with the promoter they flank the coding sequence. These sequences direct the transcription of an mRNA which can be translated into the Towne or Toledo protein or polypeptide encoded by the DNA sequence. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the promoter, signal sequence (if desired), coding sequence of interest, and transcription termination sequence are maintained in an extrachromosomal element (e.g., a plasmid) capable of stable maintenance in the bacterial host. The plasmid will have a replication system, thus allowing it to be maintained in the bacterial host either for expression or for cloning and amplification. In addition, the plasmid can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. See e.g., EP Patent Pub. No. 127 328.

Typically, extrachromosomal and integrating expression constructs can contain selectable markers to allow for the selection of bacterial strains that have been transformed. Selectable markers can be expressed in the bacterial host and can include genes which render bacteria resistant to drugs such as ampicillin, chorampheicol, erythromycin, kanamycin (neomycin), and tetracycline (see Davies, *Ann. Rev. Microbiol.* 32:469(1978). Selectable markers can also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in an extrachromosal vector or an integrating vector, as described above.

Expression and transformation vectors, either extrachromosornal or integrating, have been developed for transformation into many bacteria. Exemplary are the expression vectors disclosed in Palva, *Proc. Natl. Acad. Sci.* 79:5582 (1982), EP Patent Pub. Nos. 036 259 and 063 953 and PCT Patent Publication WO 84/04541 (for *B.subtilis*); in Shimatake, *Nature* 292:128(1981), Amann, *Gene* 40:183 (1985), Studier, *J. Mol. Biol.* 189:113(1986) and EP Patent Pub. Nos. 036 776, 136 829 and 136 907 (for *E. coli*); in Powell, *Appl. Environ. Microbiol.* 54:655(1988) and U.S. Pat. No. 4,745,056 (for Streptococcus).

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Exemplary methodologies can be found in Masson, *FEMS Microbiol. Let.* 60:273(1989), Palva, *Proc. Natl. Acad. Sci.* 79:5582(1982), EP Patent Pub. Nos. 036 259 and 063 953 and PCT Patent Pub. WO 84/04541 for Bacillus transformation. For campylobacter transformation, see e.g., Miller, *Proc. Natl. Acad. Sci,* 85:856(1988) and Wang, *J. Bacteriol.* 172:949(1990). For *E. coli,* see e.g., Cohen, *Proc. Natl. Acad. Sci.* 69:2110(1973), Dower, *Nuc. Acids Res.* 16:6127 (1988), Kushner, *Genetic Engineering: Proceedings of the International Symposium on Genetic Engineering* (eds. H. W. Boyer and S. Nicosia), Mandel, *J. Mol. Biol.* 53:159 (1970) and Taketo, *Biochem. Biophys. Acta* 949:318(1988). For Lactobacillus and Pseudomonas, see e.g., Chassy, *FEMS Microbiol. Let.* 44:173(1987) and Fiedler, *Anal. Biochem.* 170:38(1988), respectively. For Streptococcus, see e.g., Augustin, *FEMS Microbiol. Let.* 66:203(1990), Barany, *J. Bacteriol.* 144:698(1980), Harlander, *Streptococcal Genetics* (ed. J. Ferretti and R. Curtiss III)(1987), Perry, *Infec. Immun.* 32:1295(1981), Powell, *Appl. Environ. Microbiol.* 54:655(1988) and Somkuti, *Proc. 4th Evr. Cong. Biotechnology* 1:412(1987).

The present invention is illustrated by the following examples.

MATERIALS AND METHODS

A. Cells and virus

Human CMV strains AD169, Towne and Toledo were obtained from E. S. Mocarski (Stanford University) and were used for all experiments. Two of these strains are also available through the ATCC, Accession Nos. VR-538 (AD169) and VR-977 (Towne). Virus was grown in cultures of human foreskin fibroblast (HF) cells with Dulbecco's modified Eagle's medium (DME) (JRH Biosciences, Lenexa, Kans.) as previously described in Spaete and Mocarski, *J. Virol* 56:13543(1985), but supplemented with 10% fetal calf serum (FCS) (JRH Biosciences, Lenexa, Kans.), L-glutamine (2 mM), penicillin (100 units/ml), streptomycin (0.1 mg/ml) and pyruvate (1 mM). To prepare AD169, Towne and Toledo strain CMV DNAs by centrifugation to equilibrium on NaI gradients as previously described in Spaete and Mocarski,*J. Virol* 54:817–24(1985), roller bottles were infected with the CMV strains at a multiplicity of infection (MOI) of 0.001 plaque forming units (pfu)/cell to minimize the production of defective virus particles. The infected cells were refed at four days post infection with medium. At eight days post infection when the monolayer was well infected, cells were scraped into a 50 ml conical tube in 10 mis media per roller bottle and pelleted at 1000 revolutions per minute (rpm) for 10 minutes. Pellets were resuspended in 2.0 ml 0.01 M Tris and 0.01 EDTA (TE) (pH 7.4) with 1% NP40, 1% deoxycholate and incubated on ice until all cellular nuclei were lysed when viewed under a microscope. Lysates were transferred to a 2059 tube (Falcon) and spun at 2600 rpm for 5 minutes at 4° C. Supernatants were transferred to another 2059 tube and RNAse (Worthington-DNase free) was added at 50 µg/ml followed immediately by Proteinase K (200 µmg/ml) and 1% sodium dodecyl sulfate (SDS). Supernatants were incubated in a 65° C. water bath for 60 minutes, brought to 16 ml with TE, pH 7.4, added to 24 mls of saturated NaI and 0.15 ml ethidium bromide (5 mg/ml). Samples were centrifuged to equilibrium at 55,000 rpm at 20° C. for 24 hours in a Beckman Ti70 rotor, Fractions containing the viral DNA were extracted with butanol equilibrated with TE with gentle rocking followed by centrifugation at 3,000 rpm for 10 min at 20° C. and further extracted 2 to 3 times with butanol to reduce volume. Samples were extracted with an equal volume of isoamyl alcohol equilibrated with TE, spun and re-extracted. DNA was dialyzed against three changes of TE with 1% phenol and 1 M NaCl. The $OD_{260}$ and $OD_{280}$ were read to determine purity of the AD169, Toledo and Towne DNA.

Clinical isolates were obtained from M. Fiala (Rancho Mirage, Calif.), and S. Chou (Oregon Health Sciences University). Rapid isolation of HCMV infected cell viral DNA was carried out as previously described in Spaete and Frenkel, Cell 30:295–304(1982), except that DNA was not radiolabeled before purification. Briefly, infected cell monolayers (25 $cm^2$ flasks) were rinsed twice with phosphate-buffered saline (PBS) and lysed in a 1.0 ml solution of 0.1 M NaCl, TE, pH 8.0, 0.05% SDS and 0.1 mg/ml Proteinase K. Lysates were incubated 2–24 hours at 37° C., extracted twice with 1 volume of phenol, 1 volume of chloroform followed by centrifugation at 2500 rpm for 5 minutes to separate phases. The aqueous phase was extracted twice with 1 volume of ether and the DNA was precipitated with 0.1 volume 3 M NaAC and two volumes of ethanol or isopropanol. DNA was chilled, collected by centrifugation or spooled on a glass rod, dried and resuspended in TE.

B. Plasmid DNA

Plasmids pXbaI E, pXbaI T and pXbaI Q (Thomsen and Stinski, 1981), representing Towne strain map units 0.69 to 0.8, were obtained from M. Stinski (University of Iowa).

Clone 65 was derived by cloning a gel extracted BamHI digested Toledo DNA fragment into the BamHI site of plasmid, pGEM®-3Zf+ (Promega, Madison, Wis.) Briefly, five µg of Toledo DNA was digested with 40 units of BamHI and electrophoresed in a preparative 1% low-melting-point agarose gel for 490 volt hours in 1×TAE buffer. Toledo DNA migrating at ca. 5 kilobase pairs (kbp) was excised and the agarose was digested with 2 units of β-agarase I (New England BioLabs, Beverly, Mass.). This DNA fragment was precipitated with 2 volumes of isopropanol, chilled to −20° C., spun in an Eppendorf centrifuge for 15 minutes, dried and resuspended in 50 µl TE. The gel extracted fragment was ligated to BamHI digested pGEM®-3Zf+ using T4 DNA ligase (New England BioLabs, Beverly, Mass.), and an aliquot of the ligation mixture was used to transform competent *Escherichia coli* XL-1 Blues (Stratagene, La Jolla, Calif.) by the calcium shock method (Mandel and Higa, 1970), or by electroporation using methods as written in the Pulse Controller Guide published by BioRad (Richmond, Calif.).

Cosmid 1 is a ca. 53 kbp partially digested HindIII fragment of Toledo DNA spanning 0.69 to 0.87 map units cloned into cosmid pHC79 (Hohn and Collins, 1980) obtained from E. S. Mocarski (Stanford University). Subcloned from cosmid 1 were the following:

Clones 4 and C1300 were derived by cloning BamHI digested fragments from Cosmid 1 cloned into a Bluescript M13+ plasmid vector. As such, these clones represent Toledo DNA sequence spanning portions of Cosmid 1.

Clone C23K was derived as a complete BamHI digested fragment of Cosmid 1 DNA and circularized by ligation.

C. Preparation of radioactively labeled probes and hybridization

Plasmid or viral DNA was radioactively labeled in vitro by nick translation (Rigby et al., 1977) with a kit (Boehringer Mannheim), and using [$\alpha^{32}$P]dCTP (Amersham Corp.). Hybridizations to immobilized CMV DNA were performed essentially as described by Spaete and Mocarski, J. Virol 54:817–24 (1985), but at 68° C. in a solution of 6×SSC (1×SSC is 0.15 M NaCl plus 0.015 M sodium citrate), 0.2% polyvinylpyrrolidone, 0.2% Ficoll, 0.2% bovine serum albumin, and 0.1% sodium dodecyl sulfate, with the amount of salmon sperm DNA being changed from 25 µg/ml to 100 µg/ml and 30% formamide being reduced to 15%.

DNA was transferred to Hybond-N+ nylon transfer membranes (Amersham Corp.), after restriction enzyme digestion and electrophoresis in 1% agarose gels by standard techniques (Maniatis et al., 1982). DNA was cross-linked to the membrane with 120,000 microjoules/$cm^2$ of UV irradiation using a UV Crosslinker 1000 (Hoefer Scientific Instruments, San Francisco, Calif.). Membranes were prehybridized 1 hour at 68° C. in solution A (6×SSC, 0.2% polyvinylpyrrolidone, 0.2% Ficoll, 0.2% bovine serum albumin, 0.1% sodium dodecyl sulfate, 100 µg/ml salmon sperm DNA and 15% formamide), then nick-translated [$\alpha^{32}$P]-labeled probe in a solution containing 100 µg/ml salmon sperm DNA was denatured by boiling for five minutes, snap-cooled on ice, added to the membrane and allowed to hybridize overnight at 68° C. After hybridization, unannealed probe was removed by rinsing the membrane 3× with 2×SSC followed by reincubation in solution A lacking salmon sperm DNA at 68° C. for 15 minutes. The washing procedure was repeated, the blot was rinsed in a large volume of 2×SSC at room temperature, the membrane was air dried and autoradiographed using Kodak X-AR film.

D. Nucleotide sequence determination and analysis

All nucleic acid sequences were determined by the dideoxynucleotide chain termination method (Sanger et al., 1977). A variety of templates were prepared for sequencing; they included single-stranded phage DNA, double-stranded plasmid and cosmid DNA, viral genomic DNA, and PCR products. Manual and automated sequencing (with an ABI 373A instrument) were employed. Both one-cycle and multi-cycle sequencing protocols were used. The sequence was determined for both strands. Ambiguous regions were corrected by additional sequencing after proofreading. The primers used for sequencing were synthesized on an ABI 392 instrument (Applied Biosystems). The contig and analysis of the sequence were performed using MacDNASIS (Hitachi). The homology searches were performed using the BLAST program through NCBI services.

EXAMPLE 1

Identification of Novel Sequences in the Genomes of CMV Towne and Toledo Strain Isolates To determine the cross representation of DNA sequences in the Towne and Toledo strains of CMV, viral DNA from each strain was digested to completion with XbaI, ClaI, BamHI, BglII, EcoRI, and HindIII. After electrophoresis through a 1% agarose gel, the CMV DNAs were denatured in 0.2 M NaCl/0.6 M NaOH, neutralized in 0.6 M NaCl/1 M Tris, pH 7.5, in situ, and the gel was soaked in 20×SSC for 30 minutes. Stereo blots were prepared by placing identically sized Hybond-N+ nylon membranes (Amersham Corp.), on either side of the gel and transferring the DNAs to the membranes in both directions using the capillary action of paper towels. After blotting overnight in 20×SSC, the membranes were washed in 2×SSC and the DNA was immobilized on the membrane by UV irradiation as described above.

DNA probes of Towne and Toledo DNA with an average size of 500 bp were prepared by sonicating 10 µg of each DNA in a 2063 tube (Falcon Plastics) using 4 pulses of 10 seconds each at a setting of 3 on a Heat Systems, Inc. sonicator (Farmingdale, N.Y.). Following sonication, the viral DNAs were digested with the restriction enzymes AvaI, BanI and BfaI, to further reduce the size complexity of the probe DNA. These enzymes were chosen because a search of the AD169 DNA database sequences (EMBL accession number X17403), revealed abundant cut sites (326, 386, and 341, respectively); their restriction enzyme digestion buffers are compatible; and their sites do not overlap. Ethidium bromide stained gels of the sheared viral DNAs prepared in this manner revealed a range of DNA sizes from 1300 bp to less than 100 bp, with the majority of DNA migrating at approximately 300 bp as judged by comigration with a HaeIII digested ØX174 DNA standard marker (New England BioLabs, Beverly, Mass.). The Towne and Toledo sheared probe DNA was then nick translated using $[\alpha^{32}P]$ dCTP (Amersham Corp.) as described above and each probe was applied to stereo blots of immobilized, restriction enzyme digested, Towne and Toledo DNAs. After hybridization and autoradiography, the hybridization patterns were analyzed to determine the fragments on each DNA profile which did not hybridize with the heterologous strain probe but did hybridize with the homologous strain probe. For example, the loss of a signal for a prominent 5 kbp band on the BamHI digest of Toledo DNA when using the Towne probe, which was present when the Toledo DNA was used to probe itself, revealed a region of sequence divergence between the two isolates (see FIG. 3).

This 5 kbp fragment was cloned by gel extraction as described above and designated clone 65. The clone 65 Toledo DNA was sequenced in its entirety and compared to Towne DNA sequence generated from the pXbaI T clone which was shown to be divergent from AD169 DNA sequences (see Example 2 below). The full sequence of clone 65 is shown in FIG. 1. In FIG. 1, Clone 65 begins with nucleotide 4664 and ends with nucleotide 9327. Surprisingly, the DNA from the pXbaI T clone of Towne DNA (1,856 bp) and clone 65 of Toledo DNA (4,668 bp) shared 104 bp of sequence identity. This small stretch of sequence homology allowed mapping of the region of Toledo DNA divergence to the boundary of the Unique Long ($U_L$) component and the inverted repeats (alternatively termed IRL or b' sequences) on the AD169 and Towne DNA maps. These newly isolated Toledo strain nucleotide sequences from clone 65 were not represented in the reference laboratory strain, AD169, which has been sequenced in its entirety by Chee and colleagues (EMBL accession number X17403).

EXAMPLE 2

Identification of Novel Sequences in the Genome of CMV Towne Not Found in Reference Strain AD169

DNA sequence heterogeneity between the Towne strain and the AD169 strain has been found. See, Pritchett, *J. Virology* 36:152–61 (1980). However, although the gross structural organization of the CMV genome has been determined and strain to strain restriction site polymorphisms have been mapped for many strains, strain-to-strain differences on the nucleotide level have not been determined. The laboratory strain AD169 was the first CMV isolate to be sequenced and has served as the reference strain in defining the genetic complexity of the CMV genome.

In order to examine nucleotide sequence differences between Towne and AD169, we focused on the region shown to be divergent in the Toledo strain, i.e. the boundary between the $U_L$ component and the b' sequences, as explained in detail in Example 1. Plasmid pXbaI T was labeled using the NEBlot™ Phototopel Detection Kit (New England Biolabs, Beverly, Mass.), and used as a probe on blots of immobilized restriction enzyme digested Towne, Toledo and AD169 DNAs. Briefly, pXbaI T was linearized with PvuII, ethanol precipitated and resuspended in 34 µl of nuclease free water. The plasmid was denatured in boiling water for five minutes, snap cooled on ice for five minutes and centrifuged briefly at 4° C. The following reagents were added to the tube in the order listed: 10 µl of 5× labeling mix, 5 µl of dNTP mix, 1 µl of DNA polymerase I (Klenow fragment). The mix was incubated at 37° C. for 6 hours and the reaction was terminated by adding 5 µl of 0.2 M EDTA, pH 8.0. The probe was precipitated by adding 5 µl of 4 M LiCl and 150 µl of ethanol, chilling to −80° C. for 30 minutes, pelleted in an Eppendorf centrifuge, washed with 70% ethanol and resuspended in 20 µl of Resuspension Buffer as supplied by the kit. The hybridization reaction was essentially as described above except that after hybridization the membrane was washed twice in 2×SSC, 0.1% SDS at room temperature for 5 minutes each followed by two washes in 0.1×SSC, 0.1% SDS at 68° C. for 15 minutes. The detection reactions link the biotinylated probes to alkaline phosphatase through a strepavidin bridge and the hybridized probe was visualized by cleavage of the Lumigen-PPD substrate. The blocking steps, strepavidin incubation, alkaline phosphatase incubation and Lumigen-PPD reaction were carried out as described in the kit manual. Exposure of the blots to Kodak XAR film revealed that, as expected, (i) an XbaI digested fragment of sized 1.85 kbp (XbaI T) was hybridized on Towne DNA probed with pXbaI T and (ii) a comigrating XbaI digested fragment was present in Toledo DNA. The AD169 DNA failed to show any hybridization signal on any of the restriction enzyme digestion patterns. Nucleotide sequence of pXbaI T confirmed the total lack of identity of the Towne DNA and AD169 DNA. Nucleotide sequencing of cosmid I DNA (see B. Plasmid DNA in Material and Methods, above) from Toledo revealed extensive sequence identity between the newly identified Towne DNA and the Toledo DNA of cosmid 1 in this region. Surprisingly, the orientation of the sequence was reversed in Toledo relative to Towne.

EXAMPLE 3

Identification of Novel Toledo DNA Sequences in the Genomes of Recent Clinical Isolates and not Found in Reference Strain AD169

To determine the penetrance of sequences represented by clone 65 in recent clinical isolates, five representative clinical isolates (HCMVF, C128, C354, C793 and C980) were digested with restriction enzymes BamHI and XbaI along with the Toledo, Towne and AD169 DNAs prepared as described in the Materials and Methods section above, electrophoresed through agarose, transferred to a Hybond-N+ nylon transfer membrane, and probed with nick-translated $[\alpha^{32}P]$-labeled clone 65 according to the procedures outlined in the Materials and Methods section. As can be seen in FIG. 4, the autoradiographs revealed that homology was detected in all of the clinical isolates. In FIG. 4, a band at ca. 5 kbp is visible in lane 1 (the Toledo DNA), appears in Towne DNA (lane 2), is missing from lane 3 (the AD 169 DNA), and visible in lanes 4 through 8 (the clinical isolates HCMVF, C128, C354, C793 and C980). These results demonstrate that the newly isolated sequence found in the Toledo strain of HCMV is also present in the recent clinical isolates but is not present in the AD169 reference strain. Nucleotide sequence analysis reveals the reason for the weak hybridization signal to the Towne DNA fragment is due to the existence of only 151 nucleotides of sequence identity with Towne DNA. The shared 104 bp sequence identity in Example 1 is responsible for a weak hybridization signal to DbaI "T" sized fragments from both Towne and Toledo DNAs seen in the XbaI digests (lanes 9 and 10). The XbaI digest of the clinical isolates (lanes 12 through 16) also reveals hybridization to multiple high molecular weight bands. Analysis of these and other clinical isolate genomes with other probes in the region has revealed that the shared sequences may be in inverted orientation in some isolates relative to the orientation in the Toledo strain.

FIG. 6 is a schematic illustration of the relative positions of novel sequences identified in Toledo genomic DNA, Towne genomic DNA in a comparison with AD169 strain genomic DNA. The dashed lines delimit the region of the genome where homologous and divergent sequences are found. The top line illustrates a Toledo DNA restriction map showing BamHI (indicated by "B") and XbaI (indicated by "X") restriction enzyme sites extending between the homology breakpoints identified by inverted triangles at nucleotides 175068 and 188843 (numbered with reference to the AD169 DNA sequence—EMBL accession number X17403). Subclones 4, 1300, C23K and 65 of the Toledo DNA sequence are shown in boxes above the map. An inverted region of homology with respect to Towne is shown by the inverted triangles between nucleotides 178221 and 175082. Unique sequences are shown by a thin line, and inverted repeat sequences denoted by thick lines, b'a'c'. The end of the c' repeats is shown with an arrow at nucleotide 191412. The muddle line illustrates a Towne DNA restriction map showing BamHI (B) and XbaI (X) restriction enzyme sites as described above for Toledo and showing XbaI clones E, T, and Q in boxes below. Shaded area refers to homologous regions shared with Toledo DNA but inverted in orientation. Nucleotide numbers shown are with reference to the AD169 DNA sequence. Undetermined extent of b' repeat sequences in the Towne strain is shown by thin lines at AD169 strain nucleotide reference 180034. The bottom line illustrates the AD169 genome displayed in the prototype orientation. Unique sequences are displayed by a tin line, and inverted repeats of the long ($U_L$) and short ($U_S$) components are denoted by boxes, ab–b'a', and a'c'–ca. The a sequence, is a terminal direct repeat with an inverted copy (a'), at the junction of the long and short components. The length of the AD169 DNA sequence is indicated as 229354 nucleotides and the map position of the internal repeats are shown with the nucleotide reference numbers and arrows.

EXAMPLE 4

Open Reading Frame Analysis of the Novel Toledo and Towne DNA Sequences

The novel Toledo and Towne sequences encoded potential open reading frames (ORPs). Using an arbitrarily chosen parameter of 10 kiloDaltons as the minimum calculated protein molecular weight, a total of 36 ORFs were identified in the novel Toledo sequence and a total of 4 ORFs were identified in the novel Towne sequence. The putative amino acid sequences of these ORFs are set forth in the sequence listing (SEQ ID NOS:2, 3, 4, 5, 7, 8, 9, 10, 11, 12, 13, 14, 15, 16, 17, 18, 19, 20, 21, 22, 23, 24, 25, 26, and 27). FIG. 5 shows the schematic presentation of these ORFs in the novel Toledo and Towne DNA sequences, together with previously reported AD169 ORFs of the corresponding region. Names were assigned for these ORFs starting from UL133 as the first ORE at the left side of the UL in Toledo sequence. The first ORF in the novel Towne sequence was assigned as UL147, which was determined to be present in the novel Toledo sequence disclosed here. UL130 and UL132 in AD169 were determined to be present in the novel Toledo sequence. Additionally, UL153 and UL154 exhibited regions of homology to IRL14 and IRL12, respectively. All ORFs were searched for homologous sequence in the non-redundant databases of NCBI using the BLASTP program. Among all ORFs searched, only UL132 identified a homologue in the database, which was HCMV mtrIII (GenBank Accession No. X75606), exhibiting 76% identity at the amino acid level. The solid circle identified the ORFs that contained the potential N-linked glycosylation site sequence, N-X(-P)-S/T. These potential glycoproteins may be biologically significant as antigenic or immunogenic molecules.

The present investigation is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. An isolated DNA sequence comprising at least one complete open reading frame of SEQ ID NO:6.

2. The isolated DNA sequence of claim 1, wherein the open reading frame encodes a Toledo protein comprising SEQ ID NO:13, SEQ ID NO: 14, SEQ ID NO: 15, SEQ ID NO: 16, SEQ ID NO:17, SEQ ID NO: 18, SEQ ID NO: 19, SEQ ID NO: 20, SEQ ID NO:21, or SEQ ID NO:22.

3. The isolated DNA sequence of claim 2, additionally comprising an open reading frame encoding SEQ ID NO: 7.

4. The isolated DNA sequence of claim 1 comprising an open reading frame encoding SEQ ID NO: 22.

5. The isolated DNA sequence of claim 1, wherein said isolated DNA sequence additionally comprises at least one open reading frame from a human cytomegalovirus strain.

6. The isolated DNA sequence of claim 5 wherein said isolated DNA sequence comprises a replicable genome of cytomegalovirus that encodes an infectious human cytomegalovirus.

7. An RNA molecule transcribed from the sequence of claim 1.

8. A vector comprising the DNA sequence of claim 1.

9. A host cell transformed with the DNA sequence of claim 1, in operative association with an expression control sequence that directs replication and expression of said DNA sequence.

10. A method of producing a human cytomegalovirus protein comprising culturing the host cell of claim 9 in a suitable culture medium under appropriate conditions permitting DNA expression and isolating said protein from said medium.

* * * * *